US011530415B2

(12) United States Patent
Ding et al.

(10) Patent No.: US 11,530,415 B2
(45) Date of Patent: Dec. 20, 2022

(54) GENETICALLY ENGINEERED *STREPTOMYCES* CAPABLE OF THAXTOMIN PRODUCTION IN THE ABSENCE OF THAXTOMIN-INDUCING CONDITIONS AND METHODS OF PRODUCING THAXTOMIN

(71) Applicant: University of Florida Research Foundation, Inc., Gainesville, FL (US)

(72) Inventors: Yousong Ding, Gainesville, FL (US); Guangde Jiang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 41 days.

(21) Appl. No.: 16/768,347

(22) PCT Filed: Nov. 29, 2018

(86) PCT No.: PCT/US2018/063130

§ 371 (c)(1),
(2) Date: May 29, 2020

(87) PCT Pub. No.: WO2019/108836

PCT Pub. Date: Jun. 6, 2019

(65) Prior Publication Data

US 2020/0362298 A1 Nov. 19, 2020

Related U.S. Application Data

(60) Provisional application No. 62/591,876, filed on Nov. 29, 2017.

(51) Int. Cl.
*C12N 15/76* (2006.01)
*C12N 1/20* (2006.01)
*C12P 17/16* (2006.01)
*A01N 63/28* (2020.01)

(52) U.S. Cl.
CPC ............ *C12N 15/76* (2013.01); *A01N 63/28* (2020.01); *C12N 1/20* (2013.01); *C12P 17/165* (2013.01); *C12N 2510/02* (2013.01)

(58) Field of Classification Search
None
See application file for complete search history.

(56) References Cited

U.S. PATENT DOCUMENTS 5,435,730 A 7/1995 Adams et al.
2010/0167930 A1 7/2010 Koivunen et al.
2017/0306368 A1 10/2017 Loria et al.

FOREIGN PATENT DOCUMENTS

WO 2010121079 A2 10/2010

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Luo et al. ACS Synth Biol. Sep. 18, 2015;4(9):1001-10. Epub May 7, 2015 (Year: 2015).*
Accession AF255732. Dec. 22, 2000 (Year: 2000).*
Accession FN554889. Feb. 27, 2015 (Year: 2015).*
Accession AF393159. Mar. 12, 2002 (Year: 2002).*
Accession AY204508. May 7, 2004. (Year: 2004).*
Accession FN554889. Feb. 27, 2015. Alignment to SEQ ID No. 9 (Year: 2015).*
Accession FN554889. Feb. 27, 2015—Alignment to SEQ ID No. 11 (Year: 2015).*
Accession EU119868. Oct. 25, 2007 (Year: 2007).*
International Search Report for PCT/US2018/063130 dated May 8, 2019.
Zhang, et al. "Emergence of novel pathogenic *streptomyces* species by site-specific accretion and cis-mobilization of pathogenicity islands," Molecular Plant-Microbe Interactions, Jan. 2017, vol. 30, No. 1, pp. 72-82.
Zhang, et al. "Promiscuous pathogenicity islands and phylogeny of pathogenic Streptomyces spp." Molecular Plant-Microbe Interactions, Aug. 2016, vol. 29, No. 8, pp. 640-650.
Zhang et al., "Total Synthesis of Thaxtomin A and its Stereoisomers and Findings of their Biological Activities," Org. Lett. 2013, vol. 15, No. 22, p. 5670-5673.
Zhang et al., "Synthesis and Biological Evaluations of a Series of Thaxtomin Analogues", J. Agric. Food Chem., 2015, 63, 3734-3741.

(Continued)

*Primary Examiner* — Christian L Fronda
(74) *Attorney, Agent, or Firm* — Thomas Horstemeyer, LLP

(57) ABSTRACT

The present disclosure includes refactored thaxtomin biosynthetic gene clusters including thaxtomin modules including one or more thaxtomin genes such that the expression of the refactored thaxtomin biosynthetic gene cluster produces at least one thaxtomin compound in the absence of thaxtomin-inducing conditions. Also included are genetically engineered *Streptomyces* bacterium from a non-pathogenic *Streptomyces* strain comprising an exogenous, refactored thaxtomin biosynthetic gene cluster of the present disclosure, such that the expression of the refactored thaxtomin biosynthetic gene cluster provides the genetically engineered *Streptomyces* bacterium with the ability to produce at least one thaxtomin compound in the absence of thaxtomin-inducing conditions. The present disclosure also includes methods of producing thaxtomin compounds, analogs, or intermediate with the refactored thaxtomin biosynthetic gene clusters and genetically engineered bacteria of the present disclosure.

20 Claims, 7 Drawing Sheets

Specification includes a Sequence Listing.

(56) References Cited

OTHER PUBLICATIONS

Zabruannyi et al., "Insights into Naturally Minimised Streptomyces albus J1074 Genome," A. BMC Genomics., 2014, 15:97, p. 1-11, http://www.biomedcentral.com/1471-2164/15/97.
Wach, et al., "Effect of Carbohydrates on the Production of Thaxtomin A by Streptomyces acidiscabies", Arch Microbiol. 2007, 188:81-88.
Smanski et al., "Synthetic Biology to Access and Expand Nature's Chemical Diversity," Nature Reviews Microbiology, Mar. 2016, vol. 14, 135-139.
Scheible et al., "An *Arabidopsis* Mutant Resistant to Thaxtomin A, a Cellulose Synthesis Inhibitor from *streptomyces* Species," Plant Cell., Aug. 2003, vol. 15, 1781-1794.
Molesworth et al., "Synthesis and Phytotoxicity of Structural Analogues of Thaxtomin Natural Products", Aust. J. Chem., 2010, 63, 813-820.
Luo et al., "Systematic Indentification of a Panel of Strong Constitutive Promoters from Streptomyces albus," ACS Synth. Biol., 2015, 4, 1001-1010.
Lawrence et al., "Induction of Common Scab Symptoms in Aseptically Cultured Potato Tubers by the Vivotoxin Thaxtomin," pHYTOPATHOLOGY, 1990, 80, 606-608.
Krasnoff et al., "Chemistry and Phytotoxicity of Thaxtomin A Alkyl Ethers," J. Agric. Food Chem., 2005, 53, 9446-9451.
King et al., "The Thaxtomin Phytotoxins: Sources, Synthesis, Biosynthesis, Biotransformation and Biological Activity," Phytochemistry., 2009, 70, 833-841.
King et al., "Herbicidal Properties of Thaxtomin Group of Phytotoxins," J. Agric. Food Chem., 2001, 49, 2298-2301.
King et al., "Isolation and Characterization of Phytotoxins Associated with Streptomyces scabies," J. Chem. Soc., Chem. Commun., 1989, 849-850.
King et al., "Synthesis and NMR Characteristics of N-acetyl-4-nitro, N-acetyl-5-nitro, N-acetyl-6-nitro and N-acetyl-7-nitrotryptophan methyl Esters," Magn. Reson. Chem., 2009, 47, 273-276.
King et al., "Characterization of New Thaxtomin A Analogues Generated in Vitro by Streptomyces scabies," J. Agric. Food Chem., 1996, 44, 1108-1110.
King et al., "Isolation and Characterization of Thaxtomin-Type Phytotoxins Associated with Streptomyces ipomoeae," J. Agric. Food Chem., 1994, 42, 1791-1794.
King et al., "Chemistry of Phytotoxins Associated with Streptomyces scabies, the Causal Organism of Potato Common Scab," J. Agric. Food Chem., 1992, 40, 834-837.
King, R.R., "Synthesis of Thaxtomin C," Canadian Journal of Chemistry, 1997, 75, 1172-1173.
Hüter, O.F., "Use of Natural Products in the Crop Protection Industry," Phytochem. Rev., 2010, 10, 185-194.
Healy et al., "Involvement of a Cytochrome P450 Monooxygenase in Thaxtomin A Biosynthesis by Streptomyces acidiscabies," J. Bacteriol., 2002, vol. 184, No. 7, 2019-2029.
Goyer et al., "Ultrastructural Effects of Thaxtomin A Produced by Streptomyces scabies on Mature Potato Tuber Tissues," C. Can. J. Bot., 2000, 78, 374-380.
Fry et al., "Thaxtomin A: Evidence for a Plant Cell Wall Target," Physiol. Mol. Plant Pathol., 2002, 60, 1-8.
Feng et al., "Engineered Production of Iso-Migrastatin in Heterologous Streptomyces Hosts," Bioorg. Med. Chem., 2009, 17, 2147-2153.
Duke et al., "Natural Toxins for Use in Pest Management," Toxins, 2010, 2, 1943-1962.
Dayan et al., "Rationale for a Natural Products Approach to Herbicide Discovery," Pest Manage. Sci., 2012, 68, 519-528.
Copping et al., "Natural Products That Have Been Used Commercially as Crop Protection Agents," Pest Manage. Sci., 2007, 63, 524-554.
Cantrell et al., "Natural Products as Sources for New Pesticides," J. Nat. Prod., 2012, 75, 1231-1242.
Bourgault et al., "A One-Pot Multicomponent Coupling/Cyclizatio for Natural Product Herbicide (+)-Thaxtomin A," Org. Biomol. Chem., 2014, vol. 12, No. 41, 8125-8127.
Bilyk et al., "Cloning and Heterologous Expression of the Grecocycline Biosynthetic Gene Cluster," PLoS One., 2016, 11, 7, 1-17.
Barry et al., "Cytochrome P450-catalyzed L-trypotphan Nitration in Thaxtomin Phytotoxin Biosynthesis," Nat. Chem. Biol., vol. 8, Oct. 2012, 814-816.
Leiner et al., "Probable Involvement of Thaxtomin A in Pathology of Streptomyces scabies in Seedlings," Phytopathology, 1996, vol. 86, No. 7, 709-713.
Johnson et al., "Cello-oligosaccharides Released from Host Plants Induce Pathology in Scab-causing *streptomyces* Species," Physiol Mol Plant Path., 2007, 71, 18-25.
Simon et al., "A Broad Host Range Mobilization System for In Vivo Genetic Engineering: Transposon Mutagenesis in Gram Negative Bacteria," Nat. Biotechnol., Nov. 1983, 1,784-791.

* cited by examiner $R_1$=OH, $R_2$=H, $R_3$=OH Thaxtomin A (1)
$R_1$=OH, $R_2$=OH, $R_3$=H *Ortho*-thaxtomin A (2)
$R_1$=H, $R_2$=H, $R_3$=H Thaxtomin D (3)

R=H 4-nitro-tryptophan (4)
R=Me *N*-methyl-4-nitrotryptophan (5)
R=Ac *N*-acetyl-4-nitrotryptophan (6)

GENETICALLY ENGINEERED *STREPTOMYCES* CAPABLE OF THAXTOMIN PRODUCTION IN THE ABSENCE OF THAXTOMIN-INDUCING CONDITIONS AND METHODS OF PRODUCING THAXTOMIN

CROSS-REFERENCE TO RELATED APPLICATIONS

This application is the 35 U.S.C. § 371 national stage application of PCT Application No. PCT/US2018/063130, filed Nov. 29, 2018, where the PCT claims priority to, and the benefit of, U.S. provisional patent No. 62/591,876 filed Nov. 29, 2017, both of which are herein incorporated by reference in their entireties.

SEQUENCE LISTING

This application contains a sequence listing filed in electronic form as an ASCII.txt file entitled 222110-2550_ST25.txt, created on Nov. 29, 2018 and having a size of 65 KB. The content of the sequence listing is incorporated herein in its entirety.

BACKGROUND

The thaxtomins are a group of phytotoxins generated by some species of *Streptomyces* bacteria, such as *Streptomyces scabiei*(the main causal organism of potato common scab). The thaxtomins can cause plant cell necrosis of various plant species and thus have broad spectrum herbicidal activity. These potent herbicidal activities, along with their environmentally benign and bio-degradable properties, make thaxtomins good green herbicides Five toxins, including thaxtomin A and thaxtomin B, that induce the formation of scabs on potato tubers have been isolated from *S. scabiei*, and as at least 11 thaxtomin analogs have also been isolated. They are cyclic dipeptides classed as 2,5-Diketopiperazines, with thaxtomin A, the most abundant, having the chemical formula $C_{22}H_{22}N_4O_6$. Individual thaxtomins appear to differ only in the presence or absence of N-methyl and hydroxyl groups and their respective substitution sites.

The genes involved in thaxtomin biosynthesis are located on a part of the genome called the pathogenicity island, present in the pathogenic *Streptomyces* strains, such as but not limited to, *S. scabiei, S. acidiscabies* and *S. turgidiscabies*. Although more than 800 *Streptomyces* species are known to date, only a small number of species have so far been known to be phytopathogenic (Loria et al. 2006). The best characterized pathogenic species are *S. scabiei, S. acidiscabies, S. turgidiscabies*, and *S. ipomoeae* (Loria et al. 2008).

Thaxtomins inhibit the synthesis of cellulose, the major component of the plant cell wall, and cause dramatic plant cell hypertrophy and seedling stunting at the nM level (Bischoff et al. 2009; Fry and Loria 2002; King et al. 2001). The attractive bioactivities of thaxtomins makes them desirable candidates for development and use as natural, commercial herbicides for weed control (Koivunen et al. 2013; Leep et al. 2010). However, the limited productivity of thaxtomins in existing *Streptomyces* species as well as limited ability for production on an industrial scale presents problems, such as slow production, low yields, and the need for certain inducers, which are all constraining factors for commercialization. For instance, several pathogenic *Streptomyces* strains are known to produce thaxtomins in the presence of cellobiose as the inducer. However, the productivity is generally in the several mg/L range, and the high cost of cellobiose further limits the applications of these strains in large-scale production of these herbicides.

SUMMARY

Briefly described, the present disclosure provides refactored thaxtomin biosynthetic gene clusters for enabling a transformed non-pathogenic bacterial cell to produce of thaxtomin A and/or other thaxtomin compound in the absence of thaxtomin-inducing conditions, such as cellobiose. The present disclosure also includes genetically engineered, non-pathogenic *Streptomyces* bacterium with exogenous, non-native thaxtomin biosynthetic gene clusters conferring the genetically engineered, non-pathogenic *Streptomyces* bacterium with the ability to produce thaxtomin compounds, derivatives, and intermediates in the absence of cellobiose. The present disclosure also includes methods of producing thaxtomin and thaxtomin intermediates and the thaxtomin and thaxtomin intermediate compounds produced by the methods of the present disclosure.

Embodiments of genetically engineered *Streptomyces* bacteria of the present disclosure include: a *Streptomyces* bacterium from a non-pathogenic *Streptomyces* strain, the *Streptomyces* bacterium comprising an exogenous, refactored thaxtomin biosynthetic gene cluster comprising at least two thaxtomin modules. In embodiments, each module includes one or more thaxtomin genes from a thaxtomin biosynthetic gene cluster from a pathogenic *Streptomyces* strain, and one or more promoters operably linked to the one or more thaxtomin genes. The at least two thaxtomin modules represent a refactored thaxtomin biosynthetic gene cluster such that expression of the refactored thaxtomin biosynthetic gene cluster provides the genetically engineered *Streptomyces* bacterium with the ability to produce at least one thaxtomin compound in the absence of thaxtomin-inducing conditions, where the non-pathogenic *Streptomyces* strain without the refactored thaxtomin cluster does not have the ability to produce the thaxtomin compound. In some embodiments described in the present disclosure, the at least two thaxtomin modules include a first module, module 1, including a txtE and a txtD biosynthetic gene and a second module, module 2, including a txtA, a txtB, and optionaly txtH biosynthetic gene.

Embodiments according to the present disclosure of a refactored thaxtomin biosynthetic gene cluster include: one or more thaxtomin modules, each module having at least the following: one or more thaxtomin genes from a thaxtomin biosynthetic gene cluster from a pathogenic *Streptomyces* bacteria, and one or more promoters operably linked to the one or more thaxtomin genes. The one or more thaxtomin modules form a refactored thaxtomin biosynthetic gene cluster such that expression of the refactored thaxtomin biosynthetic gene cluster produces at least one thaxtomin compound in the absence of thaxtomin-inducing conditions. In embodiments, if the thaxtomin biosynthetic gene cluster comprises only one thaxtomin module, that thaxtomin module comprises two or more thaxtomin genes.

The present disclosure also provides methods of providing a genetically engineered *Streptomyces* bacterium capable of producing thaxtomin compounds in the absence of thaxtomin-inducing conditions. In embodiments, such methods include: providing a *Streptomyces* bacterium from a naturally non-pathogenic species that does not produce thaxtomin; and genetically engineering the *Streptomyces* bacterium to include an exogenous, refactored thaxtomin biosynthetic gene cluster comprising one or more thaxtomin modules that form the refactored thaxtomin biosynthetic gene cluster. In such embodiments, each thaxtomin module includes: one or more thaxtomin genes from a thaxtomin biosynthetic gene cluster from a pathogenic *Streptomyces* bacteria, and one or more promoters operably linked to the one or more thaxtomin genes in the one or more modules, where the exogenous, refactored thaxtomin biosynthetic gene cluster provides the genetically engineered *Streptomyces* bacterium with the ability to produce at least one thaxtomin compound in the absence of thaxtomin-inducing conditions.

Embodiments of methods of producing a thaxtomin compound of the present disclosure include: culturing genetically engineered *Streptomyces* bacteria from a non-pathogenic *Streptomyces* strain in the absence of thaxtomin-inducing conditions, where the genetically engineered *Streptomyces* bacterium have an exogenous, refactored thaxtomin biosynthetic gene cluster including one or more thaxtomin modules, each module having one or more thaxtomin genes from a thaxtomin biosynthetic gene cluster from a pathogenic *Streptomyces* bacteria, and one or more promoters operably linked to the one or more thaxtomin genes. In such embodiments, the one or more thaxtomin modules form a refactored thaxtomin biosynthetic gene cluster such that expression of the refactored thaxtomin biosynthetic gene cluster provides the genetically engineered *Streptomyces* bacterium with the ability to produce at least one thaxtomin compound in the absence of thaxtomin-inducing conditions.

Methods of the present disclosure also include producing a thaxtomin compound analog or intermediate. In embodiments, such methods include: culturing genetically engineered *Streptomyces* bacteria from a non-pathogenic *Streptomyces* strain in the absence of thaxtomin-inducing conditions, the genetically engineered *Streptomyces* bacterium including an exogenous, refactored thaxtomin biosynthetic gene cluster comprising one or more thaxtomin modules, where the one or more thaxtomin modules include a txtE, a txtD a txtA, a txtB, and a txtH biosynthetic gene and one or more promoters operably linked to the biosynthetic genes. In embodiments, the biosynthetic gene cluster does not comprise a txtC biosynthetic gene, and the thaxtomin modules form a refactored thaxtomin biosynthetic gene cluster such that expression of the refactored thaxtomin biosynthetic gene cluster provides the genetically engineered *Streptomyces* bacterium with the ability to produce at least one thaxtomin compound analog or intermediate in the absence of thaxtomin-inducing conditions.

The present disclosure also includes embodiments of genetically engineered *Streptomyces* bacterium including: a *Streptomyces* bacterium from a non-pathogenic *Streptomyces* strain, the *Streptomyces* bacterium having an exogenous, refactored thaxtomin biosynthetic gene cluster comprising one or more thaxtomin modules. In such embodiments, each module includes one or more thaxtomin genes from a thaxtomin biosynthetic gene cluster from a plant pathogenic *Streptomyces* bacterium, where if the thaxtomin biosynthetic gene cluster comprises only one thaxtomin module, that thaxtomin module comprises two or more thaxtomin genes. Each module also includes one or more promoters operably linked to the one or more thaxtomin genes in the one or more thaxtomin modules, such that expression of the thaxtomin genes in the refactored thaxtomin biosynthetic gene cluster provides the genetically engineered *Streptomyces* bacterium with the ability to produce at least one thaxtomin compound in the absence of thaxtomin-inducing conditions, where the non-pathogenic *Streptomyces* strain without the refactored thaxtomin cluster does not have the ability to produce the thaxtomin compound.

Other systems, methods, features, and advantages of the present disclosure will be or will become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
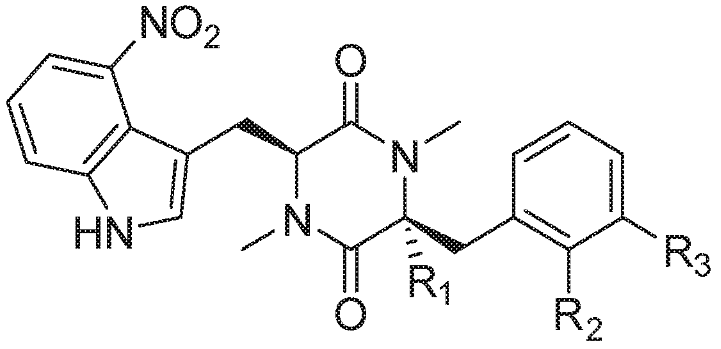
FIG. 1 illustrates the chemical structures of selected thaxtomins and nitro-tryptophan analogs.
Figure 1:
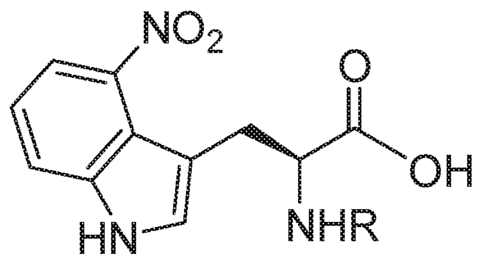

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, botany, biochemistry, biology, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

The terms "nucleic acid" and "polynucleotide" are terms that generally refer to a string of at least two base-sugar-phosphate combinations. As used herein, the terms include deoxyribonucleic acid (DNA) and ribonucleic acid (RNA) and generally refer to any polyribonucleotide or polydeoxyribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid sequence" and "oligonucleotide" also encompasses a nucleic acid and polynucleotide as defined above.

In addition, polynucleotide as used herein refers to double-stranded regions comprising RNA or DNA or both RNA and DNA. The strands in such regions may be from the same molecule or from different molecules. The regions may include all of one or more of the molecules, but more typically involve only a region of some of the molecules. One of the molecules of a double-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. The terms herein also include naturally occurring, chemically modified, and chemically synthesized DNA/RNA.

The term also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotides" as that term is intended herein.

A "gene" typically refers to a hereditary unit corresponding to a sequence of DNA that occupies a specific location on a chromosome and that contains the genetic instruction for a characteristic(s) or trait(s) in an organism.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome. A "transformed" cell is thus a cell transfected with a nucleic acid sequence. The term "transformation" refers to the introduction of a nucleic acid (e.g., DNA or RNA) into cells in such a way as to allow expression of the coding portions of the introduced nucleic acid.

As used herein, "transformation" or "transformed" refers to the introduction of a nucleic acid (e.g., DNA or RNA) into cells in such a way as to allow expression of the coding portions of the introduced nucleic acid.

As used herein a "transformed cell" is a cell transfected with a nucleic acid sequence. As used herein, a "transgene" refers to an artificial gene or portion thereof that is used to transform a cell of an organism, such as a bacterium or a plant.

As used herein, "transgenic" refers to a cell, tissue, or organism that contains a transgene.

As used herein, "exogenous nucleic acid sequence" or "exogenous polynucleotide" refers to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant, e.g., a "non-native" nucleic acid. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

The term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments)), the combination of a nucleic acid encoding a polypeptide to a promoter sequence, where the coding sequence and promoter sequence are from different sources or otherwise do not typically occur together naturally). Recombinant also refers to the polypeptide encoded by the recombinant nucleic acid. Non-naturally occurring nucleic acids or polypeptides include nucleic acids and polypeptides modified by man.

As used herein, "isolated" means removed or separated from the native environment. Therefore, isolated DNA can contain both coding (exon) and noncoding regions (introns) of a nucleotide sequence corresponding to a particular gene. An isolated peptide or protein indicates the protein is separated from its natural environment. Isolated nucleotide sequences and/or proteins are not necessarily purified. For instance, an isolated nucleotide or peptide may be included in a crude cellular extract or they may be subjected to additional purification and separation steps.

With respect to nucleotides, "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The term "polypeptides" and "protein" include proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

As used herein "functional variant" refers to a variant of a protein or polypeptide (e.g., a variant of a CCD enzyme) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

The term "expression" as used herein describes the process undergone by a structural gene to produce a polypeptide. It can refer to transcription or the combination of transcription and translation. Expression generally refers to the transcription of a gene to produce messenger RNA, as used herein expression may refer to the entire process of "expression" of a nucleic acid to produce a polypeptide (e.g., transcription plus translation). If "expression" is used in reference to a polypeptide, it indicates that the polypeptide is being produced via expression of the corresponding nucleic acid.

As used herein, the term "over-expression" and "up-regulation" or "increasing" production of a polypeptide refers to the expression of a nucleic acid encoding a polypeptide (e.g., a gene) in a modified cell at higher levels (therefore producing an increased amount of the polypeptide encoded by the gene) as compared to a "wild type" cell (e.g., a substantially equivalent cell that is not modified in the manner of the modified cell) under substantially similar conditions. Thus, to over-express or increase expression of thaxtomin refers to increasing or inducing the production of the thaxtomin dipeptide by one or more enzymes encoded by the thaxtomin biosynthetic genes, which may be done by a variety of approaches, such as, but not limited to: increasing the transcription of the genes (such as by placing the genes under the control of a constitutive promoter) responsible for synthesis of thaxtomin, or increasing the translation of such genes, inhibiting or eliminating a repressor of thaxtomin production (e.g., CebR or β-glucosidase enzyme), or a combination of these and/or other approaches.

Conversely, "under-expression" and "down-regulation" refers to expression of a polynucleotide (e.g., a gene) at lower levels (producing a decreased amount of the polypeptide encoded by the polynucleotide) than in a "wild type" cell. As with over-expression, under-expression can occur at different points in the expression pathway, such as by decreasing the number of gene copies encoding for the polypeptide; removing, interrupting, or inhibiting (e.g., decreasing or preventing) transcription and/or translation of the gene (e.g., by the use of antisense nucleotides, suppressors, knockouts, antagonists, etc.), or a combination of such approaches. "Suppression" refers to the inhibition of production and/or activity functional gene product. Thus, the suppression of a gene or protein may indicate that the expression of the gene and/or activity of the encoded peptide has been inhibited such as by transcription and/or translation being inhibited, thus resulting in low to no production of the encoded protein, or production of a non-functional product, or production of an interfering nucleic acid that otherwise suppresses activity of the target protein.

Similarly, with respect to a gene product, such as a protein, "reduced activity" indicates that the activity of the protein is reduced relative to activity in a "wild type cell". Such reduction in activity can be the result of inhibition/suppression/down-regulation/under-expression of the gene encoding the protein, the result of inhibition of translation of the messenger RNA into a functional gene product, or the result of production of a non-functional protein with reduced or no activity, or the direct suppression of the protein activity (e.g., preventing binding to a target), or the like. "Reduced production" of a gene product (e.g., a protein), such as by suppression, interruption, or other inhibition of transcription or translation, may result in reduced activity, but "reduced activity" of a protein or other gene product may result from other causes other than "reduced production", such as set for the above.

As used herein, the term "genetically engineered," with respect to a living organism, refers to an organism that has had its genetic makeup directly manipulated by techniques of biotechnology (as opposed to random changes occurring in nature). Genetically engineered organisms can include mutations involving changes only of the genetically engineered organisms' own genetic material as well as mutations involving insertions of exogenous genetic material, such as insertions resulting in either cisgenic (including exogenous genetic material from the same or a closely related organism) or transgenic (including exogenous genetic material from a non-closely related organism) organisms.

As used herein a "mutation" refers to a heritable change in genetic material, which may include alteration of single base pairs of a nucleic acid, or the deletion, insertion, or rearrangement of larger sections of genes or chromosomes. An "engineered mutation" refers to a mutation created by human design (e.g., the mutation did not spontaneously occur by natural causes and/or was the result of intentional human manipulation). A "genetically modified" organism is an organism whose genetic material has been altered by one or more engineered mutations (e.g., human induced mutations).

Similarly, with respect to genes or other nucleic acids, "silencing" or "deletion" of a gene may include complete deletion of the nucleic acid/gene encoding a target peptide, complete suppression of translation or transcription of the target nucleic acid such that the target peptide is not produced, but the terms may also include some of the methods for "suppression" and "down-regulation" discussed above, where the "suppression" is significant enough to reduce expression of the target gene to the extent that the resulting peptide is inactive or the activity of the resulting peptide is so minimal as to be virtually undetected.

The term "null mutation" refers to a mutation in which the gene product (e.g., the protein encoded by the gene) is either not produced (or produced at significantly reduced levels, so as to be negligible) or is non-functional. Typically, a null mutation will involve a mutation of the native gene, such that the gene is not transcribed into RNA, the RNA product cannot be translated, or the protein produced by gene expression is non-functional.

The term "plasmid" as used herein refers to a non-chromosomal double-stranded DNA sequence including an intact "replicon" such that the plasmid is replicated in a host cell. A plasmid may include exogenous nucleic acid sequences and/or recombinant sequences.

As used herein, the term "vector" or "expression vector" is used in reference to a vehicle used to introduce an exogenous nucleic acid sequence into a cell. A vector may include a DNA molecule, linear or circular, which includes a segment encoding a polypeptide of interest operably linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. As such, expression vectors typically contain recombinant nucleic acid sequences having different sequences linked together to effect expression of a target sequence. Expression vectors are generally derived from yeast DNA, bacterial genomic or plasmid DNA, or viral DNA, or may contain elements of more than one of these.

As used herein, the term "expression system" includes a biologic system (e.g., a cell based system) used to express a polynucleotide to produce a protein. Such systems generally employ a plasmid or vector including the polynucleotide of interest (e.g., an exogenous nucleic acid sequence, a recombinant sequence, etc.), where the plasmid or expression vector is constructed with various elements (e.g., promoters, selectable markers, etc.) to enable expression of the protein product from the polynucleotide. Expression systems use the host system/host cell transcription and translation mechanisms to express the product protein. Common expression systems include, but are not limited to, bacterial expression systems (e.g., *E. coli*), yeast expression systems, viral expression systems, animal expression systems, and plant expression systems.

As used herein, the term "promoter" or "promoter region" includes all sequences capable of driving transcription of a coding sequence. In particular, the term "promoter" as used herein refers to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

The term "operably linked" indicates that the regulatory sequences necessary for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, the term "selectable marker" refers to a gene whose expression allows one to identify cells that have been transformed or transfected with a vector containing the marker gene (e.g., by antibiotic resistance on antibiotic medium, fluorescence, color generation, or other detectable signal). For instance, a recombinant nucleic acid may include a selectable marker operably linked to a gene of interest and a promoter, such that expression of the selectable marker indicates the successful transformation of the cell with the gene of interest.

The terms "native," "wild type", or "unmodified" in reference to a polypeptide/protein/enzyme, polynucleotide, cell, or organism, are used herein to provide a reference point for a variant/mutant of a polypeptide/protein/enzyme, polynucleotide, cell, or organism prior to its mutation and/or modification/engineering (whether the mutation and/or modification occurred naturally or by human design). On the other hand, "non-native" refers to a polypeptide/protein/enzyme, polynucleotide, cell, or organism that has a sequence or feature not found naturally in that peptide/cell/organism/etc., but that has been genetically engineered/manipulated to have such non-native feature.

As used herein, "thaxtomin" or "thaxtomin compound" refers to one or more compounds from a family of cyclic dipeptide phytotoxins, 4-nitroindol-3-yl-containing 2,5-dioxopiperazines, generated by some species of *Streptomyces* bacteria (and possibly by other actinomycetes) and exhibiting toxicity to various plant species. Thaxtomin compounds of the present disclosure have the general formula of Formula I below, and variants thereof. At least 5 thaxtomin compounds have been characterized, including thaxtomin A, A ortho analog, B, C, and D, and up to at least 12 different variants identified. Thaxtomin A, the most abundant of the thaxtomins and also believed to be the most physiologically active, has the chemical formula $C_{22}H_{22}N_4O_6$ (chemical structure illustrated in FIG. 1). The thaxtomins can cause plant cell necrosis of various plant species and can induce the formation of scabs on potato tubers have been isolated from *S. scabiei*. As used herein "thaxtomin" and "thaxtomin compound" refers generally to any of the members of this chemical group. Much of the discussion of thaxtomin in the present disclosure is in reference to thaxtomin A; however, thaxtomin A may be a precursor to other thaxtomin compounds, and/or the production of thaxtomin A may be interwoven with production of other thaxtomin compounds. Thus, to the extent the methods and compositions of the present disclosure also modulate the production of other thaxtomin compounds or intermediates, this is also intended to fall within the scope of the present disclosure. The general structure of thaxtomin compounds is illustrated in FIG. 1 and the general formula of the family of thaxtomin compounds is shown below as Formula I, where R1 and R3 are independently selected from methyl or H and where R2, R4, R5, and R6 are each independently selected from hydroxyl or H.

Formula 1

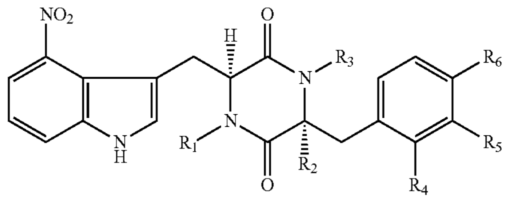

The term "thaxtomin biosynthetic gene cluster" (sometimes also referred to herein as "Thaxtomin A or ThxA gene cluster") refers to a gene cluster responsible for production of thaxtomins, such as thaxtomin A (ThxA), by an organism. The thaxtomin biosynthetic gene cluster occurs naturally in some pathogenic *Streptomyces* species, such as *S. scabiei*. In pathogenic *Streptomyces* species, the thaxtomin gene cluster includes genes involved in ThxA production (referred to herein as "thaxtomin genes"), such as, but not limited to, TxtA (SEQ ID NO: 1), TxtB (SEQ ID NO: 3), TxtC (SEQ ID NO: 5), TxtD (SEQ ID NO: 7), TxtE (SEQ ID NO: 9), TxtH (SEQ ID NO: 11), TxtR (SEQ ID NO: 13), which encode the peptides TxtA (SEQ ID NO: 2), TxtB (SEQ ID NO: 4), TxtC (SEQ ID NO: 6), TxtD (SEQ ID NO: 8), TxtE (SEQ ID NO: 10), TxtH (SEQ ID NO: 12), and TxtR (SEQ ID NO: 14), respectively). The sequences listed above are from *Streptomyces scabiei* and are representative of the ThxA genes of pathogenic *Streptomyces* species; however, the genes encoding the thaxtomin peptides may vary in different species or in synthetic variants. Thus, in the present disclosure, the genes involved in production of thaxtomin A and the encoded peptides in different species as well as completely synthesized genes/peptides are also intended to be included in the scope of the disclosure, such as polynucleotide sequences having sequence similarity with the sequences above from *Streptomyces scabiei* and still having the same function (e.g., sequences having about 70% or greater, 80% or greater, 90% or greater, 95% or greater, 99% or greater sequence identity with SEQ ID Nos: 1, 3, 5, 7, 9, 11, and 13) and peptide sequences having sequence identity with the peptide sequences from *Streptomyces scabiei* and still having the same function (e.g., sequences having about 70% or greater, 80% or greater, 90% or greater, 95% or greater, 99% or greater sequence identity with SEQ ID Nos: 2, 4, 6, 8, 10, 12, and 14).

The ThxA gene cluster of the present disclosure may include all of the above thaxtomin genes or any subset/variant of these needed to confer a recipient organism with the ability to produce thaxtomin.

In the present disclosure, the term "thaxtomin module" refers to specifically designed groupings of one or more thaxtomin genes (e.g., txtA, txtB) from the thaxtomin gene cluster, where the genes have been regrouped, or "refactored", such that the thaxtomin genes have been placed under the control (e.g., operably linked) of a promoter that does not require thaxtomin-inducing conditions (e.g., presence of cellobiose or other conventional thaxtomin inducer) to induce expression of the operably linked gene or genes. The regrouping can be such that each gene is in a separate module, or that some or all thaxtomin genes are grouped on a single module, or that the genes are re-grouped on two or more modules. Various configurations of thaxtomin genes and promoters, among one or more modules, are envisioned within the scope of this disclosure. For example, in embodiments, each module is placed under the control of a separate promoter, but in other embodiments, each module may include one or more promoters, each gene may be operably linked to a separate promoter, or all genes and modules may be linked to the same promoter, and the like. For instance, in some embodiments discussed below, several genes from the thaxtomin biosynthetic gene cluster were refactored (e.g., rearranged/regrouped) into 3 different functionally distinct modules, and each module was separately controlled by its own promoter. As used herein, the terms "module 1," "module 2," and "module 3" refer to refactored gene clusters from the thaxtomin gene cluster. In embodiments, module 1 includes txtE and txtD; module 2 includes txt A, txtB, and txtH; module 3 includes txtC; and each module is under the control of a separate promoter. In some embodiments, module 1 includes txtE and txtD; module 2 includes txt A and txtB; module 3 includes txtC; and each module is under the control of a separate promoter. The new modules can be joined together to form a partial or complete "refactored thaxtomin gene cluster" (e.g., in the refactored thaxtomin gene cluster, the genes can be in a different order than in the native thaxtomin gene cluster and are under different controls than in the native gene cluster).

The term "toxogenic region (TR)", refers to a mobile genomic island in some *Streptomyces* species that can include "toxogenic region 1 (TR1)", that includes the thaxtomin A biosynthetic cluster, described above, and typically confers pathogenicity, and also includes "toxogenic region 2 (TR2)" that includes integrative and conjugative elements that can mobilize itself (TR2) or an entire TR element (e.g., TR1 and TR2) between species (e.g., between pathogenic and non-pathogenic species) as described in greater detail below).

The terms "thaxtomin-inducing conditions" indicates certain environmental conditions (e.g., natural or cell culture conditions) known to induce thaxtomin production in wild-type *Streptomyces* bacterial species known to be capable of thaxtomin production (e.g., native thaxtomin producers). For instance, wild type *Streptomyces* are induced to produce thaxtomin in the presence of certain products of cellulose degradation, such as, but not limited to, cellobiose, as well as xylan-degradation products (Wach et al. 2007), such as, but not limited to suberin (Lauzier et al. 2008). In embodiments, "thaxtomin-inducing conditions" may include specific conditions or cell culture media (such as but not limited to, Oat Bran Broth (OBB), Oat Bran Agar (OBA), etc.) known to induce thaxtomin production in cell culture of wild-type *Streptomyces* species (such as, but not limited to *S. scabiei, S. acidiscabies*, and *S. turgidiscabies*). In embodiments, "thaxtomin-inducing conditions" may also include a standard cell culture growth medium supplemented with a known thaxtomin-inducing compound, such as, but not limited to cellobiose.

Discussion

In accordance with the purpose(s) of the present disclosure, as embodied and broadly described herein, embodiments of the present disclosure, in some aspects, relate to genetically engineered *Streptomyces* bacteria from a naturally non-pathogenic *Streptomyces* species capable of increased thaxtomin production, genetically engineered *Streptomyces* bacteria with non-native thaxtomin pathogenicity clusters capable of producing thaxtomin in the absence of the inducer cellobiose and capable of producing the same or a greater amount of thaxtomin than *S. scabiei*, under the same conditions, and thaxtomin and thaxtomin intermediates produced by the methods of the present disclosure.

Herbicides play an important role in agricultural production all over the world. However, wide applications of various herbicides have incurred herbicide resistance among weeds. Regardless of the need for new herbicides with new mechanisms of action, no herbicides acting on new targets have been commercialized in recent decades. It is therefore important to develop new herbicides with novel modes of action. One potential source of new herbicides is phytopathogenic bacterial species.

*Streptomyces* is a very large genus of filamentous Gram-positive, high G+C content bacteria that are mostly saprophytes and best known for the production of pharmaceutically- and agriculturally-important secondary metabolites, including two-thirds of currently-used antibiotics (Hopwood 2007, Bentley et al. 2002). Although several hundred species are known to date, only about ten are known to be phytopathogenic (Loria et al. 2006). The best characterized pathogens are *Streptomyces scabiei, S. acidiscabies, S. turgidiscabies* and *S. ipomoeae*, which cause raised or pitted scab lesions on economically-important root and tuber crops like potato, radish, beet, peanut, and sweet potato, but not rice. The primary virulence determinant of *S. scabiei, S. acidiscabies* and *S. turgidiscabies* is the phytotoxin thaxtomin A (Loria et al. 2008). Thaxtomin A (compound 1, FIG. 1) was initially isolated in 1989 and is the most abundant member of the family that comprises 10 other natural analogs (FIG. 1). Thaxtomin A (1) exhibits excellent potency (in an nM range) in inhibiting cellulose biosynthesis.

Thaxtomin A (and other toxic thaxtomin compounds) primarily targets the cell wall in dividing and expanding plant cells through an alteration of expression of cell wall biosynthesis-related genes and depletion of cellulose synthase complexes from the plasma membrane. This causes extensive cell wall remodeling, characterized by reduced incorporation of crystalline cellulose into the plant cell wall, and is compensated by an increased amount of pectins and hemicelluloses (Scheible et al. 2003; Bischoff et al. 2009). Thaxtomin A's herbicidal mode and biodegradable property have led to extensive attention to develop thaxtomins as novel green herbicides. It is member of a family of nitrated 2,5-diketopiperazines formed by non-ribosomal peptide synthases out of the main components tryptophan, phenylalanine and nitric oxide derived from arginine (Loria et al. 2008; Barry et al. 2012), with 11 members of the family differing only in the presence or absence of hydroxyl and N-methyl groups at specific sites. FIG. 1 illustrates the structure of thaxtomin A as well as other thaxtomin analogues.

The biosynthesis of ThxA involves two nonribosomal peptide synthetases (NRPSs) encoded by the txtA and txtB genes, a P450 monooxygenase (TxtC), a nitric oxide synthase (TxtD), and a novel cytochrome P450 (TxtE) that site specifically nitrates tryptophan prior to cyclization (Bignell et al. 2014b). The thaxtomin biosynthetic cluster also contains a txtH gene encoding a 65-amino-acid MbtH-like protein potentially regulating NRPS activity (Herbst et al. 2013; Stegmann et al. 2006). The production of thaxtomin A is typically under strict controls, including both the pathway-specific transcriptional activator TxtR (Joshi et al. 2007) and global regulators belonging to the bld gene family (Bignell et al. 2014a) and the cellulose utilization repressor CebR (Francis et al. 2015). This group of genes, called the thaxtomin A biosynthetic gene cluster, resides on a portion of a mobile genomic island in pathogenic *Streptomyces* species, known as toxogenic region 1 (TR1). Many *Streptomyces* species also include another toxogenic region (TR2) that has integrative and conjunctive elements and has the ability to mobilize TR2 alone or the whole TR element between *Streptomyces* species as described in Zhang & Loria 2016 ("Emergence of Novel Pathogenic *Streptomyces* Species by Site-Specific Accretion and cis-Mobilization of Pathogenicity Islands", December 2016) and Zhang, et al. 2016 ("Promiscuous Pathogenicity Islands and Phylogeny of Pathogenic *Streptomyces* spp." July 2016), both of which are hereby incorporated by reference herein in their entirety.

Data have shown that thaxtomin provokes the same effects on plants, qualitatively as well as quantitatively, as the synthetic cellulose biosynthesis inhibitor isoxaben, making thaxtomin an excellent candidate as a natural herbicide (Heim et al. 1990; Bischoff et al. 2009). The biological properties of this novel phytotoxin raised an interest in using thaxtomin as a biological compound to control weeds (Marrone Bio Innovations 2009, 2010; Novozymes Biologicals 2011, 2012). However, thaxtomin production in wild type *Streptomyces* requires specialized cell culture media (such as media supplemented with cellobiose or other thaxtomin-inducing compounds), which can be expensive. Several chemical methods have also been investigated to synthesize thaxtomins using multiple steps with mild to moderate yields. (see King, R. R. 1997; Molesworth, P. et al., 2010, Zhang, H., et al., 2013; and Zhang, et al., 2015.) For instance, the Ugi reaction was used to synthesize thaxtomin A in a one-pot reaction (Bourgault, J. P., et al., 2014), but only a racemic mixture that contains both enantiomers was obtained.

*Streptomyces scabies* is the best studied producer of thaxtomins. However, the isolation yield of thaxtomin A from its culture is as low as several mg/L in cellobiose-containing liquid media even after extensive optimization efforts, which severely limits the wide application of thaxtomins in agriculture. Thus, these methods of production of thaxtomin in wild type *Steptomyces*, such as *S. scabiei*, are insufficient. The authors of the present disclosure previously demonstrated mobilization of the thaxtomin biosynthetic cluster of *S. scabiei* into non-pathogenic *Streptomyces* species to enable the heterologous production of thaxtomin in the non-pathogenic species, which is described in greater detail in U.S. provisional patent application No. 62/509,792, which is hereby incorporated by reference in its entirety. Many of the recipient *Streptomyces* spp. that produced thaxtomin upon the acquisition of the thaxtomin cluster produced it in the same or lower amounts than *S. scabiei*, indicating that the genetic backgrounds of recipients affect the thaxtomin production considerably. However, at least one strain, *S. albus* J1074, when engineered to include the thaxtomin biosynthetic cluster from *S. scabiei*, produced the same or greater amounts of thaxtomins in comparison to *S. scabiei*. However, even these methods of production of thaxtomins in the non-native, non-pathogenic *Streptomyces* species by acquisition of the thaxtomin biosynthetic gene cluster still require the presence of specialized growth media with expensive inducers, such as cellobiose, to achieve a significant yield.

The present disclosure provides genetically engineered, non-native *Streptomyces* bacteria with the ability to produce thaxtomin compounds in species that do not naturally produce thaxtomin and are not naturally pathogenic to plants, where thaxtomin is produced without the need for costly inducers, such as cellobiose. In embodiments, the present disclosure provides genetically engineered bacteria capable of producing thaxtomin without cellobiose as well as methods to produce thaxtomin in non-native species and at greater amounts than in wild type, native, thaxtomin-producing *Steptomyces*, such as *S. scabiei*, as well as methods for producing thaxtomin using such genetically modified bacteria.

As mentioned above, the biosynthetic gene cluster of thaxtomin includes seven genes (txtA, txtB, txtC, txtD, txtE, txtH, and txtR, e.g., SEQ ID NOs: 1, 3, 5, 7, 9, 11, and 13, respectively) encoding the following 7 proteins: two P450s (TxtC and TxtE, e.g., SEQ ID NOs: 6 and 10, respectively), two nonribosomal peptide synthetases (TxtA and TxtB, e.g., SEQ ID NOs: 2 and 4, respectively), one MbtH-like protein (TxtH, e.g., SEQ ID NO: 12), one positive regulator (TxtR, e.g., SEQ ID NO: 14) and one nitric oxide synthase (TxtD, e.g., SEQ ID NO: 8). The systems and methods of the present disclosure include refactoring the thaxtomin gene cluster, or portions of this cluster, into one or more modules under the control of one or more promoters that are not under the control of a natural thaxtomin inducer, such as, but not limited to cellobiose. In the present disclosure, the one or more promoters controlling expression of one or more thaxtomin genes in the refactored thaxtomin gene cluster can be but are not limited to, constitutive promoters or inducible promoters, where such inducible promoters are induced by compounds that are more readily available and/or less expensive than conventional thaxtomin inducers, such as cellobiose.

Figure 2:
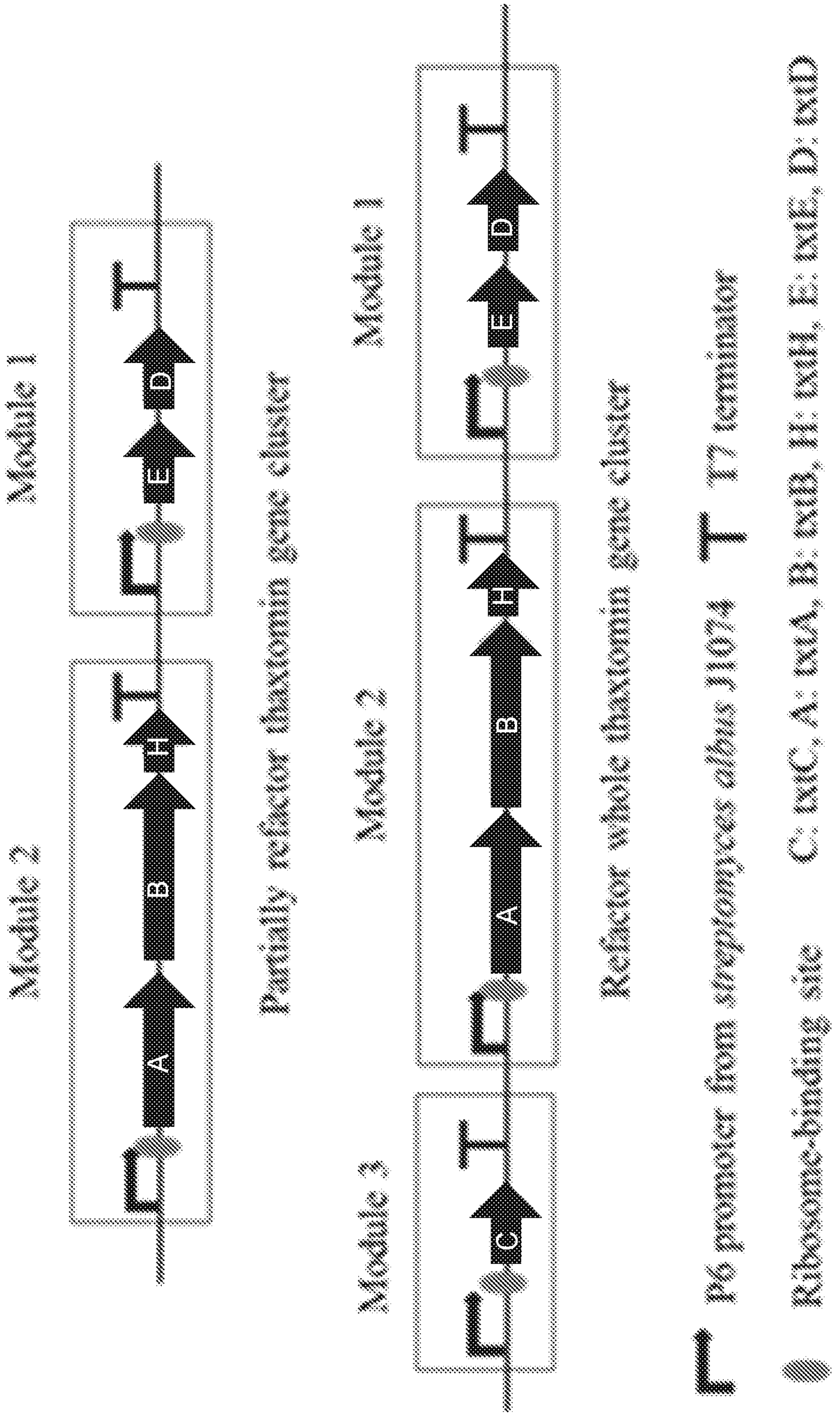
FIG. 2 illustrates partial and complete refactored gene clusters of thaxtomin.
Figure 7A:
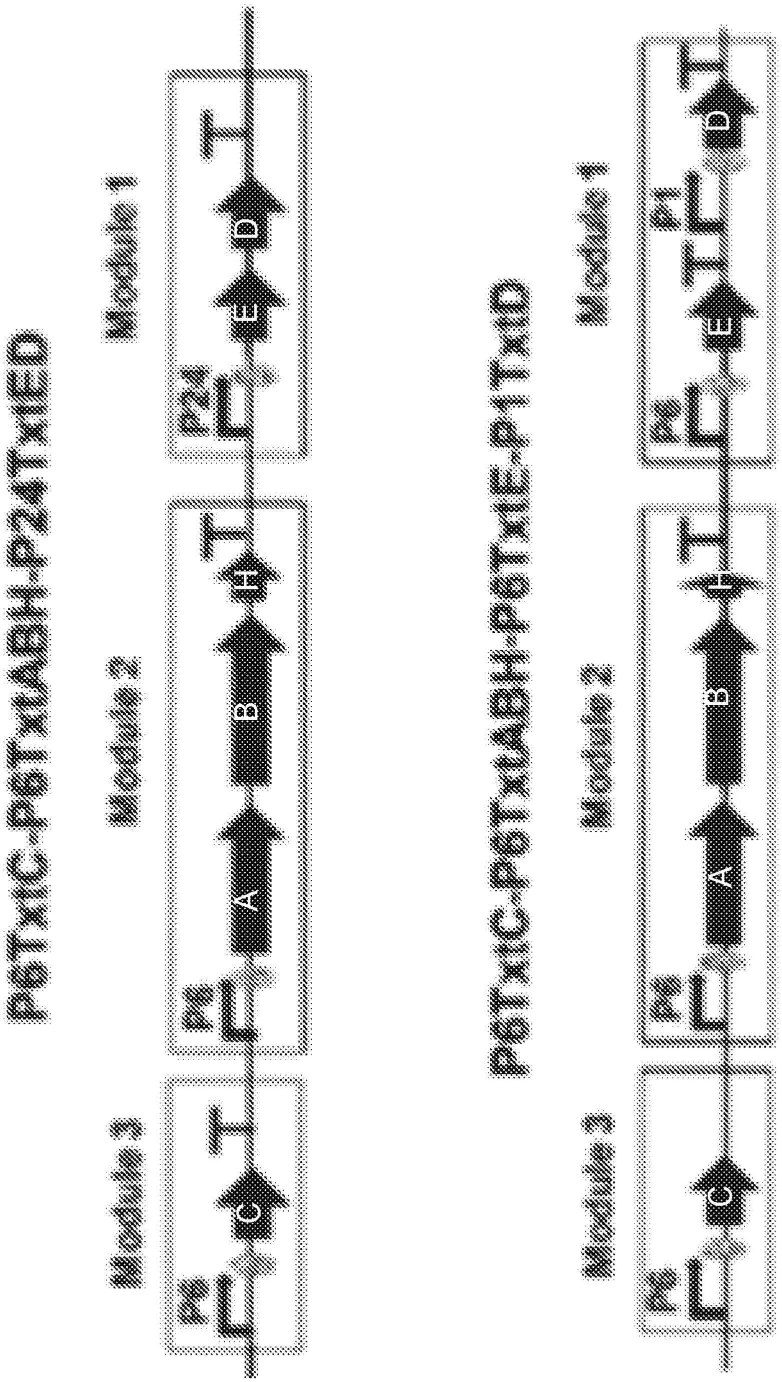
FIG. 7A is a schematic illustration of embodiments of two refactored biosynthetic thaxtomin gene clusters according to the present disclosure.

As described in greater detail in the Examples below, in an embodiment, this gene cluster was refactored into three functionally distinct modules, and the expression of each module was individually controlled by one or more separate promoters, as illustrated in FIG. 2 and FIG. 7A. The modules were used to transform (e.g., in a plasmid or other transformation vector) a non-pathogenic *Streptomyces* strain which was then screened for expression of thaxtomins from the refactored gene cluster. Many *Streptomyces* strains, such as, for example, *S. albus* J1074, have demonstrated the capability to express heterologous gene clusters of natural products and can be suitable for the production of thaxtomins from the refactored gene cluster. *S. albus* J1074 has been used as a synthetic biology chassis to express natural product gene clusters from other gram-positive actinomycetes and contains ferredoxin and ferredoxin reductase to support the reactions of P450s. (see, e.g., Zaburannyi, N., et al., 2014; Bilyk, O., et al., 2016; and Feng, Z. et al., 2009).

Thus, as described in more detail in the discussion and the examples below, the present disclosure includes genetically engineered *Streptomyces* bacterium from non-pathogenic species that have been genetically engineered to express an exogenous, refactored thaxtomin gene cluster from a pathogenic *Streptomyces* strain and are capable of producing thaxtomin A in the absence of conventional thaxtomin-inducing conditions (e.g., cellobiose-containing media). Also provided are refactored thaxtomin gene clusters capable of providing a transformed non-pathogenic *Streptomyces* cell with the ability to produce thaxtomin A in the absence of thaxtomin-inducing conditions. The present disclosure also provides methods of providing cellobiose-independent thaxtomin-producing capability in non-native *Streptomyces* bacterium that are naturally non-pathogenic, and methods of making the genetically engineered *Streptomyces* bacterium. Additionally, the present disclosure provides methods of producing thaxtomin compounds by culturing the genetically engineered *Streptomyces* bacteria of the present disclosure in cellobiose-free media.

Refactored Thaxtomin Biosynthetic Gene Cluster

Embodiments of the present disclosure include a refactored thaxtomin biosynthetic gene cluster for enabling a transformed bacterial cell to produce generous amounts of thaxtomin A and/or other thaxtomin compound in the absence of thaxtomin-inducing conditions like expensive inducers, such as cellobiose. In embodiments, refactored thaxtomin biosynthetic gene clusters of the present disclosure include one or more thaxtomin modules under the control of one or more promoters that do not require thaxtomin-inducing conditions (e.g., conditions known to induce thaxtomin production in native producers). If there are more than one module, they may be, but are not required to be, physically linked together. There is no absolute need to directly link two modules together. In this regard, the modules can be expressed in different vectors, or be integrated into different locations of the bacterial chromosome. Whether or not the modules are physically linked and under the control of the same or different or multiple promoters, together the modules form the refactored thaxtomin biosynthetic gene cluster. Each thaxtomin module includes one or more thaxtomin genes from a thaxtomin biosynthetic gene cluster from a pathogenic *Streptomyces* bacteria. For instance, each module may include, but is not necessarily limited to, one or more (but not necessarily all) of the following thaxtomin genes: txtA, txtB, txtC, txtD, txtE, and txt H. The thaxtomin genes in the modules for the refactored thaxtomin gene cluster may be isolated from a thaxtomin-producing organism or they may be partially or completely chemically synthesized. In embodiments, the thaxtomin genes may include one or more of the following sequences: SEQ ID NOs: 1, 3, 5, 7, 9, 11, and 13. In some embodiments, the thaxtomin genes from each module are different from the other module, such that together the modules do not contain multiple copies of thaxtomin genes. However, in other embodiments, multiple copies of one or more of the above thaxtomin genes may be included in the one or more modules in order to increase gene dosage such that there is higher production of that thaxtomin compound.

In embodiments, the thaxtomin genes are included in the modules, or the refactored gene cluster as a whole, in a different order than in a wild type thaxtomin producing bacterium, such as *S. scabiei*. In embodiments, each module has its own promoter operably linked to the one or more thaxtomin genes, so that each module is under independent control of a separate promoter. In other embodiments, each module can be controlled by more than one promoter and/or if more than one thaxtomin gene is in the module, expression of each thaxtomin gene in the module may be under the control of the same promoter, or each may be under the control of a different promoter. For instance, the thaxtomin gene clusters illustrated in FIG. 2 and the top gene cluster in FIG. 7A illustrate 2 or 3 linked thaxtomin, where each module is under the control of a different promoter. The bottom refactored gene cluster in FIG. 7A illustrates 3 modules, where module 3 and module 2 are each under control of a separate promoter, and module 3 has two promoters, each driving expression of a different thaxtomin gene within the module. In yet other embodiments, the modules may be linked together and all under the combined control of a single promoter. Thus various combinations of modules and promoters are envisioned, so long as the thaxtomin genes in the resulting refactored thaxtomin gene cluster can be expressed in the absence of thaxtomin-inducing conditions (such as, but not limited to, the presence of cellobiose). The promoter for each module can be the same promoter or different. In embodiments, a constitutive promoter is used for one or more of the thaxtomin modules.

In embodiments, each promoter is independently selected from promoters including, but not limited to: P1, P6, P7, P8, P9, P10, P11, P13, P20, P23, P24, P28, P31, Ksaop*, and P6E-PID (SEQ ID NOs: 15-29, respectively). In embodiments, the promoter is P6 (SEQ ID NO: 16), P24 (SEQ ID NO: 25), or P1 (SEQ ID NO: 15) promoter from *S. albus* J1074, or a combination thereof. In embodiments, the promoters can be selected from promoters having sequence similarity with the sequences SEQ ID NOs: 15-29 from *Streptomyces albus* J1074 and still having the same function (e.g., sequences having about 70% or greater, 80% or greater, 90% or greater, 95% or greater, 99% or greater sequence identity with SEQ ID NOs: 15-29).

FIG. 2 illustrates embodiments of two refactored thaxtomin biosynthetic gene clusters of the present disclosure, one including 3 modules, which together include the thaxtomin biosynthetic genes txtA, txtB, txtC, txtD, txtE, and txtH (not in that order), and the other module including two modules and lacking the thaxtomin biosynthetic gene txtC. In FIG. 2, module 1 includes txtE and txtD, module 2 includes txtA, txtB, and txtH, and module 2 includes txtC. In another embodiment illustrated in FIG. 2, a refactored thaxtomin gene cluster includes only modules 1 and 2 and excludes module 3, thereby excluding txtC (this embodiment is sometimes referred to herein as a "partially refactored thaxtomin gene cluster"). Similarly, in FIG. 7A, refactored thaxtomin biosynthetic gene clusters include module 1 including txtE and txtD, module 2 including txtA, txtB, and txtH, and module 2 including txtC. In the embodiments illustrated in FIG. 2 and FIG. 7A each module is under the control of at least one promoter, where each promoter may be the same or different. In embodiments, a refactored thaxtomin biosynthetic gene cluster of the present disclosure includes at least two thaxtomin modules: a first module, module 1, including a txtE and a txtD biosynthetic gene and a second module, module 2, including a txtA, a txtB, and txtH biosynthetic gene. In some embodiments, the refactored thaxtomin biosynthetic gene cluster of the present disclosure includes a third module, module 3, comprising a txtC biosynthetic gene.

In embodiments of the refactored thaxtomin biosynthetic gene clusters of the present disclosure, at least two thaxtomin modules are linked to form a refactored thaxtomin biosynthetic gene cluster such that expression of the refactored thaxtomin biosynthetic gene cluster produces at least one thaxtomin compound in the absence of thaxtomin-inducing conditions. The independent promoters for each module are not dependent on induction by thaxtomin inducers (e.g., cellobiose) and are thus able to induce thaxtomin production without the presence of such inducers. In embodiments, the promoters may be constitutive promoters or may be specifically inducible promoters, where promotion is induced by an activity or compound other than one conventionally associated with thaxtomin induction.

In embodiments, the expression of a refactored thaxtomin biosynthetic gene cluster of the present disclosure produces at least one thaxtomin compound in the absence of thaxtomin-inducing conditions. In embodiments, the thaxtomin compound includes thaxtomin A. In embodiments, the thaxtomin compound includes ortho-thaxtomin A or other intermediates or analogs of thaxtomin A, such as thaxtomin D (see FIG. 1). In some embodiments, an intermediate or analog of thaxtomin A includes compounds such as illustrated in FIG. 1, including, but not limited to: thaxtomin D, nitro-tryptophans such as 4-nitro-tryptophan, N-methyl-4-nitrotryptophan, and N-acetyl-4-nitrotryptophan. The present disclosure also includes plasmids or other transformation vectors including the refactored thaxtomin biosynthetic gene cluster of the present disclosure.

Genetically Modified Bacteria

Embodiments of the present disclosure include genetically engineered *Streptomyces* bacterium including a *Streptomyces* bacterium from a non-pathogenic *Streptomyces* strain (e.g., *Streptomyces* strain that, in its native, unmodified form, does not produce thaxtomin and is not pathogenic to plants), that has been engineered to have and express an exogenous, refactored thaxtomin biosynthetic gene cluster of the present disclosure such that the refactored thaxtomin biosynthetic gene cluster provides the genetically engineered *Streptomyces* bacterium with the ability to produce at least one thaxtomin compound in the absence of thaxtomin-inducing conditions. As discussed above, refactored thaxtomin biosynthetic gene clusters of the present disclosure include one or more thaxtomin modules, each module including one or more thaxtomin genes from a thaxtomin biosynthetic gene cluster from a pathogenic *Streptomyces* bacteria, and one or more promoters, as described above. In embodiments, the refactored thaxtomin biosynthetic gene cluster of genetically engineered *Streptomyces* bacterium include two or more thaxtomin modules, and the thaxtomin genes in each module are different from the thaxtomin genes in the other module(s). In embodiments, each module has its own promoter and is independently controlled, and the promoter for each module may be the same or different (e.g., both may be constitutive promoters (same or different type), one may be constitutive and one may be inducible, both may be inducible, etc.).

The presence of the refactored thaxtomin biosynthetic gene cluster in the modified genome of the genetically engineered *Streptomyces* bacterium provides the naturally non-pathogenic strain with the ability to produce one or more thaxtomin compounds (e.g., thaxtomin A), unlike corresponding wild type strains of the bacterium. The refactored thaxtomin biosynthetic gene cluster is configured such that expression provides the genetically engineered *Streptomyces* bacterium not only with the ability to produce the desired thaxtomin compound(s), but to produce them in the absence of conventional thaxtomin-inducing conditions (e.g., cellobiose-containing media). Thus, although a wild-type version of this non-pathogenic *Streptomyces* strain without the exogenous refactored thaxtomin biosynthetic gene cluster does not have the ability to produce thaxtomin, with or without inducers, the genetically engineered strain that harbors the refactored thaxtomin biosynthetic gene cluster, can express the thaxtomin genes in the absence of thaxtomin-inducing conditions and thus produce thaxtomin compounds.

In embodiments, the genetically engineered *Streptomyces* bacterium produces about the same or a greater amount of thaxtomin in the absence of thaxtomin-inducing conditions than *S. scabiei* produces in the presence of thaxtomin-inducing conditions. Thus, in some conditions the genetically engineered *Streptomyces* bacterium of the present disclosure "overproduces" thaxtomin, as compared to a wild-type, thaxtomin producing, pathogenic species, such as *S. scabiei*.

In embodiments, thaxtomin-inducing conditions include conditions conventionally known to induce thaxtomin production and/or expression of genes in the thaxtomin production pathway. In embodiments thaxtomin-inducing conditions include the presence of certain inducers, such as, but not limited to, cellobiose, other cellulose degradation products, suberin, and other xylan-degradation products. In embodiments, thaxtomin-inducing conditions can also include cell culture media known to induce thaxtomin production in pathogenic *Streptomyces* strains such as but not limited to, Oat Bran Broth (OBB) and Oat Bran Agar (OBA), etc. In embodiments, thaxtomin inducing conditions include media containing cellobiose, suberin, or other thaxtomin inducer. In embodiments, the absence of thaxtomin-inducing conditions refers to the absence of cellobiose or other inducer in the culture media of the cells.

In embodiments the thaxtomin genes in the refactored thaxtomin biosynthetic gene cluster are from a pathogenic *Streptomyces* strain including, but not limited to, *Streptomyces scabiei, Streptomyces acidiscabies*, and *Streptomyces turgidiscabies*. In embodiments, the *Streptomyces* bacterium from a non-pathogenic *Streptomyces* strain can be, but is not limited to, one of the following strains: *S. albus, S. coelicolor, S. diastatochromogenes*, and *S. avermitilis*. In embodiments, the non-pathogenic bacteria may be from a different gram positive bacterial species, such as *Norcardia*, or other species compatible with receipt of the ThxA biosynthetic cluster from the pathogenic *Streptomyces* species. In embodiments, the pathogenic *Streptomyces* strain is *S. scabiei* and the non-pathogenic strain is *S. albus* J1074.

In order to select for successful integration of the exogenous, refactored thaxtomin biosynthetic gene cluster into the genome of the recipient non-pathogenic *Streptomyces* bacteria, in embodiments, the refactored thaxtomin biosynthetic gene cluster is operably linked to a nucleotide encoding a selectable marker. Thus, in such embodiments, the expression of the selectable marker indicates integration and expression of the thaxtomin genes in the refactored gene cluster. In embodiments, the selectable marker is antibiotic resistance (e.g., apramycin resistance, hygromycin B resistance, etc.), such as known to those of skill in the art, and described in greater detail in the examples below.

Methods of Providing Thaxtomin-production in Non-native *Streptomyces* in the Absence of Thaxtomin-inducing Conditions The present disclosure also provides methods of providing thaxtomin-producing capability in the absence of thaxtomin-inducing conditions in a non-native *Streptomyces* bacterium (or other Actinomycete capable of receiving and integrating the thaxtomin gene cluster into its genome). In embodiments, such methods include providing a *Streptomyces* bacterium from a naturally non-pathogenic species that does not produce thaxtomin and genetically engineering the bacterium to include an exogenous, refactored thaxtomin biosynthetic gene cluster that confers the ability to product thaxtomin in the absence of thaxtomin inducing conditions. In embodiments, the refactored thaxtomin biosynthetic gene cluster, as described above, includes one or more thaxtomin modules which may or may not be linked together, and together form the thaxtomin biosynthetic gene cluster.

As described above, the one or more thaxtomin modules each include: one or more thaxtomin genes from a thaxtomin biosynthetic gene cluster from a pathogenic *Streptomyces* bacteria and one or more promoters operably linked to the one or more thaxtomin genes. In embodiments, there are two or more thaxtomin modules and the thaxtomin genes in each module are different from those in the other module. However, it is envisioned that in some embodiments, multiple copies of one or more of the thaxtomin genes could be included among the thaxtomin modules, since an increase in gene copy can result in increased production. As described above, in embodiments, the promoter for each module can be the same or different, and in embodiments is a constitutive promoter. The arrangement of the refactored thaxtomin biosynthetic gene cluster provides the genetically engineered *Streptomyces* bacterium with the ability to produce at least one thaxtomin compound in the absence of thaxtomin-inducing conditions. The refactored thaxtomin biosynthetic gene cluster and its modules can be as described above, and the one or more thaxtomin compounds produced can be, but are not limited to, thaxtomin A, thaxtomin D, and other thaxtomin intermediates and/or analogs.

In embodiments, genetically engineering the *Streptomyces* bacterium to include an exogenous, refactored thaxtomin biosynthetic gene cluster includes providing a genetically engineered thaxtomin plasmid having the exogenous, refactored thaxtomin biosynthetic gene cluster and a nucleic acid encoding a selectable marker operably linked to the exogenous, refactored thaxtomin biosynthetic gene cluster. The naturally non-pathogenic *Streptomyces* bacterium can be transformed with the genetically engineered thaxtomin plasmid (or other transformation vector) to provide the transformed bacterium with the refactored thaxtomin biosynthetic gene cluster of the present disclosure. Successful transformants can be identified and selected, thereby providing the genetically engineered *Streptomyces* bacterium of the present disclosure that is capable of producing a thaxtomin compound in the absence of thaxtomin-inducing conditions.

In embodiments, the process of transforming the bacterial cells with the thaxtomin plasmid can be done using methods known to those of skill in the art. Such methods are intended to be included in the scope of the present application. Then the selectable marker can be used to selecting for transformants that harbor the refactored thaxtomin biosynthetic gene cluster. Additional methods (such as PCR) can be used to confirm integration of the refactored thaxtomin biosynthetic gene cluster into a genome of the naturally non-pathogenic *Streptomyces* bacterium. The resulting genetically engineered transformants express the thaxtomin genes in the modules included in the refactored gene cluster and are able to produce one or more thaxtomin compounds, such as, but not limited to thaxtomin A. In embodiments, the genetically engineered *Streptomyces* bacterium made according to the methods of the present disclosure are able to produce about as much or more thaxtomin in the absence of thaxtomin-inducing conditions than a wild type pathogenic species can produce in the presence of thaxtomin-inducing conditions.

In the various methods described herein, in embodiments, the refactored thaxtomin biosynthetic gene cluster is from a pathogenic *Streptomyces* strain including, but not limited to, *Streptomyces scabiei, Streptomyces acidiscabies*, and *Streptomyces turgidiscabies*. In embodiments, the *Streptomyces* bacterium from a non-pathogenic *Streptomyces* strain can be, but is not limited to, one of the following strains: *S. albus, S. coelicolor, S. diastatochromogenes*, and *S. avermitilis*. As mentioned above, in some embodiments the non-pathogenic recipient bacterial species is another non-pathogenic species compatible with transformation with and expression of the refactored thaxtomin biosynthetic gene cluster including thaxtomin genes from a pathogenic *Streptomyces* strain, such as, but not limited to *Norcardia*. In embodiments, the pathogenic *Streptomyces* strain is *S. scabiei* and the non-pathogenic strain is *S. albus* J1074.

The present disclosure also includes genetically engineered *Streptomyces* bacterium produced by the methods described in the present disclosure.

Methods of Producing Thaxtomin

The present disclosure also includes methods of producing thaxtomin. Embodiments of such methods include culturing the genetically engineered *Streptomyces* bacteria described above, so that the modified *Streptomyces* bacteria produce thaxtomin in the absence of thaxtomin-inducing conditions (e.g., in the presence of cellobiose or other known thaxtomin inducer). In the methods of producing thaxtomin of the present disclosure, the genetically engineered *Streptomyces* bacteria exhibit about the same or increased production of thaxtomin compound as compared to a wild type *Streptomyces scabiei* bacteria and, unlike wild type *S. scabiei*, are able to produce thaxtomin in the absence of cellobiose-containing media. As described above, in some embodiments of the genetically engineered *Streptomyces* bacteria of the present invention produce thaxtomin in environmental conditions (e.g., standard growth medium) where the native or wild type *Streptomyces* bacteria would not be able to produce thaxtomin or may only produce trace amounts. In embodiments of the methods of the present disclosure for producing thaxtomin, the thaxtomin produced by the genetically engineered *Streptomyces* bacteria of the present disclosure is collected and/or extracted from the cell culture. After collection/extraction of the thaxtomin from the cell culture, the thaxtomin may be further extracted/separated from the culture media, and/or the extracted thaxtomin may then be subject to further isolation and/or purification steps as needed or desired. In embodiments, the thaxtomin compound produced is thaxtomin A. In embodiments, the methods of the present disclosure can product more than one thaxtomin compound. In embodiments, the thaxtomin compound can include, but is not limited to, thaxtomin A, thaxtomin D, and other thaxtomin analogues and intermediates.

The isolated and/or purified thaxtomin compound produced by the genetically engineered *Streptomyces* bacteria of the present disclosure can then be used for various purposes, such as in the production of certain herbicides. Thus, the methods of the present disclosure also include methods of making herbicides including thaxtomin by producing thaxtomin according to the methods of the present disclosure and using the thaxtomin to produce the herbicide. The present disclosure also includes thaxtomin compounds produced by the methods of the present disclosure described above.

Methods of Producing Thaxtomin Intermediates and/or Analogues

The present disclosure also includes methods of producing thaxtomin intermediates or analogues. In embodiments, the thaxtomin analog or intermediate includes compounds such as, but not limited to: ortho-thaxtomin A, thaxtomin D, and nitro-tryptophans, such as, but not limited to 4-nitrotryptophan, N-methyl-4-nitrotryptophan, and N-acetyl-4-nitrotryptophan (FIG. 1).

In embodiments, methods of producing the thaxtomin analog, thaxtomin D (and possibly other thaxtomin analogs and/or intermediates) include the methods set forth above for genetically engineering a *Streptomyces* bacteria from a non-pathogenic *Streptomyces* strain in the absence of thaxtomin-inducing conditions where the refactored thaxtomin biosynthetic gene cluster includes one or more thaxtomin modules including thaxtomin genes, but where no module includes a txtC biosynthetic gene. In embodiments, the refactored thaxtomin biosynthetic gene cluster includes a first module, module 1, including a txtE and a txtD biosynthetic gene and a promoter, and a second module, module 2, including a txtA, a txtB, and txtH biosynthetic gene and a promoter, and wherein neither thaxtomin module includes a txtC biosynthetic gene. The thaxtomin modules are linked to form a refactored thaxtomin biosynthetic gene cluster such that expression of the refactored thaxtomin biosynthetic gene cluster provides the genetically engineered *Streptomyces* bacterium with the ability to produce at least one thaxtomin compound analog or intermediate in the absence of thaxtomin-inducing conditions. In embodiments, the thaxtomin compound analog or intermediate is thaxtomin D.

The refactored thaxtomin gene cluster, genetically modified bacteria of the present disclosure, methods of increasing thaxtomin compounds in *Streptomyces* bacteria, methods of producing thaxtomin without inducers, and thaxtomin and thaxtomin intermediates produced by methods of the present disclosure are described in greater detail in the following examples.

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Aspects

The following listing of exemplary aspects supports and is supported by the disclosure provided herein.

Aspect 1. A genetically engineered *Streptomyces* bacterium comprising: a *Streptomyces* bacterium from a non-pathogenic *Streptomyces* strain, the *Streptomyces* bacterium comprising an exogenous, refactored thaxtomin biosynthetic gene cluster comprising at least two thaxtomin modules, each module comprising: one or more thaxtomin genes from a thaxtomin biosynthetic gene cluster from a pathogenic *Streptomyces* strain, and one or more promoters operably linked to the one or more thaxtomin genes, wherein the at least two thaxtomin modules represent a refactored thaxtomin biosynthetic gene cluster such that expression of the refactored thaxtomin biosynthetic gene cluster provides the genetically engineered *Streptomyces* bacterium with the ability to produce at least one thaxtomin compound in the absence of thaxtomin-inducing conditions, wherein the non-pathogenic *Streptomyces* strain without the refactored thaxtomin cluster does not have the ability to produce the thaxtomin compound.

Aspect 2. The genetically engineered *Streptomyces* bacterium of aspect 1, wherein the at least two thaxtomin modules comprise: a first module, module 1, comprising a txtE and a txtD biosynthetic gene and a second module, module 2, comprising a txtA, a txtB, and txtH biosynthetic gene.

Aspect 3. The genetically engineered *Streptomyces* bacterium of aspect 2, further comprising a third module, module 3, comprising a txtC biosynthetic gene.

Aspect 4. The genetically engineered *Streptomyces* bacterium of aspect 3, wherein the at least one thaxtomin compound comprises thaxtomin A.

Aspect 5. The genetically engineered *Streptomyces* bacterium of any of aspects 1-4, wherein the one or more promoters for each module can be the same or different.

Aspect 6. The genetically engineered *Streptomyces* bacterium of any of aspects 1-5, wherein the promoter for each module is a constitutive promoter or inducible promoter.

Aspect 7. The genetically engineered *Streptomyces* bacterium of any of aspects 1-6, wherein the at least one thaxtomin compound comprises thaxtomin A.

Aspect 8. The genetically engineered *Streptomyces* bacterium of any of aspects 2, 5, or 6 wherein none of the thaxtomin modules comprise txtC and wherein the at least one thaxtomin compound comprises thaxtomin D.

Aspect 9. The genetically engineered *Streptomyces* bacterium of any of aspects 1-8, wherein the pathogenic *Streptomyces* strain is selected from the group of plant pathogenic *Streptomyces* species consisting of: *Streptomyces scabiei*, *Streptomyces acidiscabies*, and *Streptomyces turgidiscabies*.

Aspect 10. The genetically engineered *Streptomyces* bacterium of any of aspects 1-9, wherein the plant pathogenic *Streptomyces* species is *S. scabiei* 87.22 or other strain of *S. scabiei*.

Aspect 11. The genetically engineered *Streptomyces* bacterium of any of aspects 1-10, wherein the *Streptomyces* bacterium from a non-pathogenic *Streptomyces* strain is selected from species of *S. albus*.

Aspect 12. The genetically engineered *Streptomyces* bacterium of any of aspects 1-11, wherein the *Streptomyces* bacterium from a non-pathogenic *Streptomyces* strain is *S. albus* J1074.

Aspect 13. The genetically engineered *Streptomyces* bacterium of any of aspects 1-12, wherein the refactored thaxtomin biosynthetic gene cluster is operably linked to a nucleotide sequence encoding at least one selectable marker.

Aspect 14. The genetically engineered *Streptomyces* bacterium of aspect 13, wherein the selectable marker is antibiotic resistance.

Aspect 15. The genetically engineered *Streptomyces* bacterium of any of aspects 1-14, wherein the genetically engineered *Streptomyces* bacterium produces about the same or a greater amount of thaxtomin in the absence of thaxtomin-inducing conditions than *S. scabiei* produces in the presence of thaxtomin-inducing conditions.

Aspect 16. The genetically engineered *Streptomyces* bacterium of any of aspects 1-15, wherein thaxtomin-inducing conditions comprises media containing cellobiose.

Aspect 17. The genetically engineered *Streptomyces* bacterium of any of aspects 1-16, wherein the at least two thaxtomin modules are linked.

Aspect 18. The genetically engineered *Streptomyces* bacterium of any of aspects 1-18, wherein the thaxtomin genes in each module are different from the other module.

Aspect 19. The genetically engineered *Streptomyces* bacterium of any of aspects 1-18, wherein the one or more promoter for each module is independently selected from the group of constitutive promoters consisting of: P1, P6, P7, P8, P9, P10, P11, P13, P20, P23, P24, P28, P31, Ksaop*, and P6E-PID.

Aspect 20. A refactored thaxtomin biosynthetic gene cluster comprising: one or more thaxtomin modules, each module comprising: one or more thaxtomin genes from a thaxtomin biosynthetic gene cluster from a pathogenic *Streptomyces* bacteria, wherein if the thaxtomin biosynthetic gene cluster comprises only one thaxtomin module, that thaxtomin module comprises two or more thaxtomin genes, and one or more promoters operably linked to the one or more thaxtomin genes, wherein the one or more thaxtomin modules form a refactored thaxtomin biosynthetic gene cluster such that expression of the refactored thaxtomin biosynthetic gene cluster produces at least one thaxtomin compound in the absence of thaxtomin-inducing conditions.

Aspect 21. The refactored thaxtomin biosynthetic gene cluster of aspect 20, comprising at least two thaxtomin modules: a first module, module 1, comprising a txtE and a txtD biosynthetic gene, and a second module, module 2, comprising a txtA, a txtB, and txtH biosynthetic gene.

Aspect 22. The refactored thaxtomin biosynthetic gene cluster of aspect 21, further comprising a third module, module 3, comprising a txtC biosynthetic gene.

Aspect 23. The refactored thaxtomin biosynthetic gene cluster of any of aspects 20-22, wherein each module comprises one or more promoters, one or more ribosomal binding site, and one or more terminators, wherein the promoter for each module can be the same or different.

Aspect 24. The refactored thaxtomin biosynthetic gene cluster of any of aspects 20-23, wherein at least one of the thaxtomin modules comprises two or more thaxtomin genes and two or more promoters, wherein expression of each of the two or more thaxtomin genes is driven by a separate promoter.

Aspect 25. The refactored thaxtomin biosynthetic gene cluster of any of aspects 20-24, wherein the promoter for each module is a constitutive promoter or an inducible promoter.

Aspect 26. The refactored thaxtomin biosynthetic gene cluster of any of aspects 20-25, wherein the at least one thaxtomin compound comprises thaxtomin A.

Aspect 27. The refactored thaxtomin biosynthetic gene cluster of any of aspects 20, 21, or 23-25, wherein none of the thaxtomin modules comprise txtC and wherein the at least one thaxtomin compound comprises thaxtomin D.

Aspect 28. The refactored thaxtomin biosynthetic gene cluster of aspect 21, wherein module 1 comprises a first promoter to drive expression of txtE and second promoter to drive expression of txtD.

Aspect 29. The refactored thaxtomin biosynthetic gene cluster of aspect 21, wherein module 1 is under the control of a stronger constitutive promoter than any other module.

Aspect 30. One or more plasmids that together comprise the refactored thaxtomin biosynthetic gene cluster of any of aspects 20-29, wherein the plasmid is self-replicable or integrative.

Aspect 31. A method of providing a genetically engineered *Streptomyces* bacterium capable of producing thaxtomin compounds in the absence of thaxtomin-inducing conditions, the method comprising: providing a *Streptomyces* bacterium from a naturally non-pathogenic species that does not produce thaxtomin; and genetically engineering the *Streptomyces* bacterium to include an exogenous, refactored thaxtomin biosynthetic gene cluster comprising one or more thaxtomin modules that form the refactored thaxtomin biosynthetic gene cluster, each thaxtomin module comprising: one or more thaxtomin genes from a thaxtomin biosynthetic gene cluster from a pathogenic *Streptomyces* bacteria, and one or more promoters operably linked to the one or more thaxtomin genes in the one or more modules, wherein the exogenous, refactored thaxtomin biosynthetic gene cluster provides the genetically engineered *Streptomyces* bacterium with the ability to produce at least one thaxtomin compound in the absence of thaxtomin-inducing conditions.

Aspect 32. The method of aspect 31, wherein genetically engineering the *Streptomyces* bacterium to include an exogenous, refactored thaxtomin biosynthetic gene cluster comprises: providing one or more genetically engineered plasmids together comprising the exogenous, refactored thaxtomin biosynthetic gene cluster and a nucleic acid encoding a selectable marker operably linked to the exogenous, refactored thaxtomin biosynthetic gene cluster; transforming the naturally non-pathogenic *Streptomyces* bacterium with the genetically engineered plasmid; and selecting for transformants using the selectable marker to provide genetically engineered *Streptomyces* bacterium capable of producing a thaxtomin compound in the absence of thaxtomin-inducing conditions.

Aspect 33. The method of aspect 31 or 32, wherein the genetically engineered *Streptomyces* bacterium produces about the same or a greater amount of thaxtomin compounds in the absence of thaxtomin-inducing than *S. scabiei* produces in the presence of thaxtomin-inducing conditions.

Aspect 34. A genetically engineered *Streptomyces* bacterium produced by the method of any of aspects 31-33.

Aspect 35. A method of producing a thaxtomin compound, the method comprising: culturing genetically engineered *Streptomyces* bacteria from a non-pathogenic *Streptomyces* strain in the absence of thaxtomin-inducing conditions, the genetically engineered *Streptomyces* bacterium comprising an exogenous, refactored thaxtomin biosynthetic gene cluster comprising one or more thaxtomin modules, each module comprising: one or more thaxtomin genes from a thaxtomin biosynthetic gene cluster from a pathogenic *Streptomyces* bacteria, and one or more promoters operably linked to the one or more thaxtomin genes, wherein the one or more thaxtomin modules form a refactored thaxtomin biosynthetic gene cluster such that expression of the refactored thaxtomin biosynthetic gene cluster provides the genetically engineered *Streptomyces* bacterium with the ability to produce at least one thaxtomin compound in the absence of thaxtomin-inducing conditions.

Aspect 36. The method of aspect 35, further comprising extracting the thaxtomin compound from the culture medium.

Aspect 37. The method of any of aspects 35-36, wherein culturing the genetically engineered *Streptomyces* bacteria in the absence of thaxtomin-inducing conditions comprises culturing the genetically engineered *Streptomyces* bacteria in a culture medium that does not contain cellobiose.

Aspect 38. A method of producing a thaxtomin compound analog or intermediate, the method comprising: culturing genetically engineered *Streptomyces* bacteria from a non-pathogenic *Streptomyces* strain in the absence of thaxtomin-inducing conditions, the genetically engineered *Streptomyces* bacterium comprising an exogenous, refactored thaxtomin biosynthetic gene cluster comprising one or more thaxtomin modules, wherein the one or more thaxtomin modules comprise a txtE, a txtD a txtA, a txtB, and a txtH biosynthetic gene and one or more promoters operably linked to the biosynthetic genes, wherein the biosynthetic gene cluster does not comprise a txtC biosynthetic gene, and the thaxtomin modules form a refactored thaxtomin biosynthetic gene cluster such that expression of the refactored thaxtomin biosynthetic gene cluster provides the genetically engineered *Streptomyces* bacterium with the ability to produce at least one thaxtomin compound analog or intermediate in the absence of thaxtomin-inducing conditions.

Aspect 39. The method of aspect 38, wherein the refactored thaxtomin biosynthetic gene cluster comprises at least two separate thaxtomin modules: a first module, module 1, comprising a txtE and a txtD biosynthetic gene, at least one promoter, at least one ribosomal binding site, and at least one terminator, and a second module, module 2, comprising a txtA, a txtB, and txtH biosynthetic gene and at least one promoter, at least one ribosomal binding site, and at least one terminator, wherein neither thaxtomin module comprises a txtC biosynthetic gene, and the thaxtomin modules form a refactored thaxtomin biosynthetic gene cluster such that expression of the refactored thaxtomin biosynthetic gene cluster provides the genetically engineered *Streptomyces* bacterium with the ability to produce at least one thaxtomin compound analog or intermediate in the absence of thaxtomin-inducing conditions.

Aspect 40. The method of any of aspects 38-39, wherein the at least one thaxtomin compound analog or intermediate comprises thaxtomin D.

Aspect 41. A genetically engineered *Streptomyces* bacterium comprising: a *Streptomyces* bacterium from a non-pathogenic *Streptomyces* strain, the *Streptomyces* bacterium comprising an exogenous, refactored thaxtomin biosynthetic gene cluster comprising one or more thaxtomin modules, each module comprising: one or more thaxtomin genes from a thaxtomin biosynthetic gene cluster from a plant pathogenic *Streptomyces* bacterium, wherein if the thaxtomin biosynthetic gene cluster comprises only one thaxtomin module, that thaxtomin module comprises two or more thaxtomin genes and one or more promoters operably linked to the one or more thaxtomin genes in the one or more thaxtomin modules, such that expression of the thaxtomin genes in the refactored thaxtomin biosynthetic gene cluster provides the genetically engineered *Streptomyces* bacterium with the ability to produce at least one thaxtomin compound in the absence of thaxtomin-inducing conditions, wherein the non-pathogenic *Streptomyces* strain without the refactored thaxtomin cluster does not have the ability to produce the thaxtomin compound.

Aspect 42. The genetically engineered *Streptomyces* bacterium of aspect 41, wherein the refactored thaxtomin biosynthetic gene cluster comprises at least two thaxtomin modules.

Aspect 43. The genetically engineered *Streptomyces* bacterium of aspect 41 or 42, wherein each thaxtomin module comprises one or more promoters operably linked to the one or more thaxtomin genes in that module.

From the foregoing, it will be seen that aspects herein are well adapted to attain the ends and objectives hereinabove set forth together with other advantages which are obvious and which are inherent to the systems and methods.

It will be understood that certain features and subcombinations are of utility and may be employed without reference to other features and subcombinations. This is contemplated by and is within the scope of the aspects.

While specific elements and steps are discussed in connection to one another, it is understood that any element and/or steps provided herein is contemplated as being combinable with any other elements and/or steps regardless of explicit provision of the same while still being within the scope provided herein. Since many possible aspects may be made of the disclosure without departing from the scope thereof, it is to be understood that all matter herein set forth or shown in the accompanying drawings is to be interpreted as illustrative and not in a limiting sense

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1—Cellobiose-independent Production of Thaxtomins by Non-pathogenic *Streptomyces* Species from a Refactored Thaxtomin Gene Cluster In a previous study overproduction of thaxtomins was demonstrated in nonpathogenic *Streptomyces* species were engineered to carry the genomic island of the plant pathogen *S. scabiei* 87-22, which contains the thaxtomin biosynthetic cluster, resulting in overproduction of thaxtomin by the engineered *Streptomyces* species. However, in the previous study the thaxtomin biosynthetic cluster was still under the same transcriptional and translational controls as native hosts, and thus dependent on the presence of certain inducers, such as cellobiose. All experiments were performed on cellobiose supplemented media. In the present example, host nonpathogenic *Streptomyces* species have been transformed with engineered thaxtomin gene modules, designed such that the production of the thaxtomin pathway is not subject to controls that make thaxtomin production dependent upon the presence of cellobiose or other inducer.

Materials and Methods

Bacterial Strains and Culture Conditions

*Escherichia coli* strains were cultured in Luria-Bertani (LB) medium at 37° C. *Streptomyces* strains were cultured at 30° C. on the International *Streptomyces* Project medium 4 (ISP4) agar medium or in tryptic soy broth (TSB; BD Biosciences). All liquid cultures were shaken at 250 rpm. When required, media were supplemented with the following antibiotics at the indicated final concentrations: apramycin and nalidixic acid (50 μg/ml). *E. coli* strain S17-1 was used for conjugation with *S. albus* J1074. Strains and plasmids used in this study are described in Table 1.

Construction of Refactored Plasmids

End-overlapped DNA synthetic fragments of whole or partial thaxtomin synthetic gene cluster were PCR amplified using cosmid 1989/*S. albus* J1074 mycelium as templates and assembled with conjugative vector-pLST9828 through NEBuilder HiFi DNA Assembly Cloning Kit. The assembled mixtures were transformed into *E. coli* S17-1 cells. The constructed plasmids were confirmed by gel digestion and DNA sequencing. The conjugation of the transformed *E. coli* S17-1 with *S. albus* J1074 enabled the transfer of the whole or partial refactored thatxomin biosynthetic cluster into *S. albus* J1074.

The Procedure of Fermentation and Isolation Thaxtomins and Nitro-tryptophans Mycelial suspensions of *S. scabiei* and *S. albus* J1074 strains were prepared from 48-hour-old 20 ml TSB-grown cultures by pelleting the mycelia, washing twice with sterile water, and resuspending in 20 ml sterile water. For analysis of thaxtomin production, TDM medium with 1% sugar was used (as described in Johnson, E. G., et al., 2007, which is hereby incorporated by reference herein). Three times 50 ml medium in 250 mL flasks were inoculated with 0.5 ml of mycelial suspension of $OD_{600\ nm}$ 1.0. After incubation for 6 days at 30° C. with shaking at 250 rpm, the culturing media were centrifuged with 5000 rpm to pellet the mycelium. The supernatants of centrifugation were added to C18 columns (waters-2 g). Nitrotrptophans were eluted out with 25% methanol while thaxtomins were eluted with 100% methanol. Thaxtomins could also be extracted by ethyl acetate directly from supernatant which could provide the same amount of thaxtomins from the same volume of supernatant. Experiments were repeated using different biological replicates of the *Streptomyces* strains with three technical replicates per strain.

Analytical HPLC Analysis Method

The HPLC column (Agilent Poroshell 120 EC-C18, 2.7 μm, 4.6×50 mm), kept at 30° C., was eluted first with 10% solvent B (acetonitrile with 0.1% formic acid) for 2 min and then with a linear gradient of 10-50% solvent B in 8 min, followed by another linear gradient of 50-99% solvent B in 5 min. After eluting in 99% solvent B for 3 min, the liner gradient of 99-10% solvent B in 1 min was used. The column was further re-equilibrated with 10% solvent B for 1 min. The flow rate was set as 0.5 ml/min, and the products were detected at 380 nm with a PDA detector.

Semi-preparative HPLC Isolation Method

For semi-preparative analysis, the column (ZORBAX SB-C18, 5.0 μm, 9.4×250 mm) kept at 40° C. was eluted first with 10% solvent B (acetonitrile with 0.1% formic acid) for 2 min and then with a linear gradient of 10-50% solvent B for 8 min, followed by a linear gradient of 50-99% solvent B for 5 min. The column was then cleaned by 99% solvent B for 3 min and re-equilibrated with 10% solvent B for 1 min. The flow rate was set at 3 ml/min, and the products were detected at 380 nm with a PDA detector. All isolates were combined, concentrated, freeze-dried, and then weighed.

LC-MS Analysis of Isolated Products

A SHIMADZU Prominence UPLC system fitted with an Agilent Poroshell 120 EC-C18 column (2.7 µm, 4.6×50 mm) coupled with a Linear Ion Trap Quadrupole LC/MS/MS Mass Spectrometer system was used in the studies. The column was eluted with 10% solvent B (acetonitrile with 0.1% formic acid) for 2 min and then with a linear gradient of 10-50% solvent B in 8 min, followed by another linear gradient of 50-99% solvent B in 5 min. After eluting in 99% solvent B for 3 min, the liner gradient of 99-10% solvent B in 1 min was used. The column was further re-equilibrated with 10% solvent B for 1 min. The flow rate was set as 0.5 ml/min. For MS detection, the turbo spray conditions were identical for all chemicals (curtain gas: 30 psi; ion spray voltage: 5500 V; temperature: 600° C.; ion source gas 1:50 psi; ion source gas 2:60 psi).

Results

Refactoring the Thaxtomin Gene Cluster for Cellobiose-independent Production of Thaxtomins First, the thaxtomin biosynthetic gene cluster from S. scabiei 87.22 was refactored into three functionally distinct modules, as illustrated in FIG. 2: module 1 with txtD and txtE for the production of 4-$NO_2$-l-tryptophan, module 2 with txtA, txtB and txtH for the construction of diketopiperazine core of thaxtomins and module 3 with txtC for the tailoring hydroxylations. The thaxtomin biosynthetic gene clusters from other pathogenic Streptomyces strains can be refactored using the same approach. The expression of each module was separately controlled by its own promoter as well as ribosomal binding site and terminator to allow the improved production through fine tuning and balancing the expression of each module. In this Example, the $P6^{33}$ was used as the promoter to drive the expression of all three modules, because it is a strong constitutive native promoter of S. albus J1074 (gene2392). All synthetic biology parts, genes and an integrative plasmid pLST9828 were amplified in PCR reactions and assembled by NEBuilder® HiFi DNA Assembly Cloning Kit (NEB). The assembled plasmid was then transformed into E. coli S17-1, followed by the conjugation with S. albus J1074 to create the production strain S. albus J1074-RF-thx. Using the same strategy, S. albus J1074-RF-ΔC-thx was created that lacks the last module with txtC.

Production of Thaxtomins by S. albus J1074-RF-thx

The engineered strain S. albus J1074-RF-thx was cultured in multiple media with different nutrient components, including R5, TB, NBYE, LB, ISP4 and ISP2. The native thaxtomin producer S. scabiei 87.22 was included as the control. The strains were cultured at 30° C. and 250 rpm for 6 days. The clear supernatants were then collected after the centrifugation and passed through C18 cartridge. Nitrotryptophan analogs (compounds 5-6, FIG. 1) were then eluted with 25% methanol, while 100% methanol then eluted thaxtomin analogs (compounds 1-3, FIG. 1).

Figure 3:
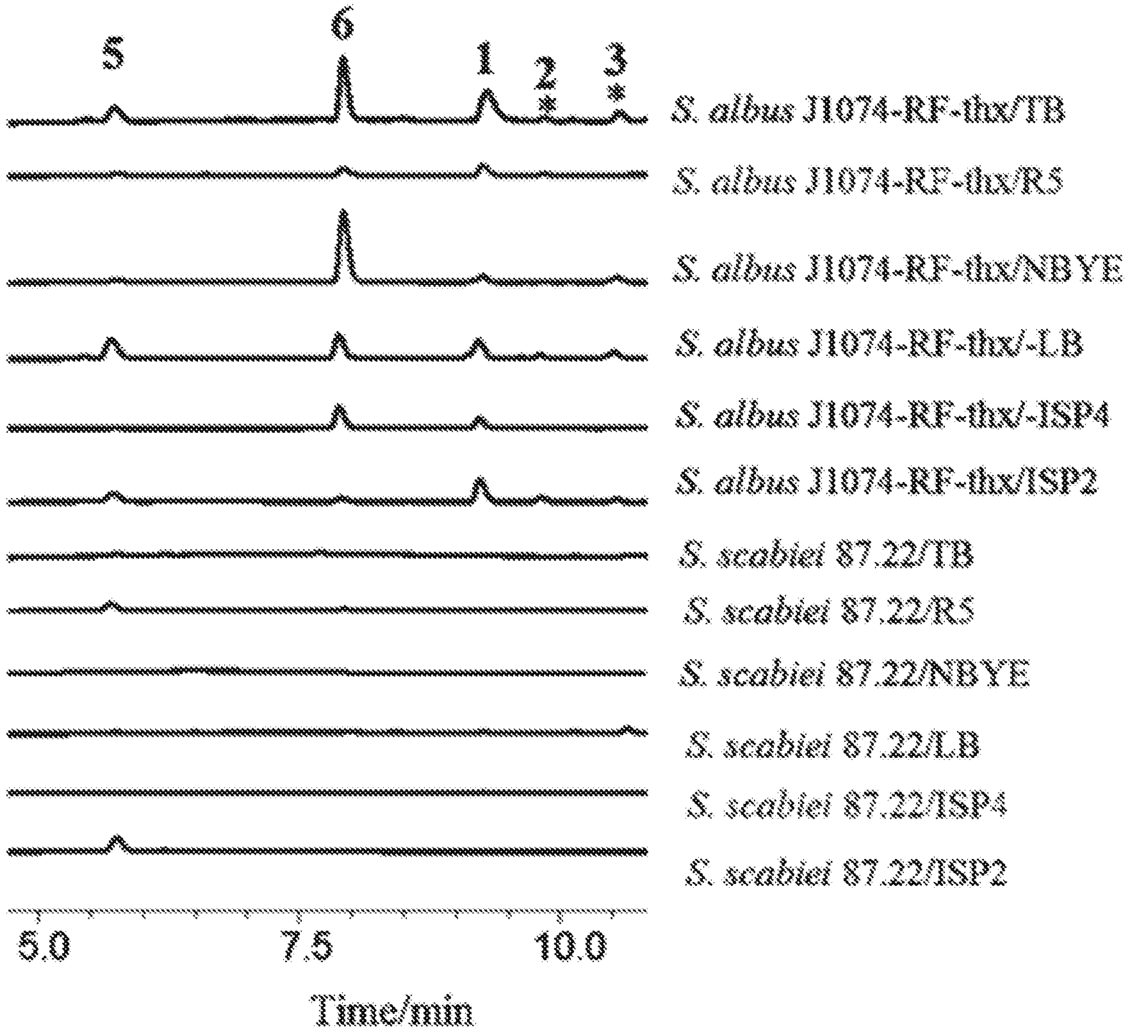
FIG. 3 illustrates HPLC analysis of metabolite profiles of *S. albus* J1074-RF-thx and *S. scabiei* 87.22 cultured in different media.

The fractions containing the same set of metabolites were combined, dried, and re-dissolved in methanol for HPLC analysis. Thaxtomin A (peak 1) and N-acetyl-4-$NO_2$-l-tryptophan (6) were present in all extracts from S. albus J1074-RF cultures, and some effects of culture media on the metabolite profiles of S. albus J1074-RF-thx were observed (FIG. 3). S. albus J1074-RF-thx produced thaxtomin A (peak 1), Ortho-thaxtomin A (peak 2), thaxtomin D (peak 3), N-methyl-4-$NO_2$-l-tryptophan (peak 4), and N-acetyl-4-$NO_2$-l-tryptophan (peak 6) in TB and LB culturing media, while only trace amounts of thaxtomin A and N-acetyl-4-$NO_2$-l-tryptophan were detected from the R5 culturing medium. TB and NBYE supported the highest level of N-acetyl-4-$NO_2$-l-tryptophan. TB, ISP2, and LB supported the highest yields of thaxtomin A, in that order. The isolation yield of thaxtomin A in ISP2 reached 18.8 mg/L. Although no 4-$NO_2$-l-tryptophan (4) was detected in any culture of S. albus J1074-RF-thx, the accumulation of N-acetyl-4-$NO_2$-l-tryptophan and/or N-methyl-4-$NO_2$-l-tryptophan and thaxtomins in these extracts suggests the high activity of module 1 of the refactored thaxtomin gene cluster. This result also suggested the high activities of unidentified N-acetyltransferases and N-methyltransferases in S. albus J1074 that together effectively acylate the amine of 4-$NO_2$-l-tryptophan, potentially competing with TxtB and TxtA in the synthesis of thaxtomins. No media supported the production of thaxtomin analogs by S. scabiei 87.22 (FIG. 3), probably due to the absence of natural inducers, such as cellobiose. Trace amounts of N-methyl-4-$NO_2$-l-tryptophan and N-acetyl-4-$NO_2$-l-tryptophan were observed in the extracts of S. scabiei 87.22 cultured in R5 and ISP2.

Figure 4:
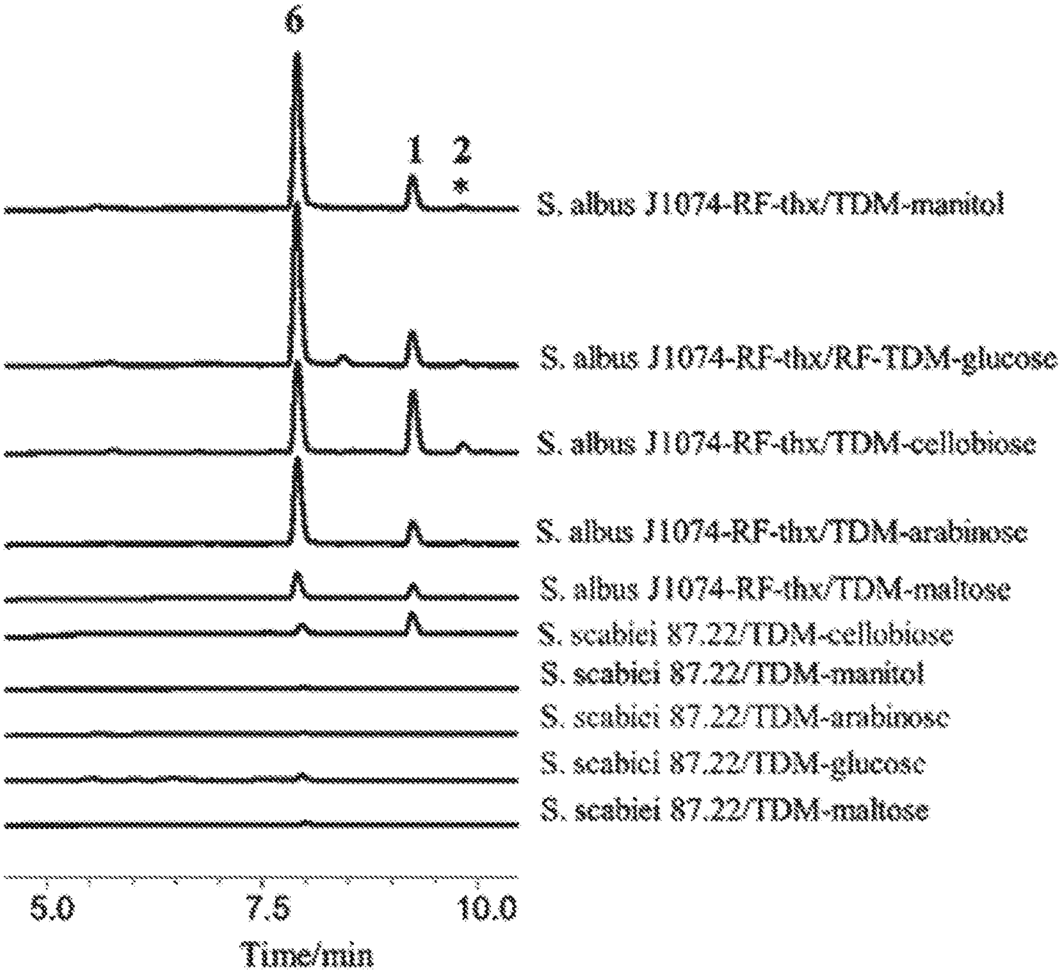
FIG. 4 illustrates HPLC analysis of metabolite profiles of *S. albus* J1074-RF-thx and *S. scabiei* 87.22 cultured in TDM supplemented with various sugars.

The Effects of Sugars on the Production of Thaxtomins by S. albus J1074-RF-thx Previous studies have found that the minimal medium TDM supplemented with cellobiose (TDMc) allows S. scabiei 87.22 to produce the relative high yield of thaxtomin A. (see Wach, M. J., et al. 2007 and Johnson, E. G., et al., 2007). The production of thaxtomin A (9.1 mg/L) when culturing S. scabiei 87.22 in TDMc medium for 6 days was confirmed. Remarkably, S. albus J1074-RF-thx produced 29.3 mg/L of thaxtomin A in the TDMc medium, as determined by the HPLC analysis. Since the expression of the refactored thaxtomin gene cluster is designed to be cellobiose-independent, this costly sugar very likely acts only as the carbon source to support cellular processes. Accordingly, other sugars were examined as the carbon sources to culture S. albus J1074-RF-thx. HPLC analysis revealed that S. albus J1074-RF-thx produced thaxtomin A, Ortho-thaxtomin A, and N-acetyl-4-$NO_2$-l-tryptophan in TDM media carrying various sugar components including mannitol, glucose, arabinose, and maltose (FIG. 4). The highest yield of thaxtomin A was observed at 20.4 mg/L when TDM was supplemented with glucose (TDMg). Importantly, the cost of TDMg can be lower than 20 cents per liter. By contrast, the cost of TDMc (based on chemical costs listed in Sigma-Aldrich website) can be 70 times higher than TDMg. This result clearly demonstrates the cost-effective overproduction of thaxtomins using the S. albus J1074-RF-thx strain.

Furthermore, S. albus J1074-RF-thx produced a large quantity of N-acetyl-4-$NO_2$-l-tryptophan (compound 6, FIG. 1) in TMD media supplemented with mannitol, glucose, and arabinose (FIG. 4). This metabolite is believed to be produced by acetylating 4-$NO_2$-l-tryptophan that is the enzymatic product of TxtE and TxtD (module 1). Its accumulation suggests the possibility of higher expression levels of modules 2 and 3 to achieve further improved production of thaxtomins. Metabolomics and transcriptomics approaches will be used to optimize and balance the expression level of each module in the refactored thaxtomin gene cluster to further improve the production of thaxtomins.

Using the same approach, the production of thaxtomins by *S. scabiei* 87.22 was examined in TDM medium supplemented with the above sugars. Although the trace amount of N-acetyl-4-$NO_2$-l-tryptophan was detected from the extracts of all culture media in HPLC analysis (FIG. 4), the production of thaxtomins was still completely abolished in the absence of cellobiose. These studies therefore clearly demonstrated the great potential of *S. albus* J1074-RF-thx to produce thaxtomins in a cost-attractive manner.

Figure 5:
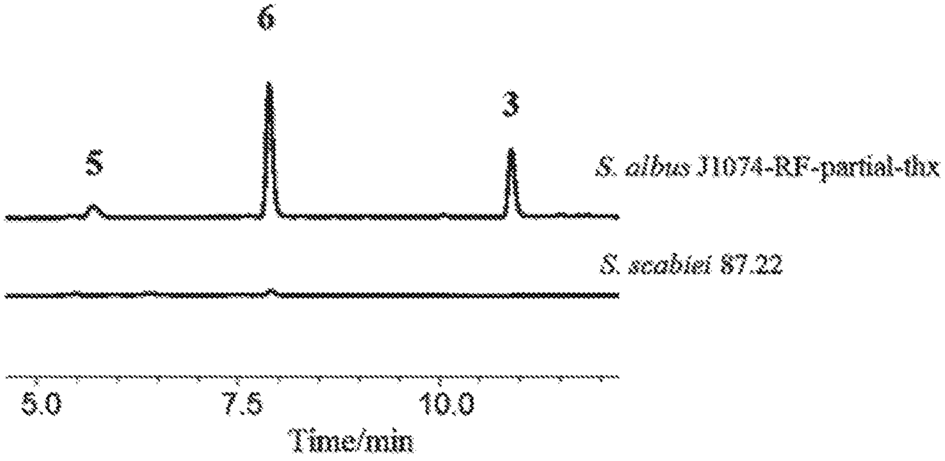
FIG. 5 illustrates HPLC analysis of extracts of *S. albus* J1074-RF-ΔC-thx and *S. scabiei* 87.22 cultured in TDMg medium. *S. albus* 1074-RF-partial-thx: *S. albus* J1074-RF-ΔC-thx.

Production of Thaxtomin Biosynthetic Intermediates by *S. albus* J1074-RF-ΔC-thx Thaxtomin biosynthetic intermediates can serve as useful precursors to chemically synthesize new thaxtomin analogs. Thaxtomin D is the earliest diketopiperazine intermediate within the thaxtomin biosynthetic pathway. Its yield is low in various culturing media of *S. scabiie* 87.22 and *S. albus* J1074-RF-thx (compound 3, FIGS. 3 and 4), but thaxtomin D is accumulated when the txtC gene is inactivated in *S. scabiei* 87.22 (Healy, F. G., et al., 2002) A partially refactored thaxtomin cluster carrying only modules 1 and 2 was created (FIG. 2., top, "partially refactored thaxtomin gene cluster"). This partial cluster was conjugated into *S. albus* J1074 to generate *S. albus* J1074-RF-ΔC-thx. This strain was cultured in TDMg medium, and HPLC analysis identified N-methyl-4-$NO_2$-l-tryptophan (compound 5), N-acetyl-4-$NO_2$-l-tryptophan (compound 6), which is a dominant metabolite, and thaxtomin D (compound 3) in the culture extract (FIG. 5). The yield of thaxtomin D was quantitated to be 22.4 mg/L. As a control, no thaxtomin D was produced by *S. scabiei* 87.22 in TDMg. This result further demonstrated the great promise of *Streptomyces* hosts carrying the refactored thaxtomin cluster to produce thaxtomin analogs in a cost-effective manner.

TABLE 1

Bacterial strains, plasmids, and cosmids used in this study

| Strain or plasmid | Description† | Source or reference |
|---|---|---|
| *E. coli* strains | | |
| S 17-1 | General cloning and conjugation donor strain ($tmp^R$) | 35 |
| Plasmids or cosmids | | |
| Cosmid 1989 | SuperCos1 derivative containing the *S. scabiei* 87-22 txtH locus ($kan^R$, $amp^R$) | This study |
| pLST9828 | Integrative Plasmid ($amp^R$) | This study |

†$apr^R$, apramycin resistance; $kan^R$, kanamycin resistance; $amp^R$, ampicillin resistance Example 2—Characterization of the Strengths of Multiple Different Promoters in Producing N-acetyl-4-$NO_2$-l-tryptophan (6)

Following on the results from Example 1 with the complete and partial refactored thaxtomin gene clusters using the P6 as the promoter (FIG. 2) to drive the expression of each module in the absence of cellobiose, the present Example tested the activity of additional promoters. Using the P6 promoter for each module as described in Example 1 and illustrated in FIG. 2 led to the significant accumulation of compound 6, one derivative of biosynthetic building block 4-$NO_2$-l-tryptophan (FIGS. 3-5). To further optimize the expression of each module, 14 additional constitutive promoters of *S. albus* were tested using similar methods as described above for Example 1. These 14 promoters have been identified and characterized with a report gene (xylE) in Luo, et al. (*ACS Synth Biol.,* 2015, 4, 1001-1010, which is hereby incorporated by reference herein).

Materials & Methods

End-overlapped DNA synthetic fragments were PCR amplified using cosmid 1989/*S. albus* J1074 mycelium as templates and assembled with conjugative vector pLST9828 using the NEBuilder HiFi DNA Assembly Cloning Kit. Primers were developed according to known procedures for amplification and cloning. The assembled mixtures were transformed into *E. coli* S17-1 cells. The constructed plasmids were then isolated and confirmed by DNA sequencing. The conjugation of the transformed *E. coli* S17-1 with *S. albus* J1074 enabled the transfer of the designed clusters into *S. albus* J1074. Any materials and methods not described here are the same as described for Example 1, above.

Results & Discussion

Figures 6A, 6B:
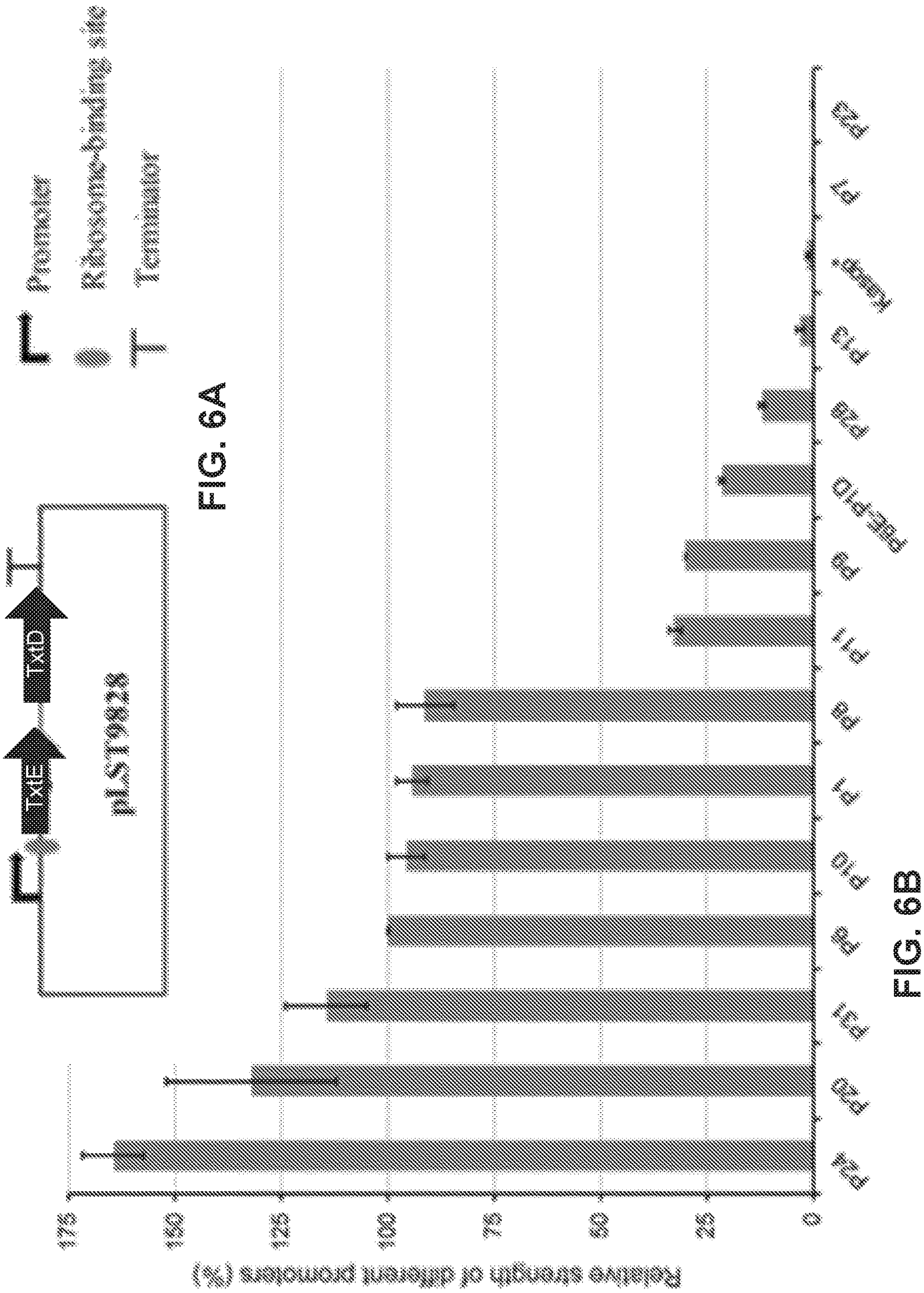
FIG. 6A illustrates a designed refactored thaxtomin cluster for the expression of 4-$NO_2$-I-tryptophan in *S. albus* J1074, which is further converted into compound 6.
FIG. 6B is a graph illustrating the relative activity of different constitutive promoters from *S. albus* in driving the expression of the designed cluster of FIG. 6A. HPLC analysis quantitated the concentration of compound 6 in the ISP4 medium of each strain. The amount of compound 6 produced by the cluster containing the P6 was set as 100% for normalizing the relative strength of other promoters. The data represent means±S. D. of at least two independent experiments

In addition to the P6 (SEQ ID NO: 16), 14 constitutive promoters (P1, P7, P8, P9, P10, P11, P13, P20, P23, P24, P28, P31, Ksaop*, and P6E-PID (SEQ ID NOs: 15, and 17-29, respectively)) were cloned from the genomic DNA of *S. albus* J1074 and used to drive the expression of the module illustrated in FIG. 6A including only the TxtE and TxtD gene. These constructs were then conjugated into *S. albus* J1074 as described in Example 1, and the selected colonies were cultured in ISP4 for 7 days. The yields of compound 6 were quantitated in the culture medium of each strain by HPLC analysis (FIG. 6B). This analysis identified the P24 as the strongest promoter with an apparent strength 1.6 times higher than the P6. On the other hand, eight promoters were weaker than P6, ranging from 32% (P11) to 0.1% (P23). These constitutive promoters with weak, medium, and strong strengths offered value opportunities to fine tune the expression of each module of the refactored thaxtomin gene cluster such as the clusters illustrated in FIG. 2 from Example 1, above, which can provide improved productivity and the reduced accumulation of relevant biosynthetic intermediates (e.g., compound 6).

Example 3—Improved Production of Thaxtomins Using Promoters of Different Strengths in Refactored Thaxtomin Biosynthetic Gene Clusters With the understanding of the strengths of 15 different constitutive promoters in expressing compound 6, from Example 2 above, new refactored thaxtomin gene clusters were designed with combinations of promoters and tested. This Example sought to improve the yield of thaxtomins in the absence of cellobiose on the basis of the modular design of refactored thaxtomin gene cluster described above (Example 1, FIG. 2). As shown in FIGS. 3, 4 and 5, the initial refactored gene cluster led to the significant accumulation of compound 6 whose production competes with the production of thaxtomins by consuming 4-$NO_2$-l-tryptophan. Therefore, the present Example sought to determine if the increased cellular availability of 4-$NO_2$-l-tryptophan can enhance the production of thaxtomins. Thus, the present Example describes two new refactored gene clusters (FIG. 7A). In the new refactored gene clusters of the present Example, either all genes in module 1 (TxtE and TxtD) are together driven by the strongest promoter P24 as well as ribosomal binding site and terminator (FIG. 7, top cluster), or the expression of TxtE and TxtD is separately controlled by P6 and P1, respectively, along with the same ribosomal binding site and terminator (FIG. 7A, bottom cluster). The second refactored cluster was tested to see if the separate control of TxtD expression, which produces NO from I-arginine, can improve the production of thaxtomins. NO is the co-substrate of TxtE and also toxic to thaxtomin-producing cells.

Materials & Methods

The following procedures were used for creation of *S. albus* J1074-P6TxtC-P6TxtABH-P24TxtED and *S. albus* J1074-P6TxtC-P6TxtABH-P6TxtE-P1TxtD (illustrated in FIG. 7A). NEBuilder HiFi DNA Assembly Cloning Kit was used to generate the PCR fragments of P6TxtE-P1TxtD and P24TxtED. These fragments and pSL9828-P6TxtC-P6TxtABH-P6TxtED were then treated with DraI and NdeI. After gel purification, the digested fragments were separately cloned into the digested plasmid to create pSL9828-P6TxtC-P6TxtABH-P6TxtE-P1TxtD and pSL9828-P6TxtC-P6TxtABH-P24TxtED.

The two gene clusters were transferred into *S. albus* J1074 as described above to create *S. albus* J1074-RF-thx to generate *S. albus* J1074-P6TxtC-P6TxtABH-P24TxtED and *S. albus* J1074-P6TxtC-P6TxtABH-P6TxtE-P1TxtD. The two engineered strains carrying these two clusters were then fermented in ISP4 and TDMm (TMD media supplemented with 1% mannitol) at 30° C. and 250 rpm for 4 days. Thaxtomins were extracted from clear culture media using C18 columns as described above

Results & Discussion

Figure 7C:
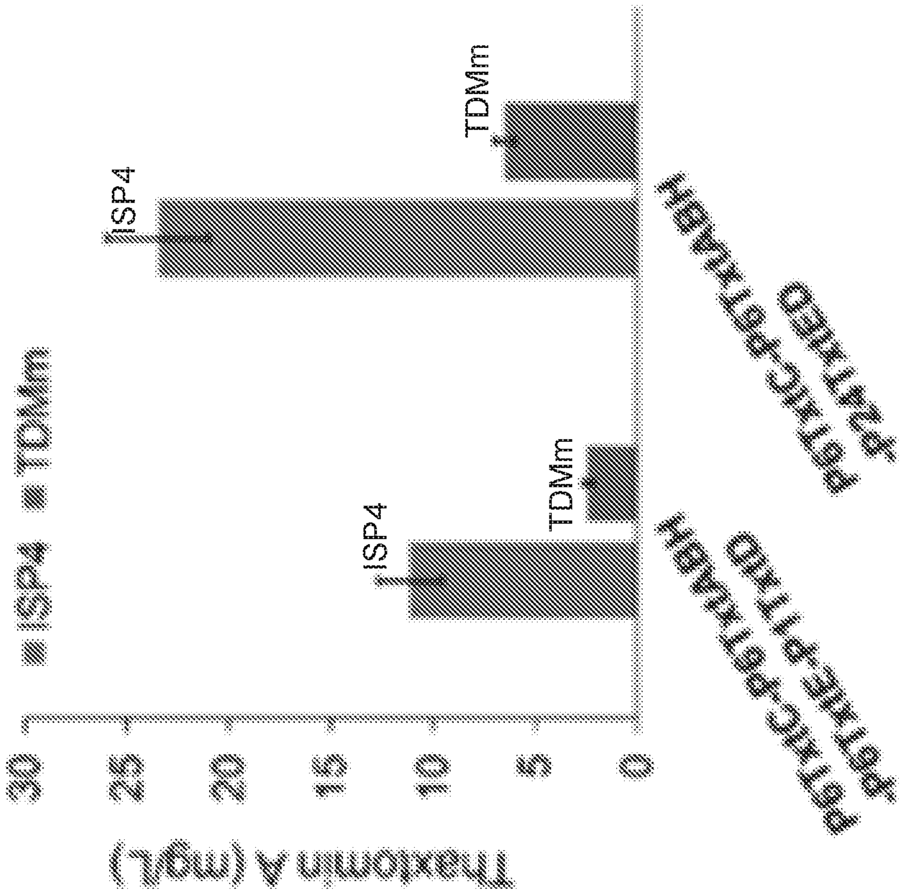
FIG. 7C is a graph illustrating the production of thaxtomin A by *S. albus* J1074-P6TxtC-P6TxtABH-P6TxtE-P1TxtD and *S. albus* J1074-P6TxtC-P6TxtABH-P24TxtED in TDMm and ISP4. The data represent means±S. D. of at least two independent experiments.
Figure 7B:
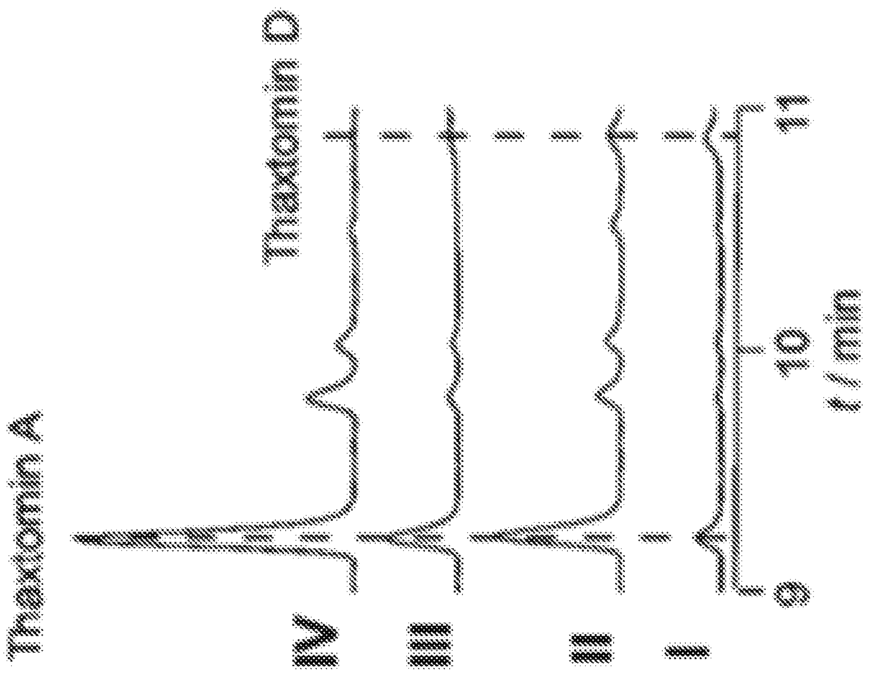
FIG. 7B is an HPLC analysis revealing the production of thaxtomin analogues by two *S. albus* J1074 strains engineered with the refactored gene clusters of FIG. 7A in ISP4 and TDMm media. Traces I and II represented the extracts from TDMm and ISP4 media of *S. albus* J1074-P6TxtC-P6TxtABH-P6TxtE-P1TxtD, respectively. Traces III and IV indicated the extracts from TDMm and ISP4 media of *S. albus* J1074-P6TxtC-P6TxtABH-P24TxtED, respectively. The strains were cultured at 30° C. and 250 rpm for 4 days.

As shown in FIG. 7B, both strains produced 3-6 times more thaxtomin A in ISP4 (traces II and IV) than TDMm (traces I and III), further supporting that media optimization is a viable approach to increase the productivity of thaxtomins from the refactored gene cluster. On the other hand, the use of the P24 (traces III and IV) to express the module 1 accumulated higher concentrations of thaxtomin A compared to separate regulation of TxtE and TxtD genes in both media (traces I and II) (See FIG. 7B).

The yields of thaxtomin A and D were further quantitated in two culture media of the two strains (FIG. 7C). This analysis revealed that the strain carrying P6TxtC-P6TxtABH-P24TxtED (*S. albus* J1074-P6TxtC-P6TxtABH-P24TxtED) produced about 23 mg/L of thaxtomin A in ISP4. Of note, *S. albus* J1074-RF-thx produced 29.3 mg/L, 20.4 mg/L and 18.8 mg/L of thaxtomin A in TDMc, TDMg, and ISP2, respectively, at 30° C. and 250 rpm for 6 days (FIGS. 3 & 4). As a comparison, the productivity of thaxtomin A by *S. albus* J1074-P6TxtC-P6TxtABH-P24TxtED reached 78.5% of the previous highest value but only took 4 days. Importantly, this work indicates that the use of additional promoters of varying strengths to fine tune the expression of genes in the refactored gene cluster can further improve the productivity of thaxtomin A.

```
LISTING OF SEQUENCES:
txtA (scab31791)
                                                        (SEQ ID NO: 1)
GTGTCGCACCTGACCGGTGAAGATCTCCCGGAGGGAGCGCTCGCCACGACGTGGCCGAGT

CTCCTCGAAGCGCGGGTGGCCGACACACCTGACGCCATCGCGCTCGTCGCCGGGGACACG

GCGCTCACGTACGCGCAGTTCAATGCCCGTGCGAACCGGCTCGCCCGGTGGCTGAAGTAC

CTCGGCGCCGGGCCGGAGCGGTCGGTCGGGCTGGTGCTGGGCAGGTCCGCGGACTTCTTC

CTGTGCGCGACGGCCGTGCTCAAGTGCGGGGCCGCGTACCTGCCGCTGGATCCGAACTAC

CCCGTGGAGCGACTGTCCTTCATGGCCCGGGACGCAGCACCCGTGGTGCTGGTGACGACG

TCGGACGTCCGGGGCGACCTTCTGGGCCAGCTGCCCACCGGCAGCCTCGTGGTACTGGAC

GACGAGGCCACCGAGGACGTACTGCGCCGTCTGCCGGACCACGACATGGAGGACGGGGAA

CGTTTGGAGCCACTGCGCCCCGCGAGTCCCGCCTACATCATCTACACCTCCGGCTCCACG

GGGATCCCCAAGGGAGTCGTCGTCACCCACCAAGGCGTCGCGAGCCTGATCGCGACCCAG

CGTCGTCGCCTCGCCGTCACCGGCGCCTCACGCGTGCTCGCCTTCTCGTCCCCGAGTTTC

GACGCCAGTTTCTGGGAGATGTCGATGGCGCTGCTGGCCGGGGCCGCGCTCGTGGTCGGC

AGGCCGGGGCGGCTGCTGCCCGACGCCGAACTGGCCGCGTTGATCGCGGACCACGGAGTC

ACTCATGTCACTCTCCCGCCCTCGGTCGCGGGTGCGCTGGGCCCCGACATGCTGCCTCCG

AGCGTGACGCTGGTCGTCGCGGGCGAAGCGTGCCCGGCGGCTCTCGTGCAGCGCTGGCGC

CCGCACCGGACGATGGTGAACGCCTACGGCCCGACGGAGTCCACCGTCTGCGCCACCATG

AGCGATCCGCTGGCCGACGACGTGGCGCCGCCGGTCGGCCGGGCGGTGGACGGCACCCGG

ATCCATGTCCTCGACGACCGCCTCGCACCGGTTGTGCCGGGAGCGGTCGGCGAGATCTAC

ATCGCGGGGCACAGCCTGGCACGCGGGTACCTCGAGCGGCCGGGTCTGACCGCGCAGCGG
```

-continued

TTCGTGGCGGACCCCTTCGGCCCGGCCGGCAGCCGTATGTACCGCAGCGGTGACCTCGGC

CGCTGGACCCGTTCAGGAGACCTGGAGTTCGTCGGCAGGGCGGACGACCAGGTCAAGGTA

CGCGGCTTCCGTATCGAGCCGGGCGAGATCGAATCCGTCATCGCCGGGTGCCGCGGGGTC

CGGCAGGCCGCCGTCGTCCTGCGTGAGGACCGGCCCGGAGAGCCATACCTCGCCGCCTAC

GTCATACCCGAGAACGCGGCCGCCGACGAGGCGGCCGGCGAGGAACCGGACGGTCAACTC

GATGCCTGGCGACGGCTCTACGACGATCTGTACGGCCGAGCCGACACCGCCGACTTCGGC

GAGGACTTCTCCGGCTGGGTGAGCAGTTATGGCGGGCGGCCGATCGAGGGGATGCGCGAA

TGGCGTGAGCAGACCGTGCGGCAGATCCGCGAACTGGCTCCGCGCCGCGTACTGGAGATC

GGCTGCGGTTCCGGTCTGCTGCTCTCGCAGCTGGCGGGTGACTGCGAAAGCTACTGGGGC

ACCGACATCTCCGGGGCCCTGATCGAGCGGCTGCGCGGGCAGGTCGCCGAGCGCCCCGGC

CTCGCGGACCGGGTCGTCCTGCATCAGCTCTCCGCCCATGAGCTGGGGAGTCTGCCCAGC

GGCGGCTTCGACACCGTCGTGCTCAACTCCGTGATCCAGTACTTTCCCTCAGGCGATTAC

CTGTTCGACCTACTGCGCGAGGTGTCCCGGCTCCTGGTACCCGGGGGCGCGGTGTTCCTC

GGCGACGTCCGTAACCTTCGTCTGCTGCGCACCTTCCACGCCGGGGGGCTGCTGGCGGCG

GCCACGCACACCGACACTCCGCAGACGGTCTGCGCGGCGATCGACCGGGCCATGGCGCAG

GAGAAGGAACTGCTCGTGGACCCGGAGTTCTTCACGACGGCCGTCGGCGCGCTGCCCGGC

ATGACGCTGGAGTCGTGCACGCTCAAACGGGGCGGGTACGACAACGAACTCAGCCGCTAT

CGCTACGAGGTGGTGCTGCGCAAGCATGCCGGGCCTGCCGATGACACCGGGCCCACGGAC

GACGCGGGGCCGGTCGTGCGACTGCGGTGGGACGGCGAGATGGCGAGCCTGGCCGACGTC

GCCGATCGGCTGCGTCGTGGGAAACCGGAGCGGTTGTGCGTCACCGGGATCCCCAACGGC

CGGGTGGCCGGCGAGCATGCCGCGACACTCGCGCTGTTCGACCGGCGCCCCCTGCACGAG

GTGCTGTCCCTGGGGCAGGCTCCGGCGGGCGTGGCACCGGAGGACCTGCGCCGGCTGGGC

GCGGAACTGGGCTACCGGGTCGACTGCACCTGGTCGTCCGAGGACGACGCCCTGATCGAC

GCTTCCTTCACACGCGCCGGAGCGCTCGTGCCGCGTCCCGCCCCCCGGACCGACGCGGAG

CCGGACGGTTTCTCCCCGGCCCGGTTCACCAACAGGCCGGCGTTCGCCCGCCCCGACTCC

CAGACGATGGCCTCTCTTCCCGGGCAGGTCGCGGCGAAGCTGCCGGCCTTCATGGTCCCG

GAGGTCTTCGTCCCGCTCGACAGGCTGCCGGTCACGGTGAACGGAAAGCTCGACCGCGGC

GCCCTGCCCCGGCCGCGGCGCGCCGCCCATGCCTCGGGACGTCCGCCCAGGACCGCCCGC

GAGGAGGTACTGGCGGCGATCTTCGCCGACGTACTCGCGACAGCCGACGTCACAGCCGAC

AGCGACTTCTTCGCCGTCGGCGGCAACTCCCTGCTGGCCACCCGACTCGCCGCCGAGGTC

CGGCGGCGCCTGAACACCGAGATGCCGCTGTCGTGGCTGTTCGAGTCGCCCACCGTCGGC

GCGCTCGCCGCCCGCTTCGACGCGGGGGACGAGGCCAGGCCGCTGCCCGTGCCGAGCGAG

TACGCCTCCGGCAGCACGGCGCCGTTGTCGGCCCAGCAGATGCAGATGTGGCACGAGTAC

CGCCGAAGCCTGTGTCGCGACATGTTCAACGTGCCGCTGTCGCAGCGGCTGACCGGTGCC

GTCGACGCCGAGGCACTGCGCGCCGCCCTCGCCGATGTCGTCACCCGGCACGTTCCGCTG

CGCACGCTCGTCCAGGACGACGGCAGCGGTCCGTGTGCGGTGATCACGGAAGCCACCGCG

GACGACATCCCATGGACGGAGACCAGGACCACGCCCGAGCGGCTGTCCGAGGATCTCGCG

CACGCCGCCCGCCGCCACTTCGACCTCGAGACCGAGATCCCGCTGCGGGCCGTACTGTTC

ACGCTCGGCCCGGACGAGTCCGTACTGCTGCTGGTCATGCATCACATCGCCGCCGACGGC

TGGTCCTTCGGCCCCCTGCTGGAGGACCTGGTCCGCGCCTACCGCGCCCGGACCGAGGGG

CGCGCACCACAGTGGGAGCCGCTGTCCTTCGGCTACCTCGACTACGTCGCCTGGCAGCGC

-continued

CGGCTGCTCGGCGCCACGGACGACCCGAGCGACGTCGCGCTGCGCCAGGCGGAGTACTGG

AGGAAGACGCTGCACGGTGCCGACGACAGGCCGGTCCTGGAGACCGACAGCCCGGCGCCG

GCCCAGCAGGACTTTGCCGGCAGGTCCCTCGATCTTCCGCTCGAAGTCGGCGGCCACCGG

GTGCTGACAGCCGCGGCCCGTGAGCACGGTGTCACCGTCTTCATGATCCTGCACGCCGCG

CTCGTCGCACTGCTCGCCCGCAGGGGAGCAGGAGGGGACGTCACCGTCGTGACCGCGGTG

GCCGGCCGGACCGACACCCAGTTCGAACCGCTGGTGGGCCTCTTCGCCAACACCTTGGCG

CTGCGCACCGACACGTCGGGCAACCCCACCTTCCGCGAACTGCTGGACCGGGTCCGCGTG

ACCGATCTCGGTGCCTATGCCCACCAGGACCTGCTCTTCGAGCGCCTGGCCGACGTGCCA

CCGCCCCAGGTGTCACTCGTCCTGCGCACGGTCGCAGCTCCGCCGGCCGACCTGCCGGGC

CTCACCATCAGTCCCGGCCCACGGCCGGCGAGCGAATCCGCCCGCTATCCGGTGCTGTGG

ACCGTGGAGCATCTGGCCTCCGCCGCGGACGGCGGGACGCTGCGCAGCCACATCCAGTAC

CAGAGCGGGCTGCTGCGCGACGACACGGTCGTCCGGCTCGCCCAGCAGTACGAAGTCGTG

CTGTCCCTGTTGTTGAAGGATCCCGATCTCCGCGTCCAGGACCTCCCACTGCAGTGA

TxtA (scab31791)

(SEQ ID NO: 2)

VSHLTGEDLPEGALATTWPSLLEARVADTPDAIALVAGDTALTYAQFNARANRLARWLKY

LGAGPERSVGLVLGRSADFFLCATAVLKCGAAYLPLDPNYPVERLSFMARDAAPVVLVTT

SDVRGDLLGQLPTGSLVVLDDEATEDVLRRLPDHDMEDGERLEPLRPASPAYIIYTSGST

GIPKGVVVTHQGVASLIATQRRRLAVTGASRVLAFSSPSFDASFWEMSMALLAGAALVVG

RPGRLLPDAELAALIADHGVTHVTLPPSVAGALGPDMLPPSVTLVVAGEACPAALVQRWR

PHRTMVNAYGPTESTVCATMSDPLADDVAPPVGRAVDGTRIHVLDDRLAPVVPGAVGEIY

IAGHSLARGYLERPGLTAQRFVADPFGPAGSRMYRSGDLGRWTRSGDLEFVGRADDQVKV

RGFRIEPGEIESVIAGCRGVRQAAVVLREDRPGEPYLAAYVIPENAAADEAAGEEPDGQL

DAWRRLYDDLYGRADTADFGEDFSGWVSSYGGRPIEGMREWREQTVRQIRELAPRRVLEI

GCGSGLLLSQLAGDCESYWGTDISGALIERLRGQVAERPGLADRVVLHQLSAHELGSLPS

GGFDTVVLNSVIQYFPSGDYLFDLLREVSRLLVPGGAVFLGDVRNLRLLRTFHAGGLLAA

ATHTDTPQTVCAAIDRAMAQEKELLVDPEFFTTAVGALPGMTLESCTLKRGGYDNELSRY

RYEVVLRKHAGPADDTGPTDDAGPVVRLRWDGEMASLADVADRLRRGKPERLCVTGIPNG

RVAGEHAATLALFDRRPLHEVLSLGQAPAGVAPEDLRRLGAELGYRVDCTWSSEDDALID

ASFTRAGALVPRPAPRTDAEPDGFSPARFTNRPAFARPDSQTMASLPGQVAAKLPAFMVP

EVFVPLDRLPVTVNGKLDRGALPRPRRAAHASGRPPRTAREEVLAAIFADVLATADVTAD

SDFFAVGGNSLLATRLAAEVRRRLNTEMPLSWLFESPTVGALAARFDAGDEARPLPVPSE

YASGSTAPLSAQQMQMWHEYRRSLCRDMFNVPLSQRLTGAVDAEALRAALADVVTRHVPL

RTLVQDDGSGPCAVITEATADDIPWTETRTTPERLSEDLAHAARRHFDLETEIPLRAVLF

TLGPDESVLLLVMHHIAADGWSFGPLLEDLVRAYRARTEGRAPQWEPLSFGYLDYVAWQR

RLLGATDDPSDVALRQAEYWRKTLHGADDRPVLETDSPAPAQQDFAGRSLDLPLEVGGHR

VLTAAAREHGVTVFMILHAALVALLARRGAGGDVTVVTAVAGRTDTQFEPLVGLFANTLA

LRTDTSGNPTFRELLDRVRVTDLGAYAHQDLLFERLADVPPPQVSLVLRTVAAPPADLPG

LTISPGPRPASESARYPVLWTVEHLASAADGGTLRSHIQYQSGLLRDDTVVRLAQQYEVV

LSLLLKDPDLRVQDLPLQ

-continued txtB (scab31781)

(SEQ ID NO: 3)

ATGTCCATGCTGCCGCCGGGGCGAAGCCGCACCACGGCCTCGCCCGCCGGGGCCCAGGCC

GGCCCCGAGTTCACCCCCGGCCTATGGGGACGGCTCTTCGAAGCCCGTGTCGACGCCGCC

CCCGAATCCACCGCGATCAACTCCGCGAGCGAGCGGCTGAGTTACGCCGAACTGAACCGG

CGGGCCAACCGCCTCGCCAGGTTGCTCATCGCACGTGGCGCCGGCCCGGAGAGCCTGGTC

GGTCTCGCCCTGCCGCGCTCGACCGACTTCGTGGTGGCCGTGGCGGCCGTACTGAAATCG

GGCGCCGGCTACTTCCCGATGGATCCGGACTATCCTCCGCAGCGGCTGGCGTTCATGCTC

GCCGACGCCGCTCCCATGCTGGTGCTGACCAGGAGTGACATCGAGCCCGAGCTGCCGGCC

GAGGCGGCCTCCCGCACGGTGGTGCTGGACGACCCGGCCGTCGTACGGACCCTGGCCGAC

TGCTCCGCGGCGGATGTGGCGGACGACGAACGCGGCGCCCCGCTCCGGACCCGGCATCCG

GCCTATGTCATCTACACCTCGGGTTCCACCGGTACTCCCAAAGGAGTGGTCCTCACCCAC

CACGGCATCGCCAGCCTGGTGGGCAGCCATGCGCGGGACCTGGGGATCGGGCCGTCCAGC

CGGTTGCTGCTCTTTTCCTCGCCGAGTTTCGACGGCGCCTTCTGGGACGTGTCGATGGCC

TTGCTCACTGGCGCCACGCTGGTGGTCGCACCGCGTGAACGGCTCCTGCCCGGACCGGAG

TTCAGTGCGCTCGCCGCCGAGGAGGGCATCACCCACTTCACCCTGCCGGCCTCCACGCTC

GCCGCCCTGCCGGACGGCGCTCTGCCCGCCGGGGCCACCGTCGTCAATGTGGGCGAGGCC

TGCAACAGCGAGCTGGTGCGCCGCTGGTCGCCGGGCCGGCTGCTGGTGAACGCGTACGGA

CCGACCGAATCGACCGTCTCCGCGACCATGAGCGGACCGTTGGCCGGGGCAGGCATCCCG

CCCATCGGCCGTCCGCTCTCGGACACCCGCATCCACGTCCTCGACGAGCGGCTCCGGCCG

GTACCGCCGGGAGCGGTCGGAGAGATCCACATCGCCGGAGCGGGGCTGGCCCGCGGGTAC

CTGGGGCGGCCCGCGCTGACCGCCGAGCGGTTCGTGGCCGACCCCTTCGGGACGCCGGGC

GAGCGGATGTACCGGACCGGCGACCGGGTGAGGGTGCGTGACGACGGGCAACTGGAGTTC

GTGGGCCGGGTCGACGACCAGGCGAAGATACGGGGTTTCCGAGTGGAGCCCGGCGAGGTC

GAAGCCGTGCTGCGCGACCATCCCGAGGTCGCGCAGGCCGCGGTGGTGGTCCGGGAGGAC

ACTCCGGGAGACCAGAGGCTCGTCGCCTATGTCGTGCCGGACCACCCGGCCGTGCGGCAG

GCCGACGACACCACCTCGGAGCACGTCGAGGAATGGCAACGGCTCTACGACGAGGTCTAC

AGCGCAGTGGGAGCGCTCCCCCTGGGGGAGGACTTCAGCGGCTGGAACAGCACCTACGAC

GGCGAGCCCATTCCCGTGCCTCAGATGCAAGCCTGGCGGGACGCCACGGTCGACAGCATC

CGTGCCCTGCGACCGCGCCGGGTACTGGAGATCGGCGTGGGCACCGGGCTGCTGCTGTCC

CGCCTCGCCGGTGACTGCGAGGCGTACTGGGCCACCGACTTCTCCGCCGAGGTGATCGAG

ACACTCGGCAAGAAGGTGGACGTCGACCCGGTGCTGCGGGAGAAGGTCCACCTGCTGCAC

GGTCCCGCACACGACCTCCCCGGCCTCCCCGAGGGGTACTTCGACACCGTTGTCCTCAAC

TCGGTGATCCAGTACTTTCCGTCGGCCGACTACCTGGTGAGCGTCCTGCGCGAGGCGGCA

CGCCTGCTGGCGCCGGGCGGCCGGGTGTTCGTCGGCGACATCCGGCACCTGCGTCTGCTG

CGCCCGCTGCGCAGCGCCGTCCGGCTGCGCTCCGCCACCCGGCGGGAAGCCTCTGCCTCC

GCCGTCCGCGCGGCGGTCGAGCAGGACCTGGTGGATGAGAAGGAGTTGCTCCTCGACCCC

GCGTTCTTCGCCGCGGTACCCCGGTGGATCCCGCAGCTCCGCGGGGTACGCACAGCGGTG

CAGCGCGGCACGCACCACAACGAACTGACCCGCTACCGGTACGACGCGGTGCTCATCAAG

GAGCCGGTGGAAACCGGTACCGCTGCGCCGGACGCGCAGACACTGACCTGGGGCACGGAT

GTCAGCGGACTGCAGGAGTTGTCCGGCCTGCTGGCCCGCACCCGCACGTCGCTGCTGCTG

-continued

CGCGGCGTGCCGAACAGCCGGATCCTCGGTGAGGCATCGGCCGCGACGGCGCTGACCACG

GCCCGGTCGCTCGACGAGCCGTTGCGGTTGCTGCAAGAACCGGCGGCAGGGATCGACCCC

GAGGAACTGCACGCCCTGGGCGGGGGCGCCGGCTGCGAGGTCCACCTCACGTGGTCGGCG

CAGGACCCCACGCGACTGGACGCCTGTTTCACACCCGTGGGCGGTGAACCGGGCGCCGTC

CCGCTGGCGGAGTCCGCCGACAGCGGCAGGACGTCGCCCGGTGACCACGCCAACCAGCCG

ACCACGCACCGGACCGGCAACGCCCTGATGGGCAAGCTCCCCGGCTATCTGGCCGCCAGG

CTCCCCGCGTACCTGCGGCCCAGCGCCGTGGTACGCATCGCGTCGCTCCCCCTCACCGTC

AACGGCAAGCTCGACCGCACGGCGCTGCCCCGTCCCGCCCTGTTCCCGCGGGCTGACGGG

CAGGCGCCCCGCACTCCGCGCGAGGAGATCCTCGCCAATCTCTTCGCCGATGTGCTCGGC

CTGCCCGGGGTGCCGAGGGACGCCGACTTCTTCGCCCTGGGCGGCAACTCGCTACTGGCC

ACGCGCCTCGTCGGCCGTATCGCGAAACACCTCGAAGTCGATGTTCCGATCGCCTGGATC

TTCGAGACACCGACCGTCGAGGGCCTGGCCGGGCGTACCGCTCCGGCGAGCAGGCTCCGC

CCGCTGTTGCTCTGCCGCGACGAGAACCACGCGGCGGTGCCGCTCTCGCACAGCCAGTAC

GGCATGTGGTTCATCAACCAACTCGGCGGACCCGCGAGCCGGATCTACAACGTGCCGTAC

TGCCTGCGGATCACGGGCCGGGTGGACACCGGGGCGCTGCGGACCGCACTCGATGACGTC

GTGGCTCGTCACGAACCCCTGCGTACCGTCTTCCCCGATGACGGTGACGGCCCCCGCCAA

CGGGTCCTCGCCCCCGAGGACGCCGCGGTGGTCCTTCATGAGACCGACGCCGCCGAAGAC

CGTCTGGCCGGCCACCTGGCGCGGGCCGCGGCGGAACCCTTCGAGCTCAGGACGGACCTT

CCCCTGCGCGCACGCCTGTTCCGGCACGGACAGGACCGGTACACGCTCCTGCTCCTGATG

CACCACATCACCGTGGACGCCTGGTCGCTGGCCCCCCTGACGGCGGACCTGGCGCACGCC

TACCGGGCGCGGCTGGGGCAGCGGGCCCCGCAGTGGCAGCCGCTGCCGGTTCACTATCGC

GACTACGCCGTATGGCACAACGAGCAAGCAGCCGAGGCGCAGGACCGCGGCAGCGGCTTC

GGGCGCCAGCTCGCCTTCTGGGAGCGGACGCTGCGCGGTCTTCCGGTCGAGACGCGGCTG

CCGGCCGACCGGAGCCGTCCGGCCAGACCTACCTATCGTGGCGGCACCGTCCACACCCAC

GTCGAAGCCTCCCTCCATCAGGAACTGCTCAACTGCGCGCGGGAGACGGGCGCGACGCTC

TTCATGGTGCTGCACGCCGCGCTCGCGGCACTGCTGACCCGGCTGGGCGGCGGCACCGAC

ATCGTCGTCGGCACCGCTGCCGCGGCGCGCACGGACCCCGCGCTGGACGACCTCGTCGGG

CTGTTCGCCAACAGTGTCGTCCTTCGCGTCGACACCTCGGGCGACCCGACGTTCCGCACC

CTGCTCGCTCGGACCCGGGCCGTGGACCTCGACGCCTTCACCCACCAGGAGGTCCCGTTC

GACCAGGTGGTGGATCGCGTCAACCCGGCACGCCACCCGGCACGTCACCCGCTCTACCAG

ACGGCCCTCGTCCTGCACGCACCGCCCGGCGACGGCCATCGGGCCGACTCCGTCACCCTC

ACCCCCGAACCGCCCCCGAACACCGGAACGGCCCGCTTCGATCTGATGTTCAACTGGGAC

GAGAGCCGGGACAGCGCCGGCCTCGCCCAGGGCCTCACCGGCCGTACCGAGTACAGCTCG

GACCTCTTCTCCCAGGAGACAGTCGAACTGCTCCTGGAGCGGTATCTCCTGCTGCTGTCC

GCCGCGGTCCGCGACCCGGACGCACGCCTTCACACCCTGGACATCCTCACCGAGCCGGAA

CGGCGGGCCTTCTCACCACGGCCGTAG

TxtB (scab31781)

(SEQ ID NO: 4)

MSMLPPGRSRTTASPAGAQAGPEFTPGLWGRLFEARVDAAPESTAINSASERLSYAELNR

RANRLARLLIARGAGPESLVGLALPRSTDFVVAVAAVLKSGAGYFPMDPDYPPQRLAFML

ADAAPMLVLTRSDIEPELPAEAASRTVVLDDPAVVRTLADCSAADVADDERGAPLRTRHP

AYVIYTSGSTGTPKGVVLTHHGIASLVGSHARDLGIGPSSRLLLFSSPSFDGAFWDVSMA

-continued

LLTGATLVVAPRERLLPGPEFSALAAEEGITHFTLPASTLAALPDGALPAGATVVNVGEA
CNSELVRRWSPGRLLVNAYGPTESTVSATMSGPLAGAGIPPIGRPLSDTRIHVLDERLRP
VPPGAVGEIHIAGAGLARGYLGRPALTAERFVADPFGTPGERMYRTGDRVRVRDDGQLEF
VGRVDDQAKIRGFRVEPGEVEAVLRDHPEVAQAAVVVREDTPGDQRLVAYVVPDHPAVRQ
ADDTTSEHVEEWQRLYDEVYSAVGALPLGEDFSGWNSTYDGEPIPVPQMQAWRDATVDSI
RALRPRRVLEIGVGTGLLLSRLAGDCEAYWATDFSAEVIETLGKKVDVDPVLREKVHLLH
GPAHDLPGLPEGYFDTVVLNSVIQYFPSADYLVSVLREAARLLAPGGRVFVGDIRHLRLL
RPLRSAVRLRSATRREASASAVRAAVEQDLVDEKELLLDPAFFAAVPRWIPQLRGVRTAV
QRGTHHNELTRYRYDAVLIKEPVETGTAAPDAQTLTWGTDVSGLQELSGLLARTRTSLLL
RGVPNSRILGEASAATALTTARSLDEPLRLLQEPAAGIDPEELHALGGGAGCEVHLTWSA
QDPTRLDACFTPVGGEPGAVPLAESADSGRTSPGDHANQPTTHRTGNALMGKLPGYLAAR
LPAYLRPSAVVRIASLPLTVNGKLDRTALPRPALFPRADGQAPRTPREEILANLFADVLG
LPGVPRDADFFALGGNSLLATRLVGRIAKHLEVDVPIAWIFETPTVEGLAGRTAPASRLR
PLLLCRDENHAAVPLSHSQYGMWFINQLGGPASRIYNVPYCLRITGRVDTGALRTALDDV
VARHEPLRTVFPDDGDGPRQRVLAPEDAAVVLHETDAAEDRLAGHLARAAAEPFELRTDL
PLRARLFRHGQDRYTLLLLMHHITVDAWSLAPLTADLAHAYRARLGQRAPQWQPLPVHYR
DYAVWHNEQAAEAQDRGSGFGRQLAFWERTLRGLPVETRLPADRSRPARPTYRGGTVHTH
VEASLHQELLNCARETGATLFMVLHAALAALLTRLGGGTDIVVGTAAAARTDPALDDLVG
LFANSVVLRVDTSGDPTFRTLLARTRAVDLDAFTHQEVPFDQVVDRVNPARHPARHPLYQ
TALVLHAPPGDGHRADSVTLTPEPPPNTGTARFDLMFNWDESRDSAGLAQGLTGRTEYSS
DLFSQETVELLLERYLLLLSAAVRDPDARLHTLDILTEPERRAFSPRP txtC (scab31761)

(SEQ ID NO: 5)

ATGGAATCTCCGGCCACCCAGGTCGACCCGGCGAACTCGCCGTTGGAGCCCTATCACATC
TACCCGGAGGCCAAGTCCTGCCCGGTGGCGAAGGTCGGTCTGTGGAACGGCACGCCGGCG
CACGTGTTCTCCGGGTATGAGGATGTGCGGACCGTGCTGCAGGACAGGCGGTTCAGCTCG
GACTCGCGCCGACCCAACTTCACCGAACTCACTCCGACGCTCCAGTCGCAGGCCGCGGCA
CCGCCGTTCGTACGCACCGACAATCCTGATCACCGGCGCCTGCGAGGCACCATCGCACGC
GAGTTCCTGCCCAAGCACATCGAGCTGCTGCGCCCCGCGATCCGCGAGATCGTCCAGGGT
GTGCTCGACGGGCTCGCCGAGACCGCGCCTCCCCAGGACATGCTCGAGGCCTTCGCCGTA
CCGGTCGCGTCCGCGACCGTCTTCCGGCTGCTGGGGATTCCGGCCGAGGACCGCGCGTTG
CTCACCCGATGCGTCAAGGGCGTGGTCTCGGCGGTGGGGAGCGAGGACGAAGGTGCCGAG
GTGTTCCGGACACTCGGCGAGTACATCGGCGGGCTCGTCCAGGACCCCTCCGAACTGCCC
GAGGACAGCCTGATCCGGCGCCTGGTGACGGGCCCGTACCAGGAGAAGCAGCTCACCTTC
CACGAGACCATCGGCGTGATCCTCATGCTCATCGTCGGGGGCTACGACACGACGGCCAGC
ACCATCTCGCTGTCCTTGGTGAGTTATGCACTGCAGCCGGAGAAGTTCTCCGTCGTCCAC
GAACACCCGGAGCGGATACCCCTGCTCGTCGAGGAGTTGCTGCGCTATCACACCGTCTCG
CAGCTCGGACTGGGCAGGATCGCCACCGAGGACGTCGAGGTGGGCGGCGTCACGGTGCGG
GCCGGCCAGATGGTGGTGGCGGCGCTCCCCCTGGCCAACCGGGACGAGAGTGTCTTCCCG
AACCCGGACGAACTCGACTTCGACCGCCCGTCCGTGCCCCATGTCGGCTTCGGTTACGGA
CCCCACCAGTGCGTCGGCCAGGCACTGGCCCGAGTCGAACTCCAGGAGGCCATTCCCGCG

-continued

GTGATCCGACGGCTGCCCGGCATGCGGCTCGCCTGCGCTCTGGAAGACCTGCCGTTCCGG

CACGACATGGCCACCTACGGCATCCATGAGCTGCCCATGACCTGGTGA

TxtC (scab31761)

(SEQ ID NO: 6)

MESPATQVDPANSPLEPYHIYPEAKSCPVAKVGLWNGTPAHVFSGYEDVRTVLQDRRFSS

DSRRPNFTELTPTLQSQAAAPPFVRTDNPDHRRLRGTIAREFLPKHIELLRPAIREIVQG

VLDGLAETAPPQDMLEAFAVPVASATVFRLLGIPAEDRALLTRCVKGVVSAVGSEDEGAE

VFRTLGEYIGGLVQDPSELPEDSLIRRLVTGPYQEKQLTFHETIGVILMLIVGGYDTTAS

TISLSLVSYALQPEKFSVVHEHPERIPLLVEELLRYHTVSQLGLGRIATEDVEVGGVTVR

AGQMVVAALPLANRDESVFPNPDELDFDRPSVPHVGFGYGPHQCVGQALARVELQEAIPA

VIRRLPGMRLACALEDLPFRHDMATYGIHELPMTW txtD (scab31841)

(SEQ ID NO: 7)

TTGCCCGCCCCGTCCCCGACAGCGTGCCCGGCACTGGGGCCCGATTCGTCCCTTGGCCCG

GTCCCGTCGGCGGAACCGGCGACGCCGCAGTCCTGCGGCGTCGCCGATCCAAATGAGGCT

GAGGAGTTCCTGCGCCAGTTCCACGCGGAGCAGTCCGATCAGCCCGTCCCGCTCGCCCGG

CGCCTGGAGCAGGTCCGCGCCGCCATCGACGCCACGGGCACCTACCGGCACACCACCGCC

GAGCTCGTGTACGGTGCCCGCGTCGCGTGGCGCAACTCCAGTCGCTGCATCGGCCGCCTG

TACTGGAACAGCCTGCGCGTCCTGGACCGCCGGGACGCCACAGCCCCCGATGAGATCCAC

CGGCACTTGTGCACGCACCTGCGCCAGGCGACCAACGGCGGGCGCATCAGGCCGGTGATT

TCGGTCTTCGCCCCGGACTCCCCCGGCCGGCCCGGCCCGCAGGTGTGGAACGAGCAGCTC

ATCCGGTACGCCGGCTACCGCCGCGACGACGGCACCGTGCTCGGTGACCCGCGCACCGCC

GACCTCACCGAGGCCATCCTCCGCCTCGGCTGGCAGGGCTGCCCCCAAGGGCCGTTCGAC

GTCCTGCCCCTGGTCATCGACACCCCCGACGACAAACCCCGGTTCTTCGAGCTGCCGCGG

GAGCTGGTCTTGGAGGTCCCTATCACCCACCCCGACGTCCCACGCCTGGCCGAACTGGGC

CTGCGCTGGCACGCCGTACCCGTCATCTCCAACATGCGCCTACGCATCGGCGGGATGGAC

TACCCGCTCGCCCCGTTCAACGGCTGGTACATGGGCACGGAGATCGGCGCCCGCAACCTC

GTCGACGAGGACCGCTACAACATGCTCCCCGCCGTCGCCGCCTGCCTCCAGCTGGACACC

ACCAGCGAGTCAACCCTGTGGCGCGACCGCGCCCTGGTCGAGCTCAACGTCGCCGTCCTG

CACTCCTTCGAGGCCGCAGGTGTCCGGATCAGCGACCACCACGAGGAGTCCCGGCGCTTC

CTCGCCCACCTGGCCAAGGAGGAACGCCAGGGCCGCACCGTATCCGCAGACTGGAGCTGG

ATCGTCCCCCCGCTCTCCGGCGGCATCACCCCCGTGTTCCACCGTTACTACGACAACGTC

GACCAGCGCCCCAACTTCTACCCCCACCAGTGA

TxtD (scab31841)

(SEQ ID NO: 8)

LPAPSPTACPALGPDSSLGPVPSAEPATPQSCGVADPNEAEEFLRQFHAEQSDQPVPLAR

RLEQVRAAIDATGTYRHTTAELVYGARVAWRNSSRCIGRLYWNSLRVLDRRDATAPDEIH

RHLCTHLRQATNGGRIRPVISVFAPDSPGRPGPQVWNEQLIRYAGYRRDDGTVLGDPRTA

DLTEAILRLGWQGCPQGPFDVLPLVIDTPDDKPRFFELPRELVLEVPITHPDVPRLAELG

LRWHAVPVISNMRLRIGGMDYPLAPFNGWYMGTEIGARNLVDEDRYNMLPAVAACLQLDT

TSESTLWRDRALVELNVAVLHSFEAAGVRISDHHEESRRFLAHLAKEERQGRTVSADWSW

IVPPLSGGITPVFHRYYDNVDQRPNFYPHQ

-continued txtE (scab31831)

(SEQ ID NO: 9)

GTGACCGTCCCCTCGCCGCTCGCCGACCCGTCCATCGTGCCCGACCCCTACCCTGTCTAC

GCCGACCTGGCCCAGCGCCGCCCCGTCCACTGGGTCGAGCGCCTGAACGCCTGGGCGGTC

TTGACGTACGCCGACTGCGCCGCCGGGCTGAAGGATCCCCGGCTCACCGCCGACCGGGGG

ACGGAAGTGCTGGCCGCGAAGTTCCCCGGACAGCCGCTGCCGCCGGACAACATCTTCCAC

CGCTGGACCAAGAACGTGGTGATGTACACGGACCCGCCGCTCCACGACGCGCTACGCCGG

TCCGTCCGCGCAGGCTTCACCCGTGCCGCGCACCAGCACTACGACCAAGTCCTCCAGAAG

GTCGCGCACGACCTGGTCGCTTCCATCCCGGCCGGTGCCACCGAGATCGACGCCGTCCCC

GCCCTGGCTGCCGAACTCCCCGTACGCTCCGCCGTGCACGCCTTCGGGGTCCCCGAGGAG

GACCTCGGATTCCTCATCCCGCGCGTGAATACGATCATGACGTACCACTCCGGTCCGAAG

GATCAGCCGGTGACGCAGGAGATAATCCTGGAAAAGCTCACCGACCTGCACACGTACGCC

TCCGAACTCCTCCAGGGCATGCGGGGCAAGGTCCTGCCGGACACCGTCATCGCCCGCCTG

GCAGCCGCCCAGGACGGCCTGACCGAGACCACGCCGGAACAGACCGTGCACCAGCTGGCG

CTGGTGTTCATCGCGTTGTTCGCGCCCACGACGCCGGGCTCTCTCAGCAGCGGCACGCTC

GCGTTCGCCCGCAACCCGCGGCAGGTCGAACGCTTCCTGGCGGACCAGGCGTGCGTGGAC

AACACGGCGAACGAGGTCCTCCGCTACAACGCCTCGAACCAGTTCACCTGGCGCGTCGCG

GCCAAGGACGTCGAGATGGGCGGCGTACGGATCGAGGCCGGGCAGACTCTCGCCCTGTTC

CTGGGCTCGGCCAACCGGGACGCCAACATGTTCGAGCGACCGAACGACTTCGACCTCGAC

CGTCCCAACAGCGCTCGGCACCTGTCGTTCGGCCAAGGGGTGCACGCCTGTCTCGCCGCG

CAGCTCATCTCCCTGCAGCTGAAGTGGTTCTACGTCGCCCTGCTGAACCGCTTCCCGGGC

ATCCGGACGGCGGGCGAGCCGATCTGGAACGAGAACCTCGAATTCCGCTCCCTTCGCTCC

CTGCCGCTCAGCCTCCGCTGA

TxtE (scab31831)

(SEQ ID NO: 10)

VTVPSPLADPSIVPDPYPVYADLAQRRPVHWVERLNAWAVLTYADCAAGLKDPRLTADRG

TEVLAAKFPGQPLPPDNIFHRWTKNVVMYTDPPLHDALRRSVRAGFTRAAHQHYDQVLQK

VAHDLVASIPAGATEIDAVPALAAELPVRSAVHAFGVPEEDLGFLIPRVNTIMTYHSGPK

DQPVTQEIILEKLTDLHTYASELLQGMRGKVLPDTVIARLAAAQDGLTETTPEQTVHQLA

LVFIALFAPTTPGSLSSGTLAFARNPRQVERFLADQACVDNTANEVLRYNASNQFTWRVA

AKDVEMGGVRIEAGQTLALFLGSANRDANMFERPNDFDLDRPNSARHLSFGQGVHACLAA

QLISLQLKWFYVALLNRFPGIRTAGEPIWNENLEFRSLRSLPLSLR txtH (scab31771)

(SEQ ID NO: 11)

GTGCCCTCACCCTTCGACGACCATGACGGGCAGTTCCATGTGCTCCGCAACGAGGAAGGC

CAGTTCTCACTCTGGCCGAATTTCGCCGACATCCCCTCCGGGTGGCGTTCCGTGAGCGGG

CCGAGCCCCCGCGGAAGCGCCCTTGAGTACATCGAGAAGGAATGGACGGACATGCGCCCG

GCGTCCGTCCGTGAATGA

TxtH (scab31771)

(SEQ ID NO: 12)

VPSPFDDHDGQFHVLRNEEGQFSLWPNFADIPSGWRSVSGPSPRGSALEYIEKEWTDMRP

ASVRE

-continued txtR (scab31801)

(SEQ ID NO: 13)

ATGACGGACGGCGACGTTCCCTTTTCGATGAATGTGCCCGTTGCTTCGCGACTCCTCGTACTGC

GTTTCGCCGACGAAGCGAAGGATGGACTCCCGGTGTCGCCTCGGGGGACTTTTATCGTGACGGA

TGCTGCCAAGGGTCCCGGATCCGGATTTCTTTTTTCGTTCTTGAATACCCTGGCTGTGGAGATGA

TGAAAACCGATGGGATTCTGTCCTCGTATATGGAGGAGGTCGTGCGCATCCTGGCGATCTCCGC

GACGCGAATCGCATATGCCGAGCTCGGAAAGCATTACTCTGGGGGATGCGATCCACTTCTGATC

GCGGTTCAGGAGTCGATCGACCGGCAGTTGGCCGACCCCGAGATCAGCCCGGCGACCCTCGCG

GCCGAACACAACATATCGGTGCGTCAGTTACATCGAGTTTTCGGACCGATCGGGGAAAGCGTCA

TGAGCTATGTCAAACGCCGTCGCCTGGAGCGTTTCGCATGCGATCTGAGGGATCCGAGCCTGGG

GCACCGGAAGATCAATGAGCTGGCGGCGGACTGGGGGATGCTGGATGCCGCGATGCTGAGCAG

ACACTTCCGCTGCGCCTACGGAATGTCGCCCCGCGATTACCGGAAGCAGCACTGTTTCACCTGA

TxtR (scab31801)

(SEQ ID NO: 14)

MTDGDVPFSMNVPVASRLLVLRFADEAKDGLPVSPRGTFIVTDAAKGPGSGFLFSFLNTLAVEMMKT

DGILSSYMEEVVRILAISATRIAYAELGKHYSGGCDPLLIAVQESIDRQLADPEISPATLAAEHNIS

VRQLHRVFGPIGESVMSYVKRRRLERFACDLRDPSLGHRKINELAADWGMLDAAMLSRHFRCAYGMS

PRDYRKQHCFT

Promoter sequences (from *Streptomyces albus* J1074)

P1

(SEQ ID NO: 15)

CTCGTGAGGCTAGCTCCGCCGCGGACCCCGCTCGCGCCGGGGCCCGCCGAACGGTGCCGGGC

GCGCGGCGCCACGAGTACGGCAGGTGTACCGTTGTCAACGCCTGACCTGCGGCAATCAAACATC

CGGGTGAAGTGATCTTTCCCTCTACCGGTGCCGAGCTTCTGCGTGCTAGGCTCGCCGCAAGTTG

CAGTTTGGTTTCCCTTGCAGTACAGAGCCTGCGGAGCATGTGACCGCAGGCTCTCGTCATTTTCA

GACTTTTGCACTTGTTTTCACACTTGCAGGTTCTGGAGCAGGGCAACCCTTTGGCCCAAGGAGGG

CTT

P6

(SEQ ID NO: 16)

GGCGCCGACCGCACCACACTCACGAGGGCCCGCCCCACCAACAGGGGGCGGGCCCTCTGTGC

TGGCCTCAGGCGCCGACCGGGCTCGGTGCCCTCAAGCGCCGGCCGGGCTCCAAGGGTGGCCT

CAAGCGCCGGCCGGGCTGAGTTGGGCCGGTCTGGGCCCGCACGCGCGCCTCACTGACGGCCT

CAAGCGCCGGCCGGGCTATCTATAGCCCGGCCGGCGCTTGAGGCCGTCTTTGGCGCGCGCCTG

TGAGCGGACGGCCCGTCAAAGATCAGCCCGGCCGGCGCTTGAGGCCATCTTTCGAGCCCGGCC

GGCGTTTGAGGCCACCCCACCCCCGCCCCGGCAGGGGCGGCCTGACCTCCGCATCCGCCGGC

GCGGACAGGGCACCCCCAGTAGACGGGCGCGGGGCCGGAGGCCCCTAGCGCCTTGCACTCTC

CTACCCCGAGTGCTAATTATTGGCGTTAGCACTCTCCGAGTGAGAGTGACAGAAGGACCGGGTCG

GTGAGGCCCGCTGGCCACGCGGGGCAAGGAACCGCGAGGCAGGCAGGCCGTCCGTCGCGGG

CGCCAGCACGGTCCGGAGTATCCACCCTCCCCCAGACAGAGTCCGGGGGGACCCCCAGTCCTG

GGAGGACCACTTCA

P7

(SEQ ID NO: 17)

TCCAGAGATGTCCGGCGTGCGCGTCCCGTGGGGCGCGTGGGCCGGCGGATTCGTCCGTCCGG

GCGGGTCCTGCGACGGTCTGCGGCCGGGACGCATAAGGATCAGCGCATCGGGGCATTGTTCCTC

GATTCGCCTTTTGCGGGAGCCCTGGCGTAGACTGACGCGTCGGCTCTCGTGCACCCGTATGTCC

GTATGGATGTGCAAGGGACACGGAGCCGGTCAAGGTAGTCGATTCGAAGGGCGAAG

-continued

P8

(SEQ ID NO: 18)

TACGGCACCTCCTGCGGAAGCGGCGCTCACCTCGGTGCGGGGCACCGGTGCTGCGCATCCGGT

GCCGAAGCACCCGATATACCCAGATTGCGGGCATCGGCGGCCGGATTTCAACCGGAAGCGGTCG

TGCGGGTACTCTGTACCGTCTGCACCGGTGTCTGCCCAGATCCTGGATCACCCGCTCACCACGG

CTCCCGCTCGCGGGGTCCGCCGTCAGCGGTGGCCGATACCGTTGCGCTCGCATCAAGACCCTC

CTGCCACGGAACGACCGTGGCCGCTGAGTCCAAAGGAGGTGGGTTCTA

P9

(SEQ ID NO: 19)

TCCGCTCCTCCGGGCGGGGTCCGCGGATCCCGCCCGGAGGCCGTGCTTCCGGGCGATTTGCCT

CGCGCCGCCCGGCTCCCGTACTCTTCCCTAGAAGCCAAAGACCGCTGGTCGTTACCGTCTGCTC

CTCGGAGAGGGCGGTGGCCGAAGGATTCCGCTCACGCGGACGGCCTGCGTAGGTGACTGTGGA

TGTGCTCCTGGACGTGTTACGGCCAGTCGAGCTCACGCCCCGTGCGCCTGCGCCGGGGCGTTT

TTCGTCTTACGCAGACTTTCCTGCCCGACGTCCTTCCTCACGTGCCTGATCCAGACGGTCCCAGT

GCTGTACGAGGCTGATCGCAAGGTCAGTCGAGGATCATCACCCCGGAAGGAGGCCGAGGCT

P10

(SEQ ID NO: 20)

CGCACACCTGCTCTCGCAGATCACGCGCGACGCACAGCAGTATCACCAAACGCAGTGCCCGCCT

CTTCCCGTGTCCTGAACACGTGAGAAGGGCGGTACCCCCGGTCGGAGGCCGGGGACCCGTTCC

GTTCCATGCCCCTCGGCGGCTCCGTCCGCCCCGGTGGATCGGCGGTCGGGAGCGGCACTGCG

GCAGACCTCCGACAGACAACTGGAGCCATTAG

P11

(SEQ ID NO: 21)

ATCCCGCTCTTCAGGGATTCACCGGGCCTCTGGTAAGCAACCAGGCGGCGGACGATCTTCCTCC

GATGGCTTAGGCTGGAGAGGTTGGCCGTCCGCCGCCCTGGACAGCCCGCGGACGCTCACCACT

GAGCAGTCCGCATATGACGCTTACTACGCCGCAGGTCCCCGCGCCGCACCCGTCCCGTCCCGGA

TCGGGGAGAGGGATGGCGCATACAGGAAACCCCGGCGAGAAAGGCCGAAGGCCGATT

P13

(SEQ ID NO: 22)

GAGTGCTCCTGCCTCGGGACCGGCGGACAAGCGGCCGGTCTGATCATCGGGGCAGCAACATATG

ACTCCGGCACATGTCAGGGAGCTCCGAACGGGTGCGTTCACCCTGATGGGGGAGTACGGGAGC

GCCCGTGCGGAAGATCCTCGAAGGGTGTCCCGCCCTCGTTCGGCCGCGTCCGCGTTTGACGGC

GGGAAGGCCGGGGGTAAGCTTCTCGGCTCGATTGGCTCTACGCGGGGCCCGTGTGGCAGACTG

TCCGGGTTGCTCGGTTGAGTGCCGATGCCGCGCGCCTCCCGCCGGGAGGACTGGAAGCGAGTC

CCACAGTACTCGTCGCCTCAACTGCCCCAGGTTCGCCGAAGGCAGCGCTGTGGCGGACGTACG

GGAATCTTCCGGGAAGCGTGTGCGGGGTACCAGCCAGGCGCCCGGTGGTCACCACACCGCAAG

GTGTGGCTTCACCGAACCGCGTGGCCACGGTGTGGAACGCAGCCCCCCAGATGGGATTCCGCG

AGGAAATTTCGTACGGGCGGGAAGGCGACACACCCGACCGCGTGGGTCGGAGAGAGAGACCGG

ACCCCGGGTCCCAGAGCGTTACGAGAGACAGGACTACCAAGTAGC

P20

(SEQ ID NO: 23)

CGGGAATTGTGCCGGGTTTGCGGCTTGCGCCCCGGGTGTGCGCCTTCGCGCATTGACCCTGTCC

GGCTGCCCCCGTATGCTACAAGTTGCGCTGCGAGCCTGCGCTCCTCAGACCTAGCAGGATGTGC

TCGCTTCTGTTGTGTGTCCCCTCGGTTGTACGAGGCGAGGACCCCCGGTTTCCCGGAGGTCGCG

CCTCTGAAGGCTGTCCGACTGCTGCAGAGTGAAACCGGCTCCGTGCGCGGCAGTACCTACGACT

TCATGTCCGTACCGGAGCCCTTTCCCA

-continued

P23

(SEQ ID NO: 24)

CGGGACCTCGGCGACCACCTTGTCGAGCAGCGCCTCGACGCCCAGGCCGGTCTTGGCGGAGAC

CTTGAGCACGTCGGAGGGGTCGCGTGGTCCTGGTTCTTGAGACGTCGAGACGTCGAGGCGGGC

GGGCGGCGCGGAGCCGGACGGGGGCAGTAGGCGCCTCACCTCGGGTGGGCTCACGCCGCCTG

GGCGCGCCCACCGGGCCGGCACACGACCCCCGGGGTCCGCGGCCCCCATCGTCCCATGCGCG

GGGACCGGCGACCGGTTTGGGCCGCGCGTGGGGCCGCTGGTAGCCTGGCCCGATGTGTCTCGT

AGCCCTCTCAGCGTCGGGACACGACCGGAAACACCCAACCTGAACCTGTAAAGGCTCTTT

P24

(SEQ ID NO: 25)

CGGCCCCCTCCCCGTGGTTCCCCGTTCCCCGTCCGCGCCCGCGTGGCCCGTACGGCGGTACGG

ACGGGGCGGGACGGGTCAACGTACTGACCCCCCGGCCCAGGTGGCCCGCCCTTGACCGGAATG

AATCCCCCCGCCCCGCTACTCGGCGGGAAAGCTGCGCTCTGTGGCCGAAAACACACAGAGGGT

GGGAGGGGGCGTGCCGGGGGCCGGCGAACGATTCCGGCCAGGGTGCCCCTGGCACCACCCG

GCGGCCCGGTGTAGCGTCCCCCGCGGGACCAGAAGACGATCATGCAGCGGAGGGCGCCGGTC

CGCCCCGGGGTACGGGGCGTCTGACCAGCCCGTCCGCTGCGCGTGCATTTGTTTTGACCGAACT

CCGTGCGATAGGTACGCTCAGACCTTGTGCCTGGGGTGTGCCTGGGCTCCCGTGCGTGTCCAAC

CCGCGCGGCGAGCGTCAGGCGTCAGCACCGCAATCTGCGCTTCTCCCGTGTGCTAGCGGGGCT

CCGCGGTATTCGACACACCCGACCGCGTGGGTCGGGAGTGTTCCAGGTTAGCTTTACCTGTTCG

GCACACAGAAACCGGAGAAGTA

P28

(SEQ ID NO: 26)

TGCCCGCTCCCTCTTCACGTCCCGACGGCGAAACCGGCCGCCCAGTCTGCCGTGCCCGGCCCG

GTCCCACCACCTCCTCCGGCGGACGCCCCCCGAAGGAGCGGACCCGCCCCCGACTTCCGGCC

GGCGGCGCCCCCGACCTCGTAGAACCCCGCCCGAGCGCCCGGCGTCAACCTCGCGCCCACGC

GTCACCCGGCCCCTTCCCGGCTGCGGCGCGACCGGCTCCCCGCCCCTGCTACTCTGTCCGAGG

CCGTCTGTGCCCACGTCCCGAGCCCCGCGTTCGACACGCGGTCCCGGACGACCGGACGGATCC

ATCCGCCTCCCGAGTCACCGAAGCCTCCCCTGAGACGAAGACCAGGGGCGCTCGGAGGCAAGC

GAAGACATCACAGAGGAGTACG

P31

(SEQ ID NO: 27)

CCGGACCTCTCCTCACGCTCACCCTGCGCGCTTCCGCGCGACAGGCACAATTACCCGTATATGTC

CCGACTCGCCCACAGTCTCCGCCTTCGGCCGGGTCATTCCCCCGACCGACCCGGCCCGGCCCA

CCCATTTCCGGCCCGGCCGGCGTTTGAGGCCGACCGGTGACGGACACCCGAAGCCCTCGGAGC

GCGCTCGGCATCAGCCCGGACGACGCTTGAGGCCACCTCGACCGCCGCCGGACGGCTTCATCC

GAAGTGCCTCTGAACTGGTAAAACGAGCCGTGCTGGCAGCTCTCTGCACAACCAGGCAGAACAA

AACTTGAGCCCGTCCGACTCAACCGCATTGACGCGCCGCGTCCCCTCGTGCATCCTTGAGTGAG

TTCCACTCAAGTAGTCAGCTGGAGGAATTGA

Ksaop*

(SEQ ID NO: 28)

TGTTCACATTCGAACGGTCTCTGCTTTGACAACATGCTGTGCGGTGTTGTAAAGTCGTGGCCAGG

AGAATACGACAGCGTGCAGGACTGGGGGAGTT

P6E-P1D (SEQ ID NO: 29)

GGCGCCGACCGCACCACACTCACGAGGGCCCGCCCCACCAACAGGGGGCGGGCCCTCTGTGC

TGGCCTCAGGCGCCGACCGGGCTCGGTGCCCTCAAGCGCCGGCCGGGCTCCAAGGGTGGCCT

CAAGCGCCGGCCGGGCTGAGTTGGGCCGGTCTGGGCCCGCACGCGCGCCTCACTGACGGCCT

-continued

```
CAAGCGCCGGCCGGGCTATCTATAGCCCGGCCGGCGCTTGAGGCCGTCTTTGGCGCGCGCCTG

TGAGCGGACGGCCCGTCAAAGATCAGCCCGGCCGGCGCTTGAGGCCATCTTTCGAGCCCGGCC

GGCGTTTGAGGCCACCCCACCCCCGCCCCGGCAGGGGCGGCCTGACCTCCGCATCCGCCGGC

GCGGACAGGGCACCCCCAGTAGACGGGCGCGGGGCCGGAGGCCCCTAGCGCCTTGCACTCTC

CTACCCCGAGTGCTAATTATTGGCGTTAGCACTCTCCGAGTGAGAGTGACAGAAGGACCGGGTCG

GTGAGGCCCGCTGGCCACGCGGGGCAAGGAACCGCGAGGCAGGCAGGCCGTCCGTCGCGGG

CGCCAGCACGGTCCGGAGTATCCACCCTCCCCCAGACAGAGTCCGGGGGGACCCCCAGTCCTG

GGAGGACCACTTCA
```

REFERENCES

Wach, M. J.; Krasno, S. B.; Loria, R.; Gibson, D. M. *Arch Microbiol.* 2007, 188, 81-88.

King, R. R. *Canadian Journal of Chemistry,* 1997, 75, 1172-1173.

Molesworth, P. P.; Gardiner, M. G.; Jones, R. C.; Smith, J. A.; Tegg, R. S.; Wilson, C. *Aust. J. Chem.* 2010, 63, 813-820

Zhang, H.; Ning, X.; Hang, H.; Ru, X.; Li, H.; Li, Y.; Wang, L.; Zhang, X.; Yu, S.; Qiao, Y.; Wang, X.; Wang, P. G. *Org. Lett.* 2013, 15, 5670-5673.

Zhang, H.; Wang, Q.; Ning, X.; Hang, H.; Ma, J.; Yang, X.; Lu, X.; Zhang, J.; Li, Y.; Niu, C.; Song, H.; Wang, X.; Wang, P. G. J. *Agric. Food Chem.* 2015, 63, 3734-3741.

Bourgault, J. P.; Maddirala, A. R.; Andreana, P. R. *Org. Biomol. Chem.* 2014, 12, 8125-8127.

Healy, F. G.; Krasnoff, S. B.; Wach, M.; Gibson, D. M.; Loria R. *J. Bacteriol.* 2002, 184, 2019-2029.

Zaburannyi, N.; Rabyk, M.; Ostash, B.; Fedorenko, V.; Luzhetskyy, A. *BMC Genomics.* 2014, 15, 97.

Bilyk, O.; Sekurova, O. N.; Zotchev, S. B.; Luzhetskyy, A. *PLoS One.* 2016, 11, 7.

Feng, Z.; Wang, L.; Rajski, S. R.; Xu, Z.; Coeffet-LeGal, M. F.; Shen, B. *Bioorg. Med. Chem.* 2009, 17, 2147-2153.

Luo, Y.; Zhang, L.; Barton, K. W.; Zhao, H. ACS *Synth. Biol.* 2015, 4, 1001-1010.

Johnson, E. G.; Joshi, M. V.; Gibson, D. M.; Loria, R. *Physiol Mol Plant Path.* 2007, 71, 18-25.

We claim:

1. A genetically engineered *Streptomyces* bacterium from a naturally non-pathogenic *Streptomyces* strain, the genetically engineered *Streptomyces* bacterium comprising:

an exogenous, refactored thaxtomin biosynthetic gene cluster comprising one or more thaxtomin modules, each thaxtomin module comprising:

one or more thaxtomin genes from a thaxtomin biosynthetic gene cluster from a plant pathogenic *Streptomyces* bacterium, the one or more thaxtomin genes selected from the group consisting of: a txtA gene encoding a TxtA protein, a txtB gene encoding a TxtB protein, a txtC gene encoding a TxtC protein, a txtD gene encoding a TxtD protein, a txtE gene encoding a TxtE protein, and a txtH gene encoding a TxtH protein, wherein the exogenous, refactored thaxtomin biosynthetic gene cluster as a whole comprises two or more thaxtomin genes, and one or more promoters operably linked to the one or more thaxtomin genes in the one or more thaxtomin modules, such that expression of the one or more thaxtomin genes in the exogenous, refactored thaxtomin biosynthetic gene cluster provides the genetically engineered *Streptomyces* bacterium with the ability to produce at least one thaxtomin compound in the absence of thaxtomin-inducing conditions, wherein the naturally non-pathogenic *Streptomyces* strain without the exogenous refactored thaxtomin cluster does not have the ability to produce the thaxtomin compound.

2. The genetically engineered *Streptomyces* bacterium of claim 1, wherein the refactored thaxtomin biosynthetic gene cluster comprises at least two thaxtomin modules.

3. The genetically engineered *Streptomyces* bacterium of claim 2, wherein the at least two thaxtomin modules comprise: a first module, module 1, comprising a txtE and a txtD biosynthetic gene and a second module, module 2, comprising a txtA, a txtB, and txtH biosynthetic gene, and wherein the at least one thaxtomin compound is selected from the group consisting of thaxtomin A, thaxtomin D, and combinations thereof.

4. The genetically engineered *Streptomyces* bacterium of claim 3, further comprising a third module, module 3, comprising a txtC biosynthetic gene, and wherein the at least one thaxtomin compound comprises thaxtomin A.

5. The genetically engineered *Streptomyces* bacterium of claim 3, wherein none of the thaxtomin modules comprise txtC and wherein the at least one thaxtomin compound comprises thaxtomin D.

6. The genetically engineered *Streptomyces* bacterium of claim 1, wherein the pathogenic *Streptomyces* strain is selected from the group of plant pathogenic *Streptomyces* species consisting of: *Streptomyces scabiei, Streptomyces acidiscabies*, and *Streptomyces turgidiscabies.*

7. The genetically engineered *Streptomyces* bacterium of claim 1, wherein the *Streptomyces* bacterium from a naturally non-pathogenic *Streptomyces* strain is *S. albus.*

8. The genetically engineered *Streptomyces* bacterium of claim 1, wherein the refactored thaxtomin biosynthetic gene cluster is operably linked to a nucleotide sequence encoding at least one selectable marker.

9. The genetically engineered *Streptomyces* bacterium of claim 1, wherein the refactored thaxtomin biosynthetic gene cluster comprises at least two thaxtomin modules and wherein the one or more thaxtomin genes in each module are different from the one or more thaxtomin genes in each other module.

10. The genetically engineered *Streptomyces* bacterium of claim 1, wherein each module comprises one or more promoters, one or more ribosomal binding site, and one or more terminators, wherein the promoter for each module can be the same or different.

11. The genetically engineered *Streptomyces* bacterium of claim 1, wherein the one or more promoter in each module is independently selected from the group of constitutive promoters consisting of: P1, P6, P7, P8, P9, P10, P11, P13, P20, P23, P24, P28, P31, and Ksaop*.

12. A method of producing a thaxtomin compound, the method comprising:

culturing a plurality of genetically engineered *Streptomyces* bacteria of claim 1 in the absence of thaxtomin-inducing conditions, such that expression of the refactored thaxtomin biosynthetic gene cluster provides the genetically engineered *Streptomyces* bacterium with the ability to produce at least one thaxtomin compound in the absence of thaxtomin-inducing conditions.

13. The method of claim 12, further comprising extracting the thaxtomin compound from the culture medium.

14. The method of claim 12, wherein culturing the genetically engineered *Streptomyces* bacteria in the absence of thaxtomin-inducing conditions comprises culturing the genetically engineered *Streptomyces* bacteria in a culture medium that does not contain cellobiose and does not contain oat bran broth (OBB).

15. The method of claim 12, wherein the one or more thaxtomin modules comprise a txtE biosynthetic gene, a txtD biosynthetic gene, a txtA biosynthetic gene, a txtB, and a txtH biosynthetic gene and one or more promoters operably linked to the biosynthetic genes.

16. The method of claim 15, wherein the one or more thaxtomin modules further comprise a txtC biosynthetic gene and wherein the at least one thaxtomin compound is thaxtomin A.

17. The method of claim 15, wherein none of the thaxtomin modules comprise txtC and wherein the at least one thaxtomin compound comprises thaxtomin D.

18. A refactored thaxtomin biosynthetic gene cluster consisting of:

one or more thaxtomin modules, each thaxtomin module consisting of:

one or more thaxtomin genes from a thaxtomin biosynthetic gene cluster from a pathogenic *Streptomyces* bacterium, the one or more thaxtomin genes selected from the group consisting of: a txtA gene encoding a TxtA protein, a txtB gene encoding a TxtB protein, a txtC gene encoding a TxtC protein, a txtD gene encoding a TxtD protein, a txtE gene encoding a TxtE protein, and a txtH gene encoding a TxtH protein, wherein the refactored thaxtomin biosynthetic gene cluster as a whole comprises two or more thaxtomin genes, one or more ribosomal binding sites, one or more terminators, and one or more promoters operably linked to the one or more thaxtomin genes, wherein the one or more promoters are not under the control of a natural thaxtomin inducer.

19. The genetically engineered *Streptomyces* bacterium of claim 1, wherein the txtA gene comprises the nucleotide sequence of SEQ ID NO: 1, the txtB gene comprises the nucleotide sequence of SEQ ID NO: 3, the txtC gene comprises the nucleotide sequence of SEQ ID NO: 5, the txtD gene comprises the nucleotide sequence of SEQ ID NO: 7, the txtE gene comprises the nucleotide sequence of SEQ ID NO: 9, and the txtH gene comprises the nucleotide sequence of SEQ ID NO: 11.

20. The genetically engineered *Streptomyces* bacterium of claim 1, wherein the TxtA protein comprises the amino acid sequence of SEQ ID NO: 2, the TxtB protein comprises the amino acid sequence of SEQ ID NO: 4, the TxtC protein comprises the amino acid sequence of SEQ ID NO: 6, the TxtD protein comprises the amino acid sequence of SEQ ID NO: 8, the TxtE protein comprises the amino acid sequence of SEQ ID NO: 10, and the TxtH protein comprises the amino acid sequence of SEQ ID NO: 12.

* * * * *

SEQUENCE LISTING

```
<160> NUMBER OF SEQ ID NOS: 29

<210> SEQ ID NO 1
<211> LENGTH: 4377
<212> TYPE: DNA
<213> ORGANISM: Streptomyces scabies

<400> SEQUENCE: 1

gtgtcgcacc tgaccggtga agatctcccg gagggagcgc tcgccacgac gtggccgagt      60

ctcctcgaag cgcgggtggc cgacacacct gacgccatcg cgctcgtcgc cggggacacg     120

gcgctcacgt acgcgcagtt caatgcccgt gcgaaccggc tcgcccggtg gctgaagtac     180

ctcggcgccg ggccggagcg gtcggtcggg ctggtgctgg gcaggtccgc ggacttcttc     240

ctgtgcgcga cggccgtgct caagtgcggg gccgcgtacc tgccgctgga tccgaactac     300

cccgtggagc gactgtcctt catggcccgg gacgcagcac ccgtggtgct ggtgacgacg     360

tcggacgtcc ggggcgacct tctgggccag ctgcccaccg gcagcctcgt ggtactggac     420

gacgaggcca ccgaggacgt actgcgccgt ctgccggacc acgacatgga ggacggggaa     480

cgtttggagc cactgcgccc cgcgagtccc gcctacatca tctacacctc cggctccacg     540

gggatcccca agggagtcgt cgtcacccac caaggcgtcg cgagcctgat cgcgacccag     600

cgtcgtcgcc tcgccgtcac cggcgcctca cgcgtgctcg ccttctcgtc cccgagtttc     660

gacgccagtt tctgggagat gtcgatggcg ctgctggccg gggccgcgct cgtggtcggc     720

aggccggggc ggctgctgcc cgacgccgaa ctggccgcgt tgatcgcgga ccacggagtc     780

actcatgtca ctctcccgcc ctcggtcgcg ggtgcgctgg gccccgacat gctgcctccg     840

agcgtgacgc tggtcgtcgc gggcgaagcg tgcccggcgg ctctcgtgca gcgctggcgc     900
```

-continued

```
ccgcaccgga cgatggtgaa cgcctacggc ccgacggagt ccaccgtctg cgccaccatg    960
agcgatccgc tggccgacga cgtggcgccg ccggtcggcc gggcggtgga cggcacccgg   1020
atccatgtcc tcgacgaccg cctcgcaccg gttgtgccgg gagcggtcgg cgagatctac   1080
atcgcggggc acagcctggc acgcgggtac ctcgagcggc cgggtctgac cgcgcagcgg   1140
ttcgtggcgg accccttcgg cccggccggc agccgtatgt accgcagcgg tgacctcggc   1200
cgctggaccc gttcaggaga cctggagttc gtcggcaggg cggacgacca ggtcaaggta   1260
cgcggcttcc gtatcgagcc gggcgagatc gaatccgtca tcgccgggtg ccgcggggtc   1320
cggcaggccg ccgtcgtcct gcgtgaggac cggcccggag agccatacct cgccgcctac   1380
gtcatacccg agaacgcggc cgccgacgag gcggccggcg aggaaccgga cggtcaactc   1440
gatgcctggc gacggctcta cgacgatctg tacggccgag ccgacaccgc cgacttcggc   1500
gaggacttct ccggctgggt gagcagttat ggcgggcggc cgatcgaggg gatgcgcgaa   1560
tggcgtgagc agaccgtgcg gcagatccgc gaactggctc cgcgccgcgt actggagatc   1620
ggctgcggtt ccggtctgct gctctcgcag ctggcgggtg actgcgaaag ctactggggc   1680
accgacatct ccggggccct gatcgagcgg ctgcgcgggc aggtcgccga gcgccccggc   1740
ctcgcggacc gggtcgtcct gcatcagctc tccgcccatg agctggggag tctgcccagc   1800
ggcggcttcg acaccgtcgt gctcaactcc gtgatccagt actttccctc aggcgattac   1860
ctgttcgacc tactgcgcga ggtgtcccgg ctcctggtac ccgggggcgc ggtgttcctc   1920
ggcgacgtcc gtaaccttcg tctgctgcgc accttccacg ccgggggggct gctggcggcg   1980
gccacgcaca ccgacactcc gcagacggtc tgcgcggcga tcgaccgggc catggcgcag   2040
gagaaggaac tgctcgtgga cccggagttc ttcacgacgg ccgtcggcgc gctgcccggc   2100
atgacgctgg agtcgtgcac gctcaaacgg ggcgggtacg acaacgaact cagccgctat   2160
cgctacgagg tggtgctgcg caagcatgcc gggcctgccg atgacaccgg gcccacggac   2220
gacgcggggc cggtcgtgcg actgcggtgg gacggcgaga tggcgagcct ggccgacgtc   2280
gccgatcggc tgcgtcgtgg gaaaccggag cggttgtgcg tcaccgggat ccccaacggc   2340
cgggtggccg gcgagcatgc cgcgacactc gcgctgttcg accggcgccc cctgcacgag   2400
gtgctgtccc tggggcaggc tccggcgggc gtggcaccgg aggacctgcg ccggctgggc   2460
gcggaactgg gctaccgggt cgactgcacc tggtcgtccg aggacgacgc cctgatcgac   2520
gcttccttca cacgcgccgg agcgctcgtg ccgcgtcccg ccccccggac cgacgcggag   2580
ccggacggtt tctccccggc ccggttcacc aacaggccgg cgttcgcccg ccccgactcc   2640
cagacgatgg cctctcttcc cgggcaggtc gcggcgaagc tgccggcctt catggtcccg   2700
gaggtcttcg tcccgctcga caggctgccg gtcacggtga acggaaagct cgaccgcggc   2760
gccctgcccc ggccgcggcg cgccgcccat gcctcgggac gtccgcccag gaccgcccgc   2820
gaggaggtac tggcggcgat cttcgccgac gtactcgcga cagccgacgt cacagccgac   2880
agcgacttct tcgccgtcgg cggcaactcc ctgctggcca cccgactcgc cgccgaggtc   2940
cggcggcgcc tgaacaccga gatgccgctg tcgtggctgt tcgagtcgcc caccgtcggc   3000
gcgctcgccg cccgcttcga cgcgggggac gaggccaggc cgctgcccgt gccgagcgag   3060
tacgcctccg gcagcacggc gccgttgtcg gcccagcaga tgcagatgtg gcacgagtac   3120
cgccgaagcc tgtgtcgcga catgttcaac gtgccgctgt cgcagcggct gaccggtgcc   3180
gtcgacgccg aggcactgcg cgccgccctc gccgatgtcg tcacccggca cgttccgctg   3240
cgcacgctcg tccaggacga cggcagcggt ccgtgtgcgg tgatcacgga agccaccgcg   3300
```

-continued

```
gacgacatcc catggacgga gaccaggacc acgcccgagc ggctgtccga ggatctcgcg   3360

cacgccgccc gccgccactt cgacctcgag accgagatcc cgctgcgggc cgtactgttc   3420

acgctcggcc cggacgagtc cgtactgctg ctggtcatgc atcacatcgc cgccgacggc   3480

tggtccttcg gccccctgct ggaggacctg gtccgcgcct accgcgcccg gaccgagggg   3540

cgcgcaccac agtgggagcc gctgtccttc ggctacctcg actacgtcgc ctggcagcgc   3600

cggctgctcg gcgccacgga cgacccgagc gacgtcgcgc tgcgccaggc ggagtactgg   3660

aggaagacgc tgcacggtgc cgacgacagg ccggtcctgg agaccgacag cccggcgccg   3720

gcccagcagg actttgccgg caggtccctc gatcttccgc tcgaagtcgg cggccaccgg   3780

gtgctgacag ccgcggcccg tgagcacggt gtcaccgtct tcatgatcct gcacgccgcg   3840

ctcgtcgcac tgctcgcccg caggggagca ggaggggacg tcaccgtcgt gaccgcggtg   3900

gccggccgga ccgacaccca gttcgaaccg ctggtgggcc tcttcgccaa caccttggcg   3960

ctgcgcaccg acacgtcggg caaccccacc ttccgcgaac tgctggaccg ggtccgcgtg   4020

accgatctcg gtgcctatgc ccaccaggac ctgctcttcg agcgcctggc cgacgtgcca   4080

ccgccccagg tgtcactcgt cctgcgcacg gtcgcagctc cgccggccga cctgccgggc   4140

ctcaccatca gtcccggccc acggccggcg agcgaatccg cccgctatcc ggtgctgtgg   4200

accgtggagc atctggcctc cgccgcggac ggcgggacgc tgcgcagcca catccagtac   4260

cagagcgggc tgctgcgcga cgacacggtc gtccggctcg cccagcagta cgaagtcgtg   4320

ctgtccctgt tgttgaagga tcccgatctc cgcgtccagg acctcccact gcagtga      4377
```

<210> SEQ ID NO 2
<211> LENGTH: 1458
<212> TYPE: PRT
<213> ORGANISM: Streptomyces scabies

<400> SEQUENCE: 2

```
Val Ser His Leu Thr Gly Glu Asp Leu Pro Glu Gly Ala Leu Ala Thr
1               5                   10                  15

Thr Trp Pro Ser Leu Leu Glu Ala Arg Val Ala Asp Thr Pro Asp Ala
            20                  25                  30

Ile Ala Leu Val Ala Gly Asp Thr Ala Leu Thr Tyr Ala Gln Phe Asn
        35                  40                  45

Ala Arg Ala Asn Arg Leu Ala Arg Trp Leu Lys Tyr Leu Gly Ala Gly
    50                  55                  60

Pro Glu Arg Ser Val Gly Leu Val Leu Gly Arg Ser Ala Asp Phe Phe
65                  70                  75                  80

Leu Cys Ala Thr Ala Val Leu Lys Cys Gly Ala Ala Tyr Leu Pro Leu
                85                  90                  95

Asp Pro Asn Tyr Pro Val Glu Arg Leu Ser Phe Met Ala Arg Asp Ala
            100                 105                 110

Ala Pro Val Val Leu Val Thr Thr Ser Asp Val Arg Gly Asp Leu Leu
        115                 120                 125

Gly Gln Leu Pro Thr Gly Ser Leu Val Val Leu Asp Asp Glu Ala Thr
    130                 135                 140

Glu Asp Val Leu Arg Arg Leu Pro Asp His Asp Met Glu Asp Gly Glu
145                 150                 155                 160

Arg Leu Glu Pro Leu Arg Pro Ala Ser Pro Ala Tyr Ile Ile Tyr Thr
                165                 170                 175

Ser Gly Ser Thr Gly Ile Pro Lys Gly Val Val Val Thr His Gln Gly
```

```
            180                 185                 190

Val Ala Ser Leu Ile Ala Thr Gln Arg Arg Arg Leu Ala Val Thr Gly
        195                 200                 205

Ala Ser Arg Val Leu Ala Phe Ser Ser Pro Ser Phe Asp Ala Ser Phe
    210                 215                 220

Trp Glu Met Ser Met Ala Leu Leu Ala Gly Ala Ala Leu Val Val Gly
225                 230                 235                 240

Arg Pro Gly Arg Leu Leu Pro Asp Ala Glu Leu Ala Ala Leu Ile Ala
                245                 250                 255

Asp His Gly Val Thr His Val Thr Leu Pro Pro Ser Val Ala Gly Ala
            260                 265                 270

Leu Gly Pro Asp Met Leu Pro Pro Ser Val Thr Leu Val Val Ala Gly
        275                 280                 285

Glu Ala Cys Pro Ala Ala Leu Val Gln Arg Trp Arg Pro His Arg Thr
    290                 295                 300

Met Val Asn Ala Tyr Gly Pro Thr Glu Ser Thr Val Cys Ala Thr Met
305                 310                 315                 320

Ser Asp Pro Leu Ala Asp Asp Val Ala Pro Pro Val Gly Arg Ala Val
                325                 330                 335

Asp Gly Thr Arg Ile His Val Leu Asp Asp Arg Leu Ala Pro Val Val
            340                 345                 350

Pro Gly Ala Val Gly Glu Ile Tyr Ile Ala Gly His Ser Leu Ala Arg
        355                 360                 365

Gly Tyr Leu Glu Arg Pro Gly Leu Thr Ala Gln Arg Phe Val Ala Asp
    370                 375                 380

Pro Phe Gly Pro Ala Gly Ser Arg Met Tyr Arg Ser Gly Asp Leu Gly
385                 390                 395                 400

Arg Trp Thr Arg Ser Gly Asp Leu Glu Phe Val Gly Arg Ala Asp Asp
                405                 410                 415

Gln Val Lys Val Arg Gly Phe Arg Ile Glu Pro Gly Glu Ile Glu Ser
            420                 425                 430

Val Ile Ala Gly Cys Arg Gly Val Arg Gln Ala Ala Val Val Leu Arg
        435                 440                 445

Glu Asp Arg Pro Gly Glu Pro Tyr Leu Ala Ala Tyr Val Ile Pro Glu
    450                 455                 460

Asn Ala Ala Ala Asp Glu Ala Ala Gly Glu Glu Pro Asp Gly Gln Leu
465                 470                 475                 480

Asp Ala Trp Arg Arg Leu Tyr Asp Asp Leu Tyr Gly Arg Ala Asp Thr
                485                 490                 495

Ala Asp Phe Gly Glu Asp Phe Ser Gly Trp Val Ser Ser Tyr Gly Gly
            500                 505                 510

Arg Pro Ile Glu Gly Met Arg Glu Trp Arg Glu Gln Thr Val Arg Gln
        515                 520                 525

Ile Arg Glu Leu Ala Pro Arg Arg Val Leu Glu Ile Gly Cys Gly Ser
    530                 535                 540

Gly Leu Leu Leu Ser Gln Leu Ala Gly Asp Cys Glu Ser Tyr Trp Gly
545                 550                 555                 560

Thr Asp Ile Ser Gly Ala Leu Ile Glu Arg Leu Arg Gly Gln Val Ala
                565                 570                 575

Glu Arg Pro Gly Leu Ala Asp Arg Val Val Leu His Gln Leu Ser Ala
            580                 585                 590

His Glu Leu Gly Ser Leu Pro Ser Gly Gly Phe Asp Thr Val Val Leu
        595                 600                 605
```

-continued

```
Asn Ser Val Ile Gln Tyr Phe Pro Ser Gly Asp Tyr Leu Phe Asp Leu
    610                 615                 620

Leu Arg Glu Val Ser Arg Leu Leu Val Pro Gly Gly Ala Val Phe Leu
625                 630                 635                 640

Gly Asp Val Arg Asn Leu Arg Leu Leu Arg Thr Phe His Ala Gly Gly
                645                 650                 655

Leu Leu Ala Ala Ala Thr His Thr Asp Thr Pro Gln Thr Val Cys Ala
            660                 665                 670

Ala Ile Asp Arg Ala Met Ala Gln Glu Lys Glu Leu Leu Val Asp Pro
        675                 680                 685

Glu Phe Phe Thr Thr Ala Val Gly Ala Leu Pro Gly Met Thr Leu Glu
    690                 695                 700

Ser Cys Thr Leu Lys Arg Gly Gly Tyr Asp Asn Glu Leu Ser Arg Tyr
705                 710                 715                 720

Arg Tyr Glu Val Val Leu Arg Lys His Ala Gly Pro Ala Asp Asp Thr
                725                 730                 735

Gly Pro Thr Asp Asp Ala Gly Pro Val Val Arg Leu Arg Trp Asp Gly
            740                 745                 750

Glu Met Ala Ser Leu Ala Asp Val Ala Asp Arg Leu Arg Arg Gly Lys
        755                 760                 765

Pro Glu Arg Leu Cys Val Thr Gly Ile Pro Asn Gly Arg Val Ala Gly
    770                 775                 780

Glu His Ala Ala Thr Leu Ala Leu Phe Asp Arg Arg Pro Leu His Glu
785                 790                 795                 800

Val Leu Ser Leu Gly Gln Ala Pro Ala Gly Val Ala Pro Glu Asp Leu
                805                 810                 815

Arg Arg Leu Gly Ala Glu Leu Gly Tyr Arg Val Asp Cys Thr Trp Ser
            820                 825                 830

Ser Glu Asp Asp Ala Leu Ile Asp Ala Ser Phe Thr Arg Ala Gly Ala
        835                 840                 845

Leu Val Pro Arg Pro Ala Pro Arg Thr Asp Ala Glu Pro Asp Gly Phe
    850                 855                 860

Ser Pro Ala Arg Phe Thr Asn Arg Pro Ala Phe Ala Arg Pro Asp Ser
865                 870                 875                 880

Gln Thr Met Ala Ser Leu Pro Gly Gln Val Ala Ala Lys Leu Pro Ala
                885                 890                 895

Phe Met Val Pro Glu Val Phe Val Pro Leu Asp Arg Leu Pro Val Thr
            900                 905                 910

Val Asn Gly Lys Leu Asp Arg Gly Ala Leu Pro Arg Pro Arg Arg Ala
        915                 920                 925

Ala His Ala Ser Gly Arg Pro Pro Arg Thr Ala Arg Glu Glu Val Leu
    930                 935                 940

Ala Ala Ile Phe Ala Asp Val Leu Ala Thr Ala Asp Val Thr Ala Asp
945                 950                 955                 960

Ser Asp Phe Phe Ala Val Gly Gly Asn Ser Leu Leu Ala Thr Arg Leu
                965                 970                 975

Ala Ala Glu Val Arg Arg Arg Leu Asn Thr Glu Met Pro Leu Ser Trp
            980                 985                 990

Leu Phe Glu Ser Pro Thr Val Gly  Ala Leu Ala Ala Arg  Phe Asp Ala
        995                 1000                1005

Gly Asp  Glu Ala Arg Pro Leu  Pro Val Pro Ser Glu  Tyr Ala Ser
    1010                1015                1020
```

Gly Ser Thr Ala Pro Leu Ser Ala Gln Gln Met Gln Met Trp His
1025 1030 1035

Glu Tyr Arg Arg Ser Leu Cys Arg Asp Met Phe Asn Val Pro Leu
1040 1045 1050

Ser Gln Arg Leu Thr Gly Ala Val Asp Ala Glu Ala Leu Arg Ala
1055 1060 1065

Ala Leu Ala Asp Val Val Thr Arg His Val Pro Leu Arg Thr Leu
1070 1075 1080

Val Gln Asp Asp Gly Ser Gly Pro Cys Ala Val Ile Thr Glu Ala
1085 1090 1095

Thr Ala Asp Asp Ile Pro Trp Thr Glu Thr Arg Thr Thr Pro Glu
1100 1105 1110

Arg Leu Ser Glu Asp Leu Ala His Ala Ala Arg Arg His Phe Asp
1115 1120 1125

Leu Glu Thr Glu Ile Pro Leu Arg Ala Val Leu Phe Thr Leu Gly
1130 1135 1140

Pro Asp Glu Ser Val Leu Leu Leu Val Met His His Ile Ala Ala
1145 1150 1155

Asp Gly Trp Ser Phe Gly Pro Leu Leu Glu Asp Leu Val Arg Ala
1160 1165 1170

Tyr Arg Ala Arg Thr Glu Gly Arg Ala Pro Gln Trp Glu Pro Leu
1175 1180 1185

Ser Phe Gly Tyr Leu Asp Tyr Val Ala Trp Gln Arg Arg Leu Leu
1190 1195 1200

Gly Ala Thr Asp Asp Pro Ser Asp Val Ala Leu Arg Gln Ala Glu
1205 1210 1215

Tyr Trp Arg Lys Thr Leu His Gly Ala Asp Asp Arg Pro Val Leu
1220 1225 1230

Glu Thr Asp Ser Pro Ala Pro Ala Gln Gln Asp Phe Ala Gly Arg
1235 1240 1245

Ser Leu Asp Leu Pro Leu Glu Val Gly Gly His Arg Val Leu Thr
1250 1255 1260

Ala Ala Ala Arg Glu His Gly Val Thr Val Phe Met Ile Leu His
1265 1270 1275

Ala Ala Leu Val Ala Leu Leu Ala Arg Arg Gly Ala Gly Gly Asp
1280 1285 1290

Val Thr Val Val Thr Ala Val Ala Gly Arg Thr Asp Thr Gln Phe
1295 1300 1305

Glu Pro Leu Val Gly Leu Phe Ala Asn Thr Leu Ala Leu Arg Thr
1310 1315 1320

Asp Thr Ser Gly Asn Pro Thr Phe Arg Glu Leu Leu Asp Arg Val
1325 1330 1335

Arg Val Thr Asp Leu Gly Ala Tyr Ala His Gln Asp Leu Leu Phe
1340 1345 1350

Glu Arg Leu Ala Asp Val Pro Pro Pro Gln Val Ser Leu Val Leu
1355 1360 1365

Arg Thr Val Ala Ala Pro Pro Ala Asp Leu Pro Gly Leu Thr Ile
1370 1375 1380

Ser Pro Gly Pro Arg Pro Ala Ser Glu Ser Ala Arg Tyr Pro Val
1385 1390 1395

Leu Trp Thr Val Glu His Leu Ala Ser Ala Ala Asp Gly Gly Thr
1400 1405 1410

Leu Arg Ser His Ile Gln Tyr Gln Ser Gly Leu Leu Arg Asp Asp

-continued

```
    1415                1420                1425

Thr Val  Val Arg Leu Ala Gln  Gln Tyr Glu Val Val  Leu Ser Leu
    1430                1435                1440

Leu Leu  Lys Asp Pro Asp Leu  Arg Val Gln Asp Leu  Pro Leu Gln
    1445                1450                1455


<210> SEQ ID NO 3
<211> LENGTH: 4467
<212> TYPE: DNA
<213> ORGANISM: Streptomyces scabies

<400> SEQUENCE: 3

atgtccatgc tgccgccggg gcgaagccgc accacggcct cgcccgccgg ggcccaggcc     60

ggccccgagt tcacccccgg cctatgggga cggctcttcg aagcccgtgt cgacgccgcc    120

cccgaatcca ccgcgatcaa ctccgcgagc gagcggctga gttacgccga actgaaccgg    180

cgggccaacc gcctcgccag gttgctcatc gcacgtggcg ccggcccgga gagcctggtc    240

ggtctcgccc tgccgcgctc gaccgacttc gtggtggccg tggcggccgt actgaaatcg    300

ggcgccggct acttcccgat ggatccggac tatcctccgc agcggctggc gttcatgctc    360

gccgacgccg ctcccatgct ggtgctgacc aggagtgaca tcgagcccga gctgccggcc    420

gaggcggcct cccgcacggt ggtgctggac gacccggccg tcgtacggac cctggccgac    480

tgctccgcgg cggatgtggc ggacgacgaa cgcggcgccc cgctccggac ccggcatccg    540

gcctatgtca tctacacctc gggttccacc ggtactccca aaggagtggt cctcacccac    600

cacggcatcg ccagcctggt gggcagccat gcgcgggacc tggggatcgg gccgtccagc    660

cggttgctgc tcttttcctc gccgagtttc gacggcgcct tctgggacgt gtcgatggcc    720

ttgctcactg gcgccacgct ggtggtcgca ccgcgtgaac ggctcctgcc cggaccggag    780

ttcagtgcgc tcgccgccga ggagggcatc acccacttca ccctgccggc ctccacgctc    840

gccgccctgc cggacggcgc tctgcccgcc ggggccaccg tcgtcaatgt gggcgaggcc    900

tgcaacagcg agctggtgcg ccgctggtcg ccgggccggc tgctggtgaa cgcgtacgga    960

ccgaccgaat cgaccgtctc cgcgaccatg agcggaccgt tggccggggc aggcatcccg   1020

cccatcggcc gtccgctctc ggacacccgc atccacgtcc tcgacgagcg gctccggccg   1080

gtaccgccgg gagcggtcgg agagatccac atcgccggag cggggctggc ccgcgggtac   1140

ctggggcggc ccgcgctgac cgccgagcgg ttcgtggccg acccccttcgg gacgccgggc   1200

gagcggatgt accggaccgg cgaccgggtg agggtgcgtg acgacgggca actggagttc   1260

gtgggccggg tcgacgacca ggcgaagata cggggtttcc gagtggagcc cggcgaggtc   1320

gaagccgtgc tgcgcgacca tcccgaggtc gcgcaggccg cggtggtggt ccgggaggac   1380

actccgggag accagaggct cgtcgcctat gtcgtgccgg accacccggc cgtgcggcag   1440

gccgacgaca ccacctcgga gcacgtcgag gaatggcaac ggctctacga cgaggtctac   1500

agcgcagtgg gagcgctccc cctgggggag gacttcagcg gctggaacag cacctacgac   1560

ggcgagccca ttcccgtgcc tcagatgcaa gcctggcggg acgccacggt cgacagcatc   1620

cgtgccctgc gaccgcgccg ggtactggag atcggcgtgg gcaccgggct gctgctgtcc   1680

cgcctcgccg gtgactgcga ggcgtactgg gccaccgact tctccgccga ggtgatcgag   1740

acactcggca agaaggtgga cgtcgacccg gtgctgcggg agaaggtcca cctgctgcac   1800

ggtcccgcac acgacctccc cggcctcccc gaggggtact tcgacaccgt tgtcctcaac   1860

tcggtgatcc agtactttcc gtcggccgac tacctggtga gcgtcctgcg cgaggcggca   1920
```

-continued

```
cgcctgctgg cgccgggcgg ccgggtgttc gtcggcgaca tccggcacct gcgtctgctg   1980
cgcccgctgc gcagcgccgt ccggctgcgc tccgccaccc ggcgggaagc ctctgcctcc   2040
gccgtccgcg cggcggtcga gcaggacctg gtggatgaga aggagttgct cctcgacccc   2100
gcgttcttcg ccgcggtacc ccggtggatc ccgcagctcc gcggggtacg cacagcggtg   2160
cagcgcggca cgcaccacaa cgaactgacc cgctaccggt acgacgcggt gctcatcaag   2220
gagccggtgg aaaccggtac cgctgcgccg gacgcgcaga cactgacctg gggcacggat   2280
gtcagcggac tgcaggagtt gtccggcctg ctggcccgca cccgcacgtc gctgctgctg   2340
cgcggcgtgc cgaacagccg gatcctcggt gaggcatcgg ccgcgacggc gctgaccacg   2400
gcccggtcgc tcgacgagcc gttgcggttg ctgcaagaac cggcggcagg gatcgacccc   2460
gaggaactgc acgccctggg cgggggcgcc ggctgcgagg tccacctcac gtggtcggcg   2520
caggacccca cgcgactgga cgcctgtttc acacccgtgg gcggtgaacc gggcgccgtc   2580
ccgctggcgg agtccgccga cagcggcagg acgtcgcccg gtgaccacgc caaccagccg   2640
accacgcacc ggaccggcaa cgccctgatg ggcaagctcc ccggctatct ggccgccagg   2700
ctccccgcgt acctgcggcc cagcgccgtg gtacgcatcg cgtcgctccc cctcaccgtc   2760
aacggcaagc tcgaccgcac ggcgctgccc cgtcccgccc tgttcccgcg ggctgacggg   2820
caggcgcccc gcactccgcg cgaggagatc ctcgccaatc tcttcgccga tgtgctcggc   2880
ctgcccgggg tgccgaggga cgccgacttc ttcgccctgg gcggcaactc gctactggcc   2940
acgcgcctcg tcggccgtat cgcgaaacac ctcgaagtcg atgttccgat cgcctggatc   3000
ttcgagacac cgaccgtcga gggcctggcc gggcgtaccg ctccggcgag caggctccgc   3060
ccgctgttgc tctgccgcga cgagaaccac gcggcggtgc cgctctcgca cagccagtac   3120
ggcatgtggt tcatcaacca actcggcgga cccgcgagcc ggatctacaa cgtgccgtac   3180
tgcctgcgga tcacgggccg ggtggacacc ggggcgctgc ggaccgcact cgatgacgtc   3240
gtggctcgtc acgaacccct gcgtaccgtc ttccccgatg acggtgacgg cccccgccaa   3300
cgggtcctcg cccccgagga cgccgcggtg gtccttcatg agaccgacgc cgccgaagac   3360
cgtctggccg gccacctggc gcgggccgcg gcggaaccct tcgagctcag gacggacctt   3420
cccctgcgcg cacgcctgtt ccggcacgga caggaccggt acacgctcct gctcctgatg   3480
caccacatca ccgtggacgc ctggtcgctg gccccccctga cggcggacct ggcgcacgcc   3540
taccgggcgc ggctggggca gcgggccccg cagtggcagc cgctgccggt tcactatcgc   3600
gactacgccg tatggcacaa cgagcaagca gccgaggcgc aggaccgcgg cagcggcttc   3660
gggcgccagc tcgccttctg ggagcggacg ctgcgcggtc ttccggtcga gacgcggctg   3720
ccggccgacc ggagccgtcc ggccagacct acctatcgtg gcggcaccgt ccacacccac   3780
gtcgaagcct ccctccatca ggaactgctc aactgcgcgc gggagacggg cgcgacgctc   3840
ttcatggtgc tgcacgccgc gctcgcggca ctgctgaccc ggctgggcgg cggcaccgac   3900
atcgtcgtcg gcaccgctgc cgcggcgcgc acggaccccg cgctggacga cctcgtcggg   3960
ctgttcgcca acagtgtcgt ccttcgcgtc gacacctcgg gcgacccgac gttccgcacc   4020
ctgctcgctc ggacccgggc cgtggacctc gacgccttca cccaccagga ggtcccgttc   4080
gaccaggtgg tggatcgcgt caacccggca cgccacccgg cacgtcaccc gctctaccag   4140
acggccctcg tcctgcacgc accgcccggc gacggccatc gggccgactc cgtcaccctc   4200
acccccgaac cgcccccgaa caccggaacg gcccgcttcg atctgatgtt caactgggac   4260
```

```
gagagccggg acagcgccgg cctcgcccag ggcctcaccg gccgtaccga gtacagctcg   4320

gacctcttct cccaggagac agtcgaactg ctcctggagc ggtatctcct gctgctgtcc   4380

gccgcggtcc gcgacccgga cgcacgcctt cacaccctgg acatcctcac cgagccggaa   4440

cggcgggcct tctcaccacg gccgtag                                       4467


<210> SEQ ID NO 4
<211> LENGTH: 1488
<212> TYPE: PRT
<213> ORGANISM: Streptomyces scabies

<400> SEQUENCE: 4

Met Ser Met Leu Pro Pro Gly Arg Ser Arg Thr Thr Ala Ser Pro Ala
1               5                   10                  15

Gly Ala Gln Ala Gly Pro Glu Phe Thr Pro Gly Leu Trp Gly Arg Leu
            20                  25                  30

Phe Glu Ala Arg Val Asp Ala Ala Pro Glu Ser Thr Ala Ile Asn Ser
        35                  40                  45

Ala Ser Glu Arg Leu Ser Tyr Ala Glu Leu Asn Arg Arg Ala Asn Arg
    50                  55                  60

Leu Ala Arg Leu Leu Ile Ala Arg Gly Ala Gly Pro Glu Ser Leu Val
65                  70                  75                  80

Gly Leu Ala Leu Pro Arg Ser Thr Asp Phe Val Val Ala Val Ala Ala
                85                  90                  95

Val Leu Lys Ser Gly Ala Gly Tyr Phe Pro Met Asp Pro Asp Tyr Pro
            100                 105                 110

Pro Gln Arg Leu Ala Phe Met Leu Ala Asp Ala Ala Pro Met Leu Val
        115                 120                 125

Leu Thr Arg Ser Asp Ile Glu Pro Glu Leu Pro Ala Glu Ala Ala Ser
    130                 135                 140

Arg Thr Val Val Leu Asp Asp Pro Ala Val Val Arg Thr Leu Ala Asp
145                 150                 155                 160

Cys Ser Ala Ala Asp Val Ala Asp Asp Glu Arg Gly Ala Pro Leu Arg
                165                 170                 175

Thr Arg His Pro Ala Tyr Val Ile Tyr Thr Ser Gly Ser Thr Gly Thr
            180                 185                 190

Pro Lys Gly Val Val Leu Thr His His Gly Ile Ala Ser Leu Val Gly
        195                 200                 205

Ser His Ala Arg Asp Leu Gly Ile Gly Pro Ser Ser Arg Leu Leu Leu
    210                 215                 220

Phe Ser Ser Pro Ser Phe Asp Gly Ala Phe Trp Asp Val Ser Met Ala
225                 230                 235                 240

Leu Leu Thr Gly Ala Thr Leu Val Val Ala Pro Arg Glu Arg Leu Leu
                245                 250                 255

Pro Gly Pro Glu Phe Ser Ala Leu Ala Ala Glu Glu Gly Ile Thr His
            260                 265                 270

Phe Thr Leu Pro Ala Ser Thr Leu Ala Ala Leu Pro Asp Gly Ala Leu
        275                 280                 285

Pro Ala Gly Ala Thr Val Val Asn Val Gly Glu Ala Cys Asn Ser Glu
    290                 295                 300

Leu Val Arg Arg Trp Ser Pro Gly Arg Leu Leu Val Asn Ala Tyr Gly
305                 310                 315                 320

Pro Thr Glu Ser Thr Val Ser Ala Thr Met Ser Gly Pro Leu Ala Gly
                325                 330                 335
```

```
Ala Gly Ile Pro Pro Ile Gly Arg Pro Leu Ser Asp Thr Arg Ile His
            340                 345                 350

Val Leu Asp Glu Arg Leu Arg Pro Val Pro Pro Gly Ala Val Gly Glu
        355                 360                 365

Ile His Ile Ala Gly Ala Gly Leu Ala Arg Gly Tyr Leu Gly Arg Pro
    370                 375                 380

Ala Leu Thr Ala Glu Arg Phe Val Ala Asp Pro Phe Gly Thr Pro Gly
385                 390                 395                 400

Glu Arg Met Tyr Arg Thr Gly Asp Arg Val Arg Val Arg Asp Asp Gly
                405                 410                 415

Gln Leu Glu Phe Val Gly Arg Val Asp Asp Gln Ala Lys Ile Arg Gly
            420                 425                 430

Phe Arg Val Glu Pro Gly Glu Val Glu Ala Val Leu Arg Asp His Pro
        435                 440                 445

Glu Val Ala Gln Ala Ala Val Val Val Arg Glu Asp Thr Pro Gly Asp
    450                 455                 460

Gln Arg Leu Val Ala Tyr Val Val Pro Asp His Pro Ala Val Arg Gln
465                 470                 475                 480

Ala Asp Asp Thr Thr Ser Glu His Val Glu Glu Trp Gln Arg Leu Tyr
                485                 490                 495

Asp Glu Val Tyr Ser Ala Val Gly Ala Leu Pro Leu Gly Glu Asp Phe
            500                 505                 510

Ser Gly Trp Asn Ser Thr Tyr Asp Gly Glu Pro Ile Pro Val Pro Gln
        515                 520                 525

Met Gln Ala Trp Arg Asp Ala Thr Val Asp Ser Ile Arg Ala Leu Arg
    530                 535                 540

Pro Arg Arg Val Leu Glu Ile Gly Val Gly Thr Gly Leu Leu Leu Ser
545                 550                 555                 560

Arg Leu Ala Gly Asp Cys Glu Ala Tyr Trp Ala Thr Asp Phe Ser Ala
                565                 570                 575

Glu Val Ile Glu Thr Leu Gly Lys Lys Val Asp Val Asp Pro Val Leu
            580                 585                 590

Arg Glu Lys Val His Leu Leu His Gly Pro Ala His Asp Leu Pro Gly
        595                 600                 605

Leu Pro Glu Gly Tyr Phe Asp Thr Val Val Leu Asn Ser Val Ile Gln
    610                 615                 620

Tyr Phe Pro Ser Ala Asp Tyr Leu Val Ser Val Leu Arg Glu Ala Ala
625                 630                 635                 640

Arg Leu Leu Ala Pro Gly Gly Arg Val Phe Val Gly Asp Ile Arg His
                645                 650                 655

Leu Arg Leu Leu Arg Pro Leu Arg Ser Ala Val Arg Leu Arg Ser Ala
            660                 665                 670

Thr Arg Arg Glu Ala Ser Ala Ser Ala Val Arg Ala Ala Val Glu Gln
        675                 680                 685

Asp Leu Val Asp Glu Lys Glu Leu Leu Leu Asp Pro Ala Phe Phe Ala
    690                 695                 700

Ala Val Pro Arg Trp Ile Pro Gln Leu Arg Gly Val Arg Thr Ala Val
705                 710                 715                 720

Gln Arg Gly Thr His His Asn Glu Leu Thr Arg Tyr Arg Tyr Asp Ala
                725                 730                 735

Val Leu Ile Lys Glu Pro Val Glu Thr Gly Thr Ala Ala Pro Asp Ala
            740                 745                 750

Gln Thr Leu Thr Trp Gly Thr Asp Val Ser Gly Leu Gln Glu Leu Ser
```

```
        755                 760                 765

Gly Leu Leu Ala Arg Thr Arg Thr Ser Leu Leu Leu Arg Gly Val Pro
    770                 775                 780

Asn Ser Arg Ile Leu Gly Glu Ala Ser Ala Ala Thr Ala Leu Thr Thr
785                 790                 795                 800

Ala Arg Ser Leu Asp Glu Pro Leu Arg Leu Leu Gln Glu Pro Ala Ala
            805                 810                 815

Gly Ile Asp Pro Glu Glu Leu His Ala Leu Gly Gly Gly Ala Gly Cys
            820                 825                 830

Glu Val His Leu Thr Trp Ser Ala Gln Asp Pro Thr Arg Leu Asp Ala
        835                 840                 845

Cys Phe Thr Pro Val Gly Gly Glu Pro Gly Ala Val Pro Leu Ala Glu
    850                 855                 860

Ser Ala Asp Ser Gly Arg Thr Ser Pro Gly Asp His Ala Asn Gln Pro
865                 870                 875                 880

Thr Thr His Arg Thr Gly Asn Ala Leu Met Gly Lys Leu Pro Gly Tyr
            885                 890                 895

Leu Ala Ala Arg Leu Pro Ala Tyr Leu Arg Pro Ser Ala Val Val Arg
            900                 905                 910

Ile Ala Ser Leu Pro Leu Thr Val Asn Gly Lys Leu Asp Arg Thr Ala
        915                 920                 925

Leu Pro Arg Pro Ala Leu Phe Pro Arg Ala Asp Gly Gln Ala Pro Arg
    930                 935                 940

Thr Pro Arg Glu Glu Ile Leu Ala Asn Leu Phe Ala Asp Val Leu Gly
945                 950                 955                 960

Leu Pro Gly Val Pro Arg Asp Ala Asp Phe Phe Ala Leu Gly Gly Asn
            965                 970                 975

Ser Leu Leu Ala Thr Arg Leu Val Gly Arg Ile Ala Lys His Leu Glu
            980                 985                 990

Val Asp Val Pro Ile Ala Trp Ile  Phe Glu Thr Pro Thr  Val Glu Gly
        995                 1000                1005

Leu Ala  Gly Arg Thr Ala Pro  Ala Ser Arg Leu Arg  Pro Leu Leu
    1010                1015                1020

Leu Cys  Arg Asp Glu Asn His  Ala Ala Val Pro Leu  Ser His Ser
    1025                1030                1035

Gln Tyr  Gly Met Trp Phe Ile  Asn Gln Leu Gly Gly  Pro Ala Ser
    1040                1045                1050

Arg Ile  Tyr Asn Val Pro Tyr  Cys Leu Arg Ile Thr  Gly Arg Val
    1055                1060                1065

Asp Thr  Gly Ala Leu Arg Thr  Ala Leu Asp Asp Val  Val Ala Arg
    1070                1075                1080

His Glu  Pro Leu Arg Thr Val  Phe Pro Asp Asp Gly  Asp Gly Pro
    1085                1090                1095

Arg Gln  Arg Val Leu Ala Pro  Glu Asp Ala Ala Val  Val Leu His
    1100                1105                1110

Glu Thr  Asp Ala Ala Glu Asp  Arg Leu Ala Gly His  Leu Ala Arg
    1115                1120                1125

Ala Ala  Ala Glu Pro Phe Glu  Leu Arg Thr Asp Leu  Pro Leu Arg
    1130                1135                1140

Ala Arg  Leu Phe Arg His Gly  Gln Asp Arg Tyr Thr  Leu Leu Leu
    1145                1150                1155

Leu Met  His His Ile Thr Val  Asp Ala Trp Ser Leu  Ala Pro Leu
    1160                1165                1170
```

Thr Ala Asp Leu Ala His Ala Tyr Arg Ala Arg Leu Gly Gln Arg
1175 1180 1185

Ala Pro Gln Trp Gln Pro Leu Pro Val His Tyr Arg Asp Tyr Ala
1190 1195 1200

Val Trp His Asn Glu Gln Ala Ala Glu Ala Gln Asp Arg Gly Ser
1205 1210 1215

Gly Phe Gly Arg Gln Leu Ala Phe Trp Glu Arg Thr Leu Arg Gly
1220 1225 1230

Leu Pro Val Glu Thr Arg Leu Pro Ala Asp Arg Ser Arg Pro Ala
1235 1240 1245

Arg Pro Thr Tyr Arg Gly Gly Thr Val His Thr His Val Glu Ala
1250 1255 1260

Ser Leu His Gln Glu Leu Leu Asn Cys Ala Arg Glu Thr Gly Ala
1265 1270 1275

Thr Leu Phe Met Val Leu His Ala Ala Leu Ala Ala Leu Leu Thr
1280 1285 1290

Arg Leu Gly Gly Gly Thr Asp Ile Val Val Gly Thr Ala Ala Ala
1295 1300 1305

Ala Arg Thr Asp Pro Ala Leu Asp Asp Leu Val Gly Leu Phe Ala
1310 1315 1320

Asn Ser Val Val Leu Arg Val Asp Thr Ser Gly Asp Pro Thr Phe
1325 1330 1335

Arg Thr Leu Leu Ala Arg Thr Arg Ala Val Asp Leu Asp Ala Phe
1340 1345 1350

Thr His Gln Glu Val Pro Phe Asp Gln Val Val Asp Arg Val Asn
1355 1360 1365

Pro Ala Arg His Pro Ala Arg His Pro Leu Tyr Gln Thr Ala Leu
1370 1375 1380

Val Leu His Ala Pro Pro Gly Asp Gly His Arg Ala Asp Ser Val
1385 1390 1395

Thr Leu Thr Pro Glu Pro Pro Pro Asn Thr Gly Thr Ala Arg Phe
1400 1405 1410

Asp Leu Met Phe Asn Trp Asp Glu Ser Arg Asp Ser Ala Gly Leu
1415 1420 1425

Ala Gln Gly Leu Thr Gly Arg Thr Glu Tyr Ser Ser Asp Leu Phe
1430 1435 1440

Ser Gln Glu Thr Val Glu Leu Leu Leu Glu Arg Tyr Leu Leu Leu
1445 1450 1455

Leu Ser Ala Ala Val Arg Asp Pro Asp Ala Arg Leu His Thr Leu
1460 1465 1470

Asp Ile Leu Thr Glu Pro Glu Arg Arg Ala Phe Ser Pro Arg Pro
1475 1480 1485

<210> SEQ ID NO 5
<211> LENGTH: 1188
<212> TYPE: DNA
<213> ORGANISM: Streptomyces scabies

<400> SEQUENCE: 5
atggaatctc cggccaccca ggtcgacccg gcgaactcgc cgttggagcc ctatcacatc 60
tacccggagg ccaagtcctg cccggtggcg aaggtcggtc tgtggaacgg cacgccggcg 120
cacgtgttct ccgggtatga ggatgtgcgg accgtgctgc aggacaggcg gttcagctcg 180
gactcgcgcc gacccaactt caccgaactc actccgacgc tccagtcgca ggccgcggca 240

-continued

```
ccgccgttcg tacgcaccga caatcctgat caccggcgcc tgcgaggcac catcgcacgc    300

gagttcctgc ccaagcacat cgagctgctg cgccccgcga tccgcgagat cgtccagggt    360

gtgctcgacg ggctcgccga gaccgcgcct ccccaggaca tgctcgaggc cttcgccgta    420

ccggtcgcgt ccgcgaccgt cttccggctg ctggggattc cggccgagga ccgcgcgttg    480

ctcacccgat gcgtcaaggg cgtggtctcg gcggtgggga gcgaggacga aggtgccgag    540

gtgttccgga cactcggcga gtacatcggc gggctcgtcc aggacccctc cgaactgccc    600

gaggacagcc tgatccggcg cctggtgacg ggcccgtacc aggagaagca gctcaccttc    660

cacgagacca tcggcgtgat cctcatgctc atcgtcgggg gctacgacac gacggccagc    720

accatctcgc tgtccttggt gagttatgca ctgcagccgg agaagttctc cgtcgtccac    780

gaacacccgg agcggatacc cctgctcgtc gaggagttgc tgcgctatca caccgtctcg    840

cagctcggac tgggcaggat cgccaccgag gacgtcgagg tgggcggcgt cacggtgcgg    900

gccggccaga tggtggtggc ggcgctcccc ctggccaacc gggacgagag tgtcttcccg    960

aacccggacg aactcgactt cgaccgcccg tccgtgcccc atgtcggctt cggttacgga   1020

ccccaccagt gcgtcggcca ggcactggcc cgagtcgaac tccaggaggc cattcccgcg   1080

gtgatccgac ggctgcccgg catgcggctc gcctgcgctc tggaagacct gccgttccgg   1140

cacgacatgg ccacctacgg catccatgag ctgcccatga cctggtga                1188
```

<210> SEQ ID NO 6
<211> LENGTH: 395
<212> TYPE: PRT
<213> ORGANISM: Streptomyces scabies

<400> SEQUENCE: 6

```
Met Glu Ser Pro Ala Thr Gln Val Asp Pro Ala Asn Ser Pro Leu Glu
1               5                   10                  15

Pro Tyr His Ile Tyr Pro Glu Ala Lys Ser Cys Pro Val Ala Lys Val
            20                  25                  30

Gly Leu Trp Asn Gly Thr Pro Ala His Val Phe Ser Gly Tyr Glu Asp
        35                  40                  45

Val Arg Thr Val Leu Gln Asp Arg Arg Phe Ser Ser Asp Ser Arg Arg
    50                  55                  60

Pro Asn Phe Thr Glu Leu Thr Pro Thr Leu Gln Ser Gln Ala Ala Ala
65                  70                  75                  80

Pro Pro Phe Val Arg Thr Asp Asn Pro Asp His Arg Arg Leu Arg Gly
                85                  90                  95

Thr Ile Ala Arg Glu Phe Leu Pro Lys His Ile Glu Leu Leu Arg Pro
            100                 105                 110

Ala Ile Arg Glu Ile Val Gln Gly Val Leu Asp Gly Leu Ala Glu Thr
        115                 120                 125

Ala Pro Pro Gln Asp Met Leu Glu Ala Phe Ala Val Pro Val Ala Ser
    130                 135                 140

Ala Thr Val Phe Arg Leu Leu Gly Ile Pro Ala Glu Asp Arg Ala Leu
145                 150                 155                 160

Leu Thr Arg Cys Val Lys Gly Val Val Ser Ala Val Gly Ser Glu Asp
                165                 170                 175

Glu Gly Ala Glu Val Phe Arg Thr Leu Gly Glu Tyr Ile Gly Gly Leu
            180                 185                 190

Val Gln Asp Pro Ser Glu Leu Pro Glu Asp Ser Leu Ile Arg Arg Leu
        195                 200                 205
```

```
Val Thr Gly Pro Tyr Gln Glu Lys Gln Leu Thr Phe His Glu Thr Ile
    210                 215                 220

Gly Val Ile Leu Met Leu Ile Val Gly Gly Tyr Asp Thr Thr Ala Ser
225                 230                 235                 240

Thr Ile Ser Leu Ser Leu Val Ser Tyr Ala Leu Gln Pro Glu Lys Phe
                245                 250                 255

Ser Val Val His Glu His Pro Glu Arg Ile Pro Leu Leu Val Glu Glu
            260                 265                 270

Leu Leu Arg Tyr His Thr Val Ser Gln Leu Gly Leu Gly Arg Ile Ala
        275                 280                 285

Thr Glu Asp Val Glu Val Gly Gly Val Thr Val Arg Ala Gly Gln Met
    290                 295                 300

Val Val Ala Ala Leu Pro Leu Ala Asn Arg Asp Glu Ser Val Phe Pro
305                 310                 315                 320

Asn Pro Asp Glu Leu Asp Phe Asp Arg Pro Ser Val Pro His Val Gly
                325                 330                 335

Phe Gly Tyr Gly Pro His Gln Cys Val Gly Gln Ala Leu Ala Arg Val
            340                 345                 350

Glu Leu Gln Glu Ala Ile Pro Ala Val Ile Arg Arg Leu Pro Gly Met
        355                 360                 365

Arg Leu Ala Cys Ala Leu Glu Asp Leu Pro Phe Arg His Asp Met Ala
    370                 375                 380

Thr Tyr Gly Ile His Glu Leu Pro Met Thr Trp
385                 390                 395


<210> SEQ ID NO 7
<211> LENGTH: 1173
<212> TYPE: DNA
<213> ORGANISM: Streptomyces scabies

<400> SEQUENCE: 7

ttgcccgccc cgtccccgac agcgtgcccg gcactggggc ccgattcgtc ccttggcccg     60

gtcccgtcgg cggaaccggc gacgccgcag tcctgcggcg tcgccgatcc aaatgaggct    120

gaggagttcc tgcgccagtt ccacgcggag cagtccgatc agcccgtccc gctcgcccgg    180

cgcctggagc aggtccgcgc cgccatcgac gccacgggca cctaccggca caccaccgcc    240

gagctcgtgt acggtgcccg cgtcgcgtgg cgcaactcca gtcgctgcat cggccgcctg    300

tactggaaca gcctgcgcgt cctggaccgc cgggacgcca cagcccccga tgagatccac    360

cggcacttgt gcacgcacct gcgccaggcg accaacggcg ggcgcatcag gccggtgatt    420

tcggtcttcg ccccggactc ccccggccgg cccggcccgc aggtgtggaa cgagcagctc    480

atccggtacg ccggctaccg ccgcgacgac ggcaccgtgc tcggtgaccc gcgcaccgcc    540

gacctcaccg aggccatcct ccgcctcggc tggcagggct gcccccaagg gccgttcgac    600

gtcctgcccc tggtcatcga cacccccgac gacaaacccc ggttcttcga gctgccgcgg    660

gagctggtct tggaggtccc tatcacccac cccgacgtcc cacgcctggc cgaactgggc    720

ctgcgctggc acgccgtacc cgtcatctcc aacatgcgcc tacgcatcgg cgggatggac    780

tacccgctcg ccccgttcaa cggctggtac atgggcacgg agatcggcgc ccgcaacctc    840

gtcgacgagg accgctacaa catgctcccc gccgtcgccg cctgcctcca gctggacacc    900

accagcgagt caaccctgtg gcgcgaccgc gccctggtcg agctcaacgt cgccgtcctg    960

cactccttcg aggccgcagg tgtccggatc agcgaccacc acgaggagtc ccggcgcttc   1020
```

-continued

```
ctcgcccacc tggccaagga ggaacgccag ggccgcaccg tatccgcaga ctggagctgg   1080

atcgtccccc cgctctccgg cggcatcacc cccgtgttcc accgttacta cgacaacgtc   1140

gaccagcgcc ccaacttcta cccccaccag tga                                1173


<210> SEQ ID NO 8
<211> LENGTH: 390
<212> TYPE: PRT
<213> ORGANISM: Streptomyces scabies

<400> SEQUENCE: 8

Leu Pro Ala Pro Ser Pro Thr Ala Cys Pro Ala Leu Gly Pro Asp Ser
1               5                   10                  15

Ser Leu Gly Pro Val Pro Ser Ala Glu Pro Ala Thr Pro Gln Ser Cys
            20                  25                  30

Gly Val Ala Asp Pro Asn Glu Ala Glu Glu Phe Leu Arg Gln Phe His
        35                  40                  45

Ala Glu Gln Ser Asp Gln Pro Val Pro Leu Ala Arg Arg Leu Glu Gln
    50                  55                  60

Val Arg Ala Ala Ile Asp Ala Thr Gly Thr Tyr Arg His Thr Thr Ala
65                  70                  75                  80

Glu Leu Val Tyr Gly Ala Arg Val Ala Trp Arg Asn Ser Ser Arg Cys
                85                  90                  95

Ile Gly Arg Leu Tyr Trp Asn Ser Leu Arg Val Leu Asp Arg Arg Asp
            100                 105                 110

Ala Thr Ala Pro Asp Glu Ile His Arg His Leu Cys Thr His Leu Arg
        115                 120                 125

Gln Ala Thr Asn Gly Gly Arg Ile Arg Pro Val Ile Ser Val Phe Ala
    130                 135                 140

Pro Asp Ser Pro Gly Arg Pro Gly Pro Gln Val Trp Asn Glu Gln Leu
145                 150                 155                 160

Ile Arg Tyr Ala Gly Tyr Arg Arg Asp Asp Gly Thr Val Leu Gly Asp
                165                 170                 175

Pro Arg Thr Ala Asp Leu Thr Glu Ala Ile Leu Arg Leu Gly Trp Gln
            180                 185                 190

Gly Cys Pro Gln Gly Pro Phe Asp Val Leu Pro Leu Val Ile Asp Thr
        195                 200                 205

Pro Asp Asp Lys Pro Arg Phe Phe Glu Leu Pro Arg Glu Leu Val Leu
    210                 215                 220

Glu Val Pro Ile Thr His Pro Asp Val Pro Arg Leu Ala Glu Leu Gly
225                 230                 235                 240

Leu Arg Trp His Ala Val Pro Val Ile Ser Asn Met Arg Leu Arg Ile
                245                 250                 255

Gly Gly Met Asp Tyr Pro Leu Ala Pro Phe Asn Gly Trp Tyr Met Gly
            260                 265                 270

Thr Glu Ile Gly Ala Arg Asn Leu Val Asp Glu Asp Arg Tyr Asn Met
        275                 280                 285

Leu Pro Ala Val Ala Ala Cys Leu Gln Leu Asp Thr Thr Ser Glu Ser
    290                 295                 300

Thr Leu Trp Arg Asp Arg Ala Leu Val Glu Leu Asn Val Ala Val Leu
305                 310                 315                 320

His Ser Phe Glu Ala Ala Gly Val Arg Ile Ser Asp His His Glu Glu
                325                 330                 335

Ser Arg Arg Phe Leu Ala His Leu Ala Lys Glu Glu Arg Gln Gly Arg
            340                 345                 350
```

```
Thr Val Ser Ala Asp Trp Ser Trp Ile Val Pro Pro Leu Ser Gly Gly
        355                 360                 365

Ile Thr Pro Val Phe His Arg Tyr Tyr Asp Asn Val Asp Gln Arg Pro
    370                 375                 380

Asn Phe Tyr Pro His Gln
385                 390


<210> SEQ ID NO 9
<211> LENGTH: 1221
<212> TYPE: DNA
<213> ORGANISM: Streptomyces scabies

<400> SEQUENCE: 9

gtgaccgtcc cctcgccgct cgccgacccg tccatcgtgc ccgacccccta ccctgtctac      60

gccgacctgg cccagcgccg ccccgtccac tgggtcgagc gcctgaacgc ctgggcggtc     120

ttgacgtacg ccgactgcgc cgccgggctg aaggatcccc ggctcaccgc cgaccggggg     180

acggaagtgc tggccgcgaa gttccccgga cagccgctgc cgccggacaa catcttccac     240

cgctggacca agaacgtggt gatgtacacg gacccgccgc tccacgacgc gctacgccgg     300

tccgtccgcg caggcttcac ccgtgccgcg caccagcact acgaccaagt cctccagaag     360

gtcgcgcacg acctggtcgc ttccatcccg gccggtgcca ccgagatcga cgccgtcccc     420

gccctggctg ccgaactccc cgtacgctcc gccgtgcacg ccttcggggt ccccgaggag     480

gacctcggat tcctcatccc gcgcgtgaat acgatcatga cgtaccactc cggtccgaag     540

gatcagccgg tgacgcagga gataatcctg gaaaagctca ccgacctgca cacgtacgcc     600

tccgaactcc tccagggcat gcggggcaag gtcctgccgg acaccgtcat cgcccgcctg     660

gcagccgccc aggacggcct gaccgagacc acgccggaac agaccgtgca ccagctggcg     720

ctggtgttca tcgcgttgtt cgcgcccacg acgccgggct ctctcagcag cggcacgctc     780

gcgttcgccc gcaacccgcg gcaggtcgaa cgcttcctgg cggaccaggc gtgcgtggac     840

aacacggcga acgaggtcct ccgctacaac gcctcgaacc agttcacctg gcgcgtcgcg     900

gccaaggacg tcgagatggg cggcgtacgg atcgaggccg ggcagactct cgccctgttc     960

ctgggctcgg ccaaccggga cgccaacatg ttcgagcgac cgaacgactt cgacctcgac    1020

cgtcccaaca gcgctcggca cctgtcgttc ggccaagggg tgcacgcctg tctcgccgcg    1080

cagctcatct ccctgcagct gaagtggttc tacgtcgccc tgctgaaccg cttcccgggc    1140

atccggacgg cgggcgagcc gatctggaac gagaacctcg aattccgctc ccttcgctcc    1200

ctgccgctca gcctccgctg a                                              1221


<210> SEQ ID NO 10
<211> LENGTH: 406
<212> TYPE: PRT
<213> ORGANISM: Streptomyces scabies

<400> SEQUENCE: 10

Val Thr Val Pro Ser Pro Leu Ala Asp Pro Ser Ile Val Pro Asp Pro
1               5                   10                  15

Tyr Pro Val Tyr Ala Asp Leu Ala Gln Arg Arg Pro Val His Trp Val
            20                  25                  30

Glu Arg Leu Asn Ala Trp Ala Val Leu Thr Tyr Ala Asp Cys Ala Ala
        35                  40                  45

Gly Leu Lys Asp Pro Arg Leu Thr Ala Asp Arg Gly Thr Glu Val Leu
    50                  55                  60
```

-continued

```
Ala Ala Lys Phe Pro Gly Gln Pro Leu Pro Pro Asp Asn Ile Phe His
65                  70                  75                  80

Arg Trp Thr Lys Asn Val Val Met Tyr Thr Asp Pro Pro Leu His Asp
                85                  90                  95

Ala Leu Arg Arg Ser Val Arg Ala Gly Phe Thr Arg Ala Ala His Gln
            100                 105                 110

His Tyr Asp Gln Val Leu Gln Lys Val Ala His Asp Leu Val Ala Ser
        115                 120                 125

Ile Pro Ala Gly Ala Thr Glu Ile Asp Ala Val Pro Ala Leu Ala Ala
    130                 135                 140

Glu Leu Pro Val Arg Ser Ala Val His Ala Phe Gly Val Pro Glu Glu
145                 150                 155                 160

Asp Leu Gly Phe Leu Ile Pro Arg Val Asn Thr Ile Met Thr Tyr His
                165                 170                 175

Ser Gly Pro Lys Asp Gln Pro Val Thr Gln Glu Ile Ile Leu Glu Lys
            180                 185                 190

Leu Thr Asp Leu His Thr Tyr Ala Ser Glu Leu Leu Gln Gly Met Arg
        195                 200                 205

Gly Lys Val Leu Pro Asp Thr Val Ile Ala Arg Leu Ala Ala Ala Gln
    210                 215                 220

Asp Gly Leu Thr Glu Thr Thr Pro Glu Gln Thr Val His Gln Leu Ala
225                 230                 235                 240

Leu Val Phe Ile Ala Leu Phe Ala Pro Thr Thr Pro Gly Ser Leu Ser
                245                 250                 255

Ser Gly Thr Leu Ala Phe Ala Arg Asn Pro Arg Gln Val Glu Arg Phe
            260                 265                 270

Leu Ala Asp Gln Ala Cys Val Asp Asn Thr Ala Asn Glu Val Leu Arg
        275                 280                 285

Tyr Asn Ala Ser Asn Gln Phe Thr Trp Arg Val Ala Ala Lys Asp Val
    290                 295                 300

Glu Met Gly Gly Val Arg Ile Glu Ala Gly Gln Thr Leu Ala Leu Phe
305                 310                 315                 320

Leu Gly Ser Ala Asn Arg Asp Ala Asn Met Phe Glu Arg Pro Asn Asp
                325                 330                 335

Phe Asp Leu Asp Arg Pro Asn Ser Ala Arg His Leu Ser Phe Gly Gln
            340                 345                 350

Gly Val His Ala Cys Leu Ala Ala Gln Leu Ile Ser Leu Gln Leu Lys
        355                 360                 365

Trp Phe Tyr Val Ala Leu Leu Asn Arg Phe Pro Gly Ile Arg Thr Ala
    370                 375                 380

Gly Glu Pro Ile Trp Asn Glu Asn Leu Glu Phe Arg Ser Leu Arg Ser
385                 390                 395                 400

Leu Pro Leu Ser Leu Arg
                405
```

<210> SEQ ID NO 11
<211> LENGTH: 198
<212> TYPE: DNA
<213> ORGANISM: Streptomyces scabies

<400> SEQUENCE: 11

```
gtgccctcac ccttcgacga ccatgacggg cagttccatg tgctccgcaa cgaggaaggc      60

cagttctcac tctggccgaa tttcgccgac atcccctccg ggtggcgttc cgtgagcggg     120
```

ccgagccccc gcggaagcgc ccttgagtac atcgagaagg aatggacgga catgcgcccg 180
gcgtccgtcc gtgaatga 198

<210> SEQ ID NO 12
<211> LENGTH: 65
<212> TYPE: PRT
<213> ORGANISM: Streptomyces scabies

<400> SEQUENCE: 12

Val Pro Ser Pro Phe Asp Asp His Asp Gly Gln Phe His Val Leu Arg
1 5 10 15

Asn Glu Glu Gly Gln Phe Ser Leu Trp Pro Asn Phe Ala Asp Ile Pro
20 25 30

Ser Gly Trp Arg Ser Val Ser Gly Pro Ser Pro Arg Gly Ser Ala Leu
35 40 45

Glu Tyr Ile Glu Lys Glu Trp Thr Asp Met Arg Pro Ala Ser Val Arg
50 55 60

Glu
65

<210> SEQ ID NO 13
<211> LENGTH: 638
<212> TYPE: DNA
<213> ORGANISM: Streptomyces scabies

<400> SEQUENCE: 13
atgacggacg gcgacgttcc cttttcgatg aatgtgcccg ttgcttcgcg actcctcgta 60
ctgcgtttcg ccgacgaagc gaaggatgga ctcccggtgt cgcctcgggg gacttttatc 120
gtgacggatg ctgccaaggg tcccggatcc ggatttcttt tttcgttctt gaataccctg 180
gctgtggaga tgatgaaaac cgatgggatt ctgtcctcgt atatggagga ggtcgtgcgc 240
atcctggcga tctccgcgac gcgaatcgca tatgccgagc tcggaaagca ttactctggg 300
ggatgcgatc cacttctgat cgcggttcag gagtcgatcg accggcagtt ggccgacccc 360
gagatcagcc cggcgaccct cgcggccgaa cacaacatat cggtgcgtca gttacatcga 420
gttttcggac cgatcgggga aagcgtcatg agctatgtca aacgccgtcg cctggagcgt 480
ttcgcatgcg atctgaggga tccgagcctg ggcaccggga agatcaatga gctggcggcg 540
gactggggga tgctggatgc cgcgatgctg agcagacact tccgctgcgc ctacggaatg 600
tcgccccgcg attaccggaa gcagcactgt ttcacctg 638

<210> SEQ ID NO 14
<211> LENGTH: 212
<212> TYPE: PRT
<213> ORGANISM: Streptomyces scabies

<400> SEQUENCE: 14

Met Thr Asp Gly Asp Val Pro Phe Ser Met Asn Val Pro Val Ala Ser
1 5 10 15

Arg Leu Leu Val Leu Arg Phe Ala Asp Glu Ala Lys Asp Gly Leu Pro
20 25 30

Val Ser Pro Arg Gly Thr Phe Ile Val Thr Asp Ala Ala Lys Gly Pro
35 40 45

Gly Ser Gly Phe Leu Phe Ser Phe Leu Asn Thr Leu Ala Val Glu Met
50 55 60

Met Lys Thr Asp Gly Ile Leu Ser Ser Tyr Met Glu Glu Val Val Arg
65 70 75 80

```
Ile Leu Ala Ile Ser Ala Thr Arg Ile Ala Tyr Ala Glu Leu Gly Lys
                85                  90                  95

His Tyr Ser Gly Gly Cys Asp Pro Leu Leu Ile Ala Val Gln Glu Ser
            100                 105                 110

Ile Asp Arg Gln Leu Ala Asp Pro Glu Ile Ser Pro Ala Thr Leu Ala
        115                 120                 125

Ala Glu His Asn Ile Ser Val Arg Gln Leu His Arg Val Phe Gly Pro
    130                 135                 140

Ile Gly Glu Ser Val Met Ser Tyr Val Lys Arg Arg Arg Leu Glu Arg
145                 150                 155                 160

Phe Ala Cys Asp Leu Arg Asp Pro Ser Leu Gly His Arg Lys Ile Asn
                165                 170                 175

Glu Leu Ala Ala Asp Trp Gly Met Leu Asp Ala Ala Met Leu Ser Arg
            180                 185                 190

His Phe Arg Cys Ala Tyr Gly Met Ser Pro Arg Asp Tyr Arg Lys Gln
        195                 200                 205

His Cys Phe Thr
    210


<210> SEQ ID NO 15
<211> LENGTH: 323
<212> TYPE: DNA
<213> ORGANISM: Streptomyces albus

<400> SEQUENCE: 15

ctcgtgaggc tagctccgcc gcggaccccg ctcgcgccgg ggcccgccga acggtgccgg      60

gcgcgcggcg ccacgagtac ggcaggtgta ccgttgtcaa cgcctgacct gcggcaatca     120

aacatccggg tgaagtgatc tttccctcta ccggtgccga gcttctgcgt gctaggctcg     180

ccgcaagttg cagtttggtt tcccttgcag tacagagcct gcggagcatg tgaccgcagg     240

ctctcgtcat tttcagactt ttgcacttgt tttcacactt gcaggttctg gagcagggca     300

accctttggc ccaaggaggg ctt                                             323


<210> SEQ ID NO 16
<211> LENGTH: 639
<212> TYPE: DNA
<213> ORGANISM: Streptomyces albus

<400> SEQUENCE: 16

ggcgccgacc gcaccacact cacgagggcc cgccccacca acagggggcg ggccctctgt      60

gctggcctca ggcgccgacc gggctcggtg ccctcaagcg ccggccgggc tccaagggtg     120

gcctcaagcg ccggccgggc tgagttgggc cggtctgggc ccgcacgcgc gcctcactga     180

cggcctcaag cgccggccgg gctatctata gcccggccgg cgcttgaggc cgtctttggc     240

gcgcgcctgt gagcggacgg cccgtcaaag atcagcccgg ccggcgcttg aggccatctt     300

tcgagcccgg ccggcgtttg aggccacccc acccccgccc cggcaggggc ggcctgacct     360

ccgcatccgc cggcgcggac agggcacccc cagtagacgg gcgcggggcc ggaggcccct     420

agcgccttgc actctcctac cccgagtgct aattattggc gttagcactc tccgagtgag     480

agtgacagaa ggaccgggtc ggtgaggccc gctggccacg cggggcaagg aaccgcgagg     540

caggcaggcc gtccgtcgcg ggcgccagca cggtccggag tatccaccct cccccagaca     600

gagtccgggg ggacccccag tcctgggagg accacttca                            639
```

<210> SEQ ID NO 17
<211> LENGTH: 246
<212> TYPE: DNA
<213> ORGANISM: Streptomyces albus

<400> SEQUENCE: 17
tccagagatg tccggcgtgc gcgtcccgtg gggcgcgtgg gccggcggat tcgtccgtcc 60
gggcgggtcc tgcgacggtc tgcggccggg acgcataagg atcagcgcat cggggcattg 120
ttcctcgatt cgccttttgc gggagccctg gcgtagactg acgcgtcggc tctcgtgcac 180
ccgtatgtcc gtatggatgt gcaagggaca cggagccggt caaggtagtc gattcgaagg 240
gcgaag 246

<210> SEQ ID NO 18
<211> LENGTH: 302
<212> TYPE: DNA
<213> ORGANISM: Streptomyces albus

<400> SEQUENCE: 18
tacggcacct cctgcggaag cggcgctcac ctcggtgcgg ggcaccggtg ctgcgcatcc 60
ggtgccgaag cacccgatat acccagattg cgggcatcgg cggccggatt tcaaccggaa 120
gcggtcgtgc gggtactctg taccgtctgc accggtgtct gcccagatcc tggatcaccc 180
gctcaccacg gctcccgctc gcggggtccg ccgtcagcgg tggccgatac cgttgcgctc 240
gcatcaagac cctcctgcca cggaacgacc gtggccgctg agtccaaagg aggtgggttc 300
ta 302

<210> SEQ ID NO 19
<211> LENGTH: 379
<212> TYPE: DNA
<213> ORGANISM: Streptomyces albus

<400> SEQUENCE: 19
tccgctcctc cgggcggggt ccgcggatcc cgcccggagg ccgtgcttcc gggcgatttg 60
cctcgcgccg cccggctccc gtactcttcc ctagaagcca aagaccgctg gtcgttaccg 120
tctgctcctc ggagagggcg gtggccgaag gattccgctc acgcggacgg cctgcgtagg 180
tgactgtgga tgtgctcctg gacgtgttac ggccagtcga gctcacgccc cgtgcgcctg 240
cgccggggcg tttttcgtct tacgcagact ttcctgcccg acgtccttcc tcacgtgcct 300
gatccagacg gtcccagtgc tgtacgaggc tgatcgcaag gtcagtcgag gatcatcacc 360
ccggaaggag gccgaggct 379

<210> SEQ ID NO 20
<211> LENGTH: 221
<212> TYPE: DNA
<213> ORGANISM: Streptomyces albus

<400> SEQUENCE: 20
cgcacacctg ctctcgcaga tcacgcgcga cgcacagcag tatcaccaaa cgcagtgccc 60
gcctcttccc gtgtcctgaa cacgtgagaa gggcggtacc cccggtcgga ggccggggac 120
ccgttccgtt ccatgcccct cggcggctcc gtccgccccg gtggatcggc ggtcgggagc 180
ggcactgcgg cagacctccg acagacaact ggagccatta g 221

<210> SEQ ID NO 21
<211> LENGTH: 248
<212> TYPE: DNA

<213> ORGANISM: Streptomyces albus

<400> SEQUENCE: 21
atcccgctct tcagggattc accgggcctc tggtaagcaa ccaggcggcg gacgatcttc 60
ctccgatggc ttaggctgga gaggttggcc gtccgccgcc ctggacagcc cgcggacgct 120
caccactgag cagtccgcat atgacgctta ctacgccgca ggtccccgcg ccgcacccgt 180
cccgtcccgg atcggggaga gggatggcgc atacaggaaa ccccggcgag aaaggccgaa 240
ggccgatt 248

<210> SEQ ID NO 22
<211> LENGTH: 613
<212> TYPE: DNA
<213> ORGANISM: Streptomyces albus

<400> SEQUENCE: 22
gagtgctcct gcctcgggac cggcggacaa gcggccggtc tgatcatcgg ggcagcaaca 60
tatgactccg gcacatgtca gggagctccg aacgggtgcg ttcaccctga tgggggagta 120
cgggagcgcc cgtgcggaag atcctcgaag ggtgtcccgc cctcgttcgg ccgcgtccgc 180
gtttgacggc gggaaggccg ggggtaagct tctcggctcg attggctcta cgcggggccc 240
gtgtggcaga ctgtccgggt tgctcggttg agtgccgatg ccgcgcgcct cccgccggga 300
ggactggaag cgagtcccac agtactcgtc gcctcaactg ccccaggttc gccgaaggca 360
gcgctgtggc ggacgtacgg gaatcttccg ggaagcgtgt gcggggtacc agccaggcgc 420
ccggtggtca ccacaccgca aggtgtggct tcaccgaacc gcgtggccac ggtgtggaac 480
gcagcccccc agatgggatt ccgcgaggaa atttcgtacg ggcgggaagg cgacacaccc 540
gaccgcgtgg gtcggagaga gagaccggac cccgggtccc agagcgttac gagagacagg 600
actaccaagt agc 613

<210> SEQ ID NO 23
<211> LENGTH: 283
<212> TYPE: DNA
<213> ORGANISM: Streptomyces albus

<400> SEQUENCE: 23
cgggaattgt gccgggtttg cggcttgcgc cccgggtgtg cgccttcgcg cattgaccct 60
gtccggctgc ccccgtatgc tacaagttgc gctgcgagcc tgcgctcctc agacctagca 120
ggatgtgctc gcttctgttg tgtgtcccct cggttgtacg aggcgaggac ccccggtttc 180
ccggaggtcg cgcctctgaa ggctgtccga ctgctgcaga gtgaaaccgg ctccgtgcgc 240
ggcagtacct acgacttcat gtccgtaccg gagccctttc cca 283

<210> SEQ ID NO 24
<211> LENGTH: 373
<212> TYPE: DNA
<213> ORGANISM: Streptomyces albus

<400> SEQUENCE: 24
cgggacctcg gcgaccacct tgtcgagcag cgcctcgacg cccaggccgg tcttggcgga 60
gaccttgagc acgtcggagg ggtcgcgtgg tcctggttct tgagacgtcg agacgtcgag 120
gcgggcgggc ggcgcggagc cggacggggg cagtaggcgc ctcacctcgg gtgggctcac 180
gccgcctggg cgcgcccacc gggccggcac acgacccccg gggtccgcgg cccccatcgt 240
cccatgcgcg gggaccggcg accggtttgg gccgcgcgtg gggccgctgg tagcctggcc 300
cgatgtgtct cgtagccctc tcagcgtcgg gacacgaccg gaaacaccca acctgaacct 360
gtaaaggctc ttt 373

<210> SEQ ID NO 25
<211> LENGTH: 589
<212> TYPE: DNA
<213> ORGANISM: Streptomyces albus

<400> SEQUENCE: 25
cggccccctc cccgtggttc cccgttcccc gtccgcgccc gcgtggcccg tacggcggta 60
cggacggggc gggacgggtc aacgtactga ccccccggcc caggtggccc gcccttgacc 120
ggaatgaatc cccccgcccc gctactcggc gggaaagctg cgctctgtgg ccgaaaacac 180
acagagggtg ggagggggcg tgccgggggc cggcgaacga ttccggccag ggtgcccctg 240
gcaccacccg gcggcccggt gtagcgtccc ccgcgggacc agaagacgat catgcagcgg 300
agggcgccgg tccgccccgg ggtacggggc gtctgaccag cccgtccgct gcgcgtgcat 360
ttgttttgac cgaactccgt gcgataggta cgctcagacc ttgtgcctgg ggtgtgcctg 420
ggctcccgtg cgtgtccaac ccgcgcggcg agcgtcaggc gtcagcaccg caatctgcgc 480
ttctcccgtg tgctagcggg gctccgcggt attcgacaca cccgaccgcg tgggtcggga 540
gtgttccagg ttagctttac ctgttcggca cacagaaacc ggagaagta 589

<210> SEQ ID NO 26
<211> LENGTH: 398
<212> TYPE: DNA
<213> ORGANISM: Streptomyces albus

<400> SEQUENCE: 26
tgcccgctcc ctcttcacgt cccgacggcg aaaccggccg cccagtctgc cgtgcccggc 60
ccggtcccac cacctcctcc ggcggacgcc ccccgaagga gcggacccgc ccccgacttc 120
cggccggcgg cgcccccgac ctcgtagaac cccgcccgag cgcccggcgt caacctcgcg 180
cccacgcgtc acccggcccc ttcccggctg cggcgcgacc ggctccccgc ccctgctact 240
ctgtccgagg ccgtctgtgc ccacgtcccg agccccgcgt tcgacacgcg gtcccggacg 300
accggacgga tccatccgcc tcccgagtca ccgaagcctc ccctgagacg aagaccaggg 360
gcgctcggag gcaagcgaag acatcacaga ggagtacg 398

<210> SEQ ID NO 27
<211> LENGTH: 413
<212> TYPE: DNA
<213> ORGANISM: Streptomyces albus

<400> SEQUENCE: 27
ccggacctct cctcacgctc accctgcgcg cttccgcgcg acaggcacaa ttacccgtat 60
atgtcccgac tcgcccacag tctccgcctt cggccgggtc attccccega ccgacccggc 120 ccggcccacc catttccggc ccggccggcg tttgaggccg accggtgacg gacacccgaa 180
gccctcggag cgcgctcggc atcagcccgg acgacgcttg aggccacctc gaccgccgcc 240
ggacggcttc atccgaagtg cctctgaact ggtaaaacga gccgtgctgg cagctctctg 300
cacaaccagg cagaacaaaa cttgagcccg tccgactcaa ccgcattgac gcgccgcgtc 360
ccctcgtgca tccttgagtg agttccactc aagtagtcag ctggaggaat tga 413

<210> SEQ ID NO 28

-continued

```
<211> LENGTH: 97
<212> TYPE: DNA
<213> ORGANISM: Streptomyces albus

<400> SEQUENCE: 28

tgttcacatt cgaacggtct ctgctttgac aacatgctgt gcggtgttgt aaagtcgtgg      60

ccaggagaat acgacagcgt gcaggactgg gggagtt                               97


<210> SEQ ID NO 29
<211> LENGTH: 639
<212> TYPE: DNA
<213> ORGANISM: Streptomyces albus

<400> SEQUENCE: 29

ggcgccgacc gcaccacact cacgagggcc cgccccacca acagggggcg ggccctctgt      60

gctggcctca ggcgccgacc gggctcggtg ccctcaagcg ccggccgggc tccaagggtg     120

gcctcaagcg ccggccgggc tgagttgggc cggtctgggc ccgcacgcgc gcctcactga     180

cggcctcaag cgccggccgg gctatctata gcccggccgg cgcttgaggc cgtctttggc     240

gcgcgcctgt gagcggacgg cccgtcaaag atcagcccgg ccggcgcttg aggccatctt     300

tcgagcccgg ccggcgtttg aggccacccc acccccgccc cggcaggggc ggcctgacct     360

ccgcatccgc cggcgcggac agggcacccc cagtagacgg gcgcggggcc ggaggcccct     420

agcgccttgc actctcctac cccgagtgct aattattggc gttagcactc tccgagtgag     480

agtgacagaa ggaccgggtc ggtgaggccc gctggccacg cggggcaagg aaccgcgagg     540

caggcaggcc gtccgtcgcg ggcgccagca cggtccggag tatccaccct cccccagaca     600

gagtccgggg ggacccccag tcctgggagg accacttca                            639
```